(12) United States Patent
O'Shea et al.

(10) Patent No.: US 9,408,919 B2
(45) Date of Patent: *Aug. 9, 2016

(54) BIODEGRADABLE POLYMER—BIOACTIVE MOIETY CONJUGATES

(71) Applicant: POLYACTIVA PTY LTD., Melbourne, Victoria (AU)

(72) Inventors: Michael Shane O'Shea, Mulgrave (AU); Florian Hans Maximillian Graichen, Richmond (AU); Russell John Tait, Balwyn (AU); Heng Chy Taing, Mount Waverley (AU); Justine Leigh Jeffery, Mitcham (AU)

(73) Assignee: POLYACTIVA PTY LTD., Melbourne, Victoria (AU)

( * ) Notice: Subject to any disclaimer, the term of this patent is extended or adjusted under 35 U.S.C. 154(b) by 149 days.

This patent is subject to a terminal disclaimer.

(21) Appl. No.: 13/966,540

(22) Filed: Aug. 14, 2013

(65) Prior Publication Data

US 2014/0046018 A1   Feb. 13, 2014

Related U.S. Application Data

(63) Continuation of application No. 13/082,841, filed on Apr. 8, 2011, now Pat. No. 8,535,655, which is a continuation-in-part of application No. PCT/AU2009/001342, filed on Oct. 9, 2009, and a continuation-in-part of application No. PCT/AU2009/001341, filed on Oct. 9, 2009.

(60) Provisional application No. 61/139,722, filed on Dec. 22, 2008.

(30) Foreign Application Priority Data

Oct. 10, 2008  (AU) .............................. 2008905262
Oct. 10, 2008  (AU) .............................. 2008905263

(51) Int. Cl.
| | | |
|---|---|---|
| *A61K 47/48* | (2006.01) |
| *C07C 69/40* | (2006.01) |
| *C07C 69/67* | (2006.01) |
| *C07C 69/675* | (2006.01) |
| *C07D 215/56* | (2006.01) |
| *C07D 317/24* | (2006.01) |
| *C07D 317/26* | (2006.01) |
| *C07D 319/06* | (2006.01) |
| *C07D 405/12* | (2006.01) |
| *C07D 498/06* | (2006.01) |
| *C07F 9/40* | (2006.01) |
| *C08G 18/28* | (2006.01) |
| *C08G 18/42* | (2006.01) |

(52) U.S. Cl.
CPC ......... *A61K 47/482* (2013.01); *A61K 47/48192* (2013.01); *C07C 69/40* (2013.01); *C07C 69/67* (2013.01); *C07C 69/675* (2013.01); *C07D 215/56* (2013.01); *C07D 317/24* (2013.01); *C07D 317/26* (2013.01); *C07D 319/06* (2013.01); *C07D 405/12* (2013.01); *C07D 498/06* (2013.01); *C07F 9/4075* (2013.01); *C07F 9/4081* (2013.01); *C08G 18/284* (2013.01); *C08G 18/428* (2013.01); *C08G 18/4277* (2013.01); *C07C 2101/14* (2013.01); *C08G 2230/00* (2013.01)

(58) Field of Classification Search
USPC .................. 424/78.27, 78.36, 423; 604/891.1
See application file for complete search history.

(56) References Cited

U.S. PATENT DOCUMENTS

| | | | |
|---|---|---|---|
| 5,798,115 A | 8/1998 | Santerre et al. | |
| 8,535,655 B2 | 9/2013 | O'Shea et al. | |
| 2003/0097120 A1 | 5/2003 | Santerre | |
| 2005/0255082 A1 | 11/2005 | Santerre et al. | |
| 2006/0051394 A1* | 3/2006 | Moore et al. ................. 424/423 |

FOREIGN PATENT DOCUMENTS

| | | | |
|---|---|---|---|
| WO | WO 02/26867 A2 | 4/2002 |
| WO | WO 2004/014973 A2 | 2/2004 |
| WO | WO 2006/024953 A2 | 3/2006 |
| WO | WO 2008/053362 A2 | 5/2008 |
| WO | WO 2008/060780 A2 | 5/2008 |
| WO | WO 2009/102795 A1 | 8/2009 |

OTHER PUBLICATIONS

Ouchi et al., "Design of Poly(α-malic acid)-5FU Conjugate Exhibiting Antitumor Activity," British Polymer Journal, vol. 23, pp. 221-228, 1990.

Ljubimova et al., "Poly(malic acid) nanoconjugates containing various antibodies and oligonucleotides for multitargeting drug delivery," Nanomedicine, vol. 3, No. 2, pp. 247-265, 2008.

Davaran et al., "Synthesis and Hydrolysis of Polyurethanes Containing Ibuprofen Pendent Groups," Journal of Bioactive and Compatible Polymers, vol. 12, pp. 47-58, Jan. 1997.

International Search Report issued for application No. PCT/AU2009/001342 on Dec. 18, 2009.

International Search Report issued for application No. PCT/AU2009/001341 on Dec. 11, 2009.

(Continued)

*Primary Examiner* — Walter Webb
(74) *Attorney, Agent, or Firm* — Foley & Lardner LLP

(57) ABSTRACT

The invention relates to a biodegradable polymer comprising a plurality of releasable bioactive moieties, the releasable bioactive moieties being pendant from and covalently bonded to the biodegradable polymer backbone, wherein the biodegradable polymer backbone is formed from monomeric units that are each coupled via a biodegradable moiety, and wherein the bioactive moieties are capable of being released at a rate equal to or faster than the rate of biodegradation of the polymer backbone.

18 Claims, 5 Drawing Sheets

(56) References Cited

OTHER PUBLICATIONS

Woo et al., "Biological characterization of a novel biodegradable antimicrobial polymer synthesized with fluroquinolones," J. Biomed. Mater. Res., vol. 59, pp. 35-45, 2002.

Woo et al., "Synthesis and characterization of a novel biodegradeable antimicrobial polymer," Biomaterials, vol. 21, pp. 1235-1246, 2000.

Office Action issued on Nov. 2, 2012 in U.S. Appl. No. 13/082,841 (U.S. Pat. No. 8,535,655).

Office Action issued on Jan. 2, 2013 in U.S. Appl. No. 13/082,841 (U.S. Pat. No. 8,535,655).

Notice of Allowance issued on May 15, 2013 in U.S. Appl. No. 13/082,041 (U.S. Pat. No. 8,535,655).

Supplementary European Search Report issued on Oct. 17, 2014 in application No. EP 09818692.

Supplementary European Search Report issued on Dec. 2, 2013 in application No. EP 09818693.

Roseeuw et al., "Synthesis, Degradation, and Antimicrobial Properties of Targeted Macromolecular Prodrugs of Norfloxacin," Antimicrobial Agents and Chemotherapy, vol. 47, No. 11, pp. 3435-3441, Nov. 2003.

Breton et al., "Norfloxacin-Poly(L-Lysine Citramide Imide) Conjugates and Structure-dependence of the Drug Release," Journal of Drug Targeting, vol. 12, No. 5, pp. 297-307, Jun. 2004.

\* cited by examiner

BIODEGRADABLE POLYMER—BIOACTIVE MOIETY CONJUGATES

FIELD OF INVENTION

The present invention relates in general to polymer-bioactive moiety conjugates. In particular, the present invention relates to biodegradable polymer-bioactive moiety conjugates, to methods for preparing the polymers, and to monomer-bioactive moiety conjugates suitable for preparing the polymers. The conjugates can be used as coatings, scaffolds, stents and dressings for biomedical applications and in drug delivery devices. The invention also relates to a sustained bioactive moiety delivery system comprising the conjugate, and also to a method of delivering a bioactive moiety to a subject.

BACKGROUND

The targeted and controlled delivery of small molecule therapeutics is an area of considerable current interest. The site-specific delivery of a therapeutic agent is a highly desirable feature for the treatment of many different conditions. In particular, products may be implanted in the body of humans or animals which contain therapeutics. However, there is a need to increase the efficacy and safety of such products.

One form of drug delivery involves the use of polymers to carry/retain the drug moiety to/at a specific location. Several approaches to this have been developed. Early controlled release methods involved drug-polymer formulations that released the drug upon breakdown of the polymer structure under physiological conditions, particularly through oral administration. Later developments included the preparation of drug-polymer systems based on admixing or on covalent linking.

The admixture approach involves the preparation of a polymer drug mixture that is then compounded into a solid device. The linking approach involves using drug molecules as monomers in formation of the polymer so that they form part of the polymer backbone, or covalently attaching drug molecules to a pre-formed polymer backbone. The linking approach gives rise to so called drug-polymer conjugate.

A major disadvantage of the admixture approach is that the release of the therapeutic agent is largely dependent on the breakdown of the polymer structure. This results in poor control of the rate of drug release with the possibility of uncontrolled dosages being delivered. Furthermore, the amount of drug that can be loaded into an admixture is limited (typically <10% by weight).

The linking approach also has a number of problems associated with it. Where the drug forms part of the polymer backbone, the polymer structure must degrade in order to release the drug. This will of course be disadvantageous where it is desirable to at least maintain the polymer structure while the drug is being released. Covalently attaching drug molecules to a pre-formed polymer backbone can also be problematic. In particular, steric and thermodynamic constraints can affect the amount of bioactive moiety that can be covalently attached, and also impact on the distribution of the bioactive moiety along the polymer backbone, which in turn can reduce control over the release of the bioactive moiety.

An opportunity therefore remains to develop new polymer-bioactive moiety conjugates which address or ameliorate one or more disadvantages or shortcomings associated with existing materials and/or their method of manufacture, or to at least provide a useful alternative to such materials and their method of manufacture.

SUMMARY OF THE INVENTION

The present invention therefore provides a biodegradable polymer comprising a plurality of releasable bioactive moieties, the releasable bioactive moieties being pendant from and covalently bonded to the biodegradable polymer backbone, wherein the biodegradable polymer backbone is formed from monomeric units that are each coupled via a biodegradable moiety, and wherein the bioactive moieties are capable of being released at a rate equal to or faster than the rate of biodegradation of the polymer backbone.

An important feature of the invention is that the bioactive moieties are capable of being released at a rate equal to or faster than the rate of biodegradation of the polymer backbone. By providing the biodegradable polymer with such relative rates of release and biodegradation it can advantageously release bioactive moiety without the polymer backbone undergoing substantial biodegradation.

It has been found that the biodegradable polymers according to the invention are particularly useful in applications where controlled delivery of bioactive moieties is required while maintaining the structural integrity of the polymer backbone. For example, in providing a coating for use in infection control, the biodegradable polymers according to the invention retain the material properties of the polymer backbone for periods of time sufficient to allow substantial delivery of a bioactive moiety. The polymer backbone according to the invention is also biodegradable such that after a period of time the backbone degrades into biocompatible degradation products. The polymer backbone is preferably resorbable in vivo.

The biodegradable polymers in accordance with the invention may also be defined in terms a molecular structure.

The invention therefore also provides a biodegradable polymer comprising as part of its polymer backbone a plurality of moieties of general formula (I):

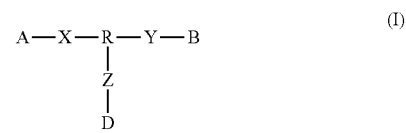

where:

A and B, which are the same or different, represent the remainder of the polymer backbone and (i) comprise one or more —X—R(ZD)-Y— moieties as shown in formula (I), and (ii) are each formed from monomeric units that are coupled via a biodegradable moiety;

X and Y are each independently a biodegradable moiety;

R represents a linear or branched optionally substituted hydrocarbon;

Z is a spacer moiety; and

D is a releasable bioactive moiety;

wherein the bioactive moieties (D) are capable of being released at a rate equal to or faster than the rate of biodegradation of the polymer backbone.

Each —X—R(ZD)-Y— moiety of the biodegradable polymers may be the same or different.

Each X, Y, R, Z and D in a given —X—R(ZD)-Y— moiety of the biodegradable polymers may be the same or different.

For avoidance of any doubt, the "moiety of general formula (I)" is intended to be a reference to:

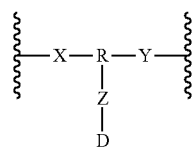

with A and B being presented in formula (I) to (i) more clearly depict that the "moiety" forms part of the polymer backbone, and (ii) define the nature of the remainder of the polymer backbone.

As used herein the expression forming "part of the polymer backbone" means that the moiety of formula (I) (i.e. excluding A and B) is part of the string of atoms that are each connected so as to form the polymer chain (i.e. including A and B). In other words, the moiety of formula (I) is not pendant from the polymer backbone. Having said this, it will be appreciated that groups Z and D in the moiety of formula (I) will be pendant from the polymer backbone.

Examples of A and B are discussed in more detail below, but include polyurethane, polyanhydride, polycarbonate, polyurea, polyamide, polyimide and polyester polymer chains, as well as copolymers thereof.

For example, the moiety of general formula (I) may in conjunction with a suitable comonomer form a repeat unit of a polyester, polyurethane or polyanhydride as illustrated below in general formula (Ia), (Ib) and (Ic), respectively:

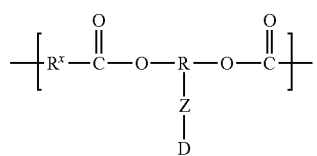

where R, Z and D are as herein defined and $R^x$ is an optionally substituted alkyl, aryl or alkylaryl group, wherein for each repeat unit of the polyester each R, Z, D and $R^x$ may be the same or different;

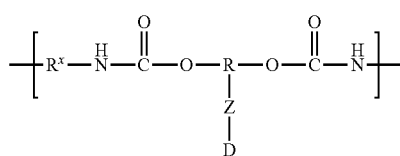

where R, Z and D are as herein defined and $R^x$ is an optionally substituted alkyl, aryl or alkylaryl group, wherein for each repeat unit of the polyurethane each R, Z, D and $R^x$ may be the same or different;

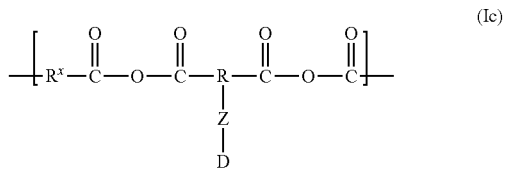

where R, Z and D are as herein defined and $R^x$ is an optionally substituted alkyl, aryl or alkylaryl group, wherein for each repeat unit of the polyurethane each R, Z, D and $R^x$ may be the same or different.

Those skilled in the art will appreciate that the respective ester, carbamate and anhydride moieties in general formulae (Ia), (Ib) and (Ic) are examples of the X and Y biodegradable moieties defined in general formula (I).

In one aspect, the invention provides a biodegradable polymer-bioactive moiety conjugate comprising as part of its polymer backbone a plurality of moieties of general formula (Id):

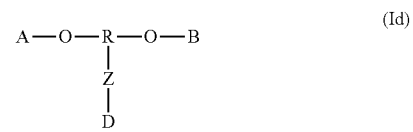

wherein:
A and B, which may be the same or different, represent the remainder of the polymer backbone and are selected from a copolymer of polyurethane and polyester;
R represents a linear or branched optionally substituted hydrocarbon;
Z is a linking group; and
D is a releasable bioactive moiety.

In some embodiments, the O atoms in the —O—R(ZD)-O— shown in general formula (Id) may each independently form part of an ester or urethane moiety as illustrated below where O* represents the O atom in the —O—R(ZD)-O— moiety:

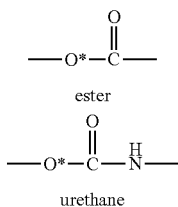

In one embodiment, the O atoms in the —O—R(ZD)-O— each independently form part of an ester or urethane moiety.

In some embodiments, A and/or B may be a polyester. In that case, the monomeric units that are polymerised to form the polyester, typically a diacid and a diol, will each be coupled via a biodegradable ester moiety. A and/or B may also be a polyurethane. In that case, the monomeric units that are polymerised to form the polyurethane, typically a diisocyanate and a diol, will each be coupled via a biodegradable urethane moiety. A and/or B may also be a poly(urethane-ester) formed by polymerising a diisocyanate with a polyester macro-monomer or macromer. In that case, the polyester macromer will be formed from monomeric units that are coupled via a biodegradable moiety (as discussed above), and the polymerisation of it with the diisocyanate will give rise to the poly(urethane-ester) having monomeric units that are all coupled via a biodegradable urethane or ester moiety. A and/or B may also be a poly(ester-urethane) formed by polymerising an isocyanate terminated polyurethane macro-monomer or macromer with an ester containing monomer, for example, an ester linked dimer of hydroxy acids. In that case, the polyurethane macromer will be formed from monomeric units that are coupled via a biodegradable moiety (as discussed above), and the polymerisation of it with the ester monomer give rise to the poly(ester-urethane) having monomeric units that are all coupled via a biodegradable urethane or ester moiety.

The biodegradable polymer in accordance with the invention may form part of or be formed into an article or device per se or can be presented as a coating on an existing article or device.

The biodegradable polymer provides an effective and efficient means for delivering bioactive moieties to a subject.

In another aspect, the invention provides a method of delivering a bioactive moiety to a subject, the method comprising administering to the subject a biodegradable polymer in accordance with the invention.

Through the bioactive moiety release function of the biodegradable polymers, the polymers can also advantageously function as or form part of a sustained bioactive moiety delivery system.

In further aspect, the invention therefore provides a sustained bioactive moiety delivery system, the system comprising a biodegradable polymer in accordance with the invention.

In one embodiment of the invention the releasable bioactive moieties are covalently bonded to the polymer backbone via one or more spacer moieties.

In a further embodiment of the invention the biodegradable polymers have a content of releasable bioactive moieties relative to total polymer of at least 10% by weight, preferably at least 20% by weight, more preferably at least 30% by weight.

In a yet further embodiment of the invention the biodegradable polymers contain two or more different releasable bioactive moieties.

In an even yet further embodiment of the invention the releasable bioactive moieties are capable of being released from the polymer backbone such that they are unencumbered by excess molecular fragments.

In a preferred form of any one of the foregoing embodiments the release of bioactive moieties from the polymer backbone is substantially complete prior to significant breakdown of the polymer backbone.

In a further preferred form of any one of the foregoing embodiments the polymer backbone is substantially degradable to its constituent monomers under in vivo conditions.

In an even further preferred form of any one of the foregoing embodiments the bioactive moiety is a drug moiety.

The invention also provides a biodegradable polymer-bioactive moiety conjugate prepared by polymerising a monomer-bioactive moiety conjugate of formula (II):

(II)

where:
X' and Y' are each hydroxyl;
R represents a linear or branched optionally substituted hydrocarbon;
Z is a spacer moiety; and
D is a releasable bioactive moiety;
with a polyisocyanate and at least one selected from the group consisting of a polyacid, a polyester and a polyester polyol.

In one embodiment, the monomer-bioactive moiety conjugate of formula (II) polymerises with a polyisocyanate and a polyester polyol.

Suitable polyisocyanates may be selected from the group consisting of m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4'diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, polymethylene polyphenhyl polyisocyanates and alkyl esters of lysine diisocyanate (preferably ethyl ester of lysine diisocyanate), and combinations thereof. Preferred polyisocyanates include 1,6-hexamethylene diisocyanate and alkyl esters of lysine diisocyanate, preferably ethyl ester of lysine diisocyanate.

Suitable polyacids may be selected from the group consisting of oxalic acid, fumaric acid, maleic acid, succinic acid, glutaric acid, adipic acid, pimelic acid, suberic acid, azelaic acid, sebacic acid, phthalic acid, dodecanediacid, isophthalic acid, terephthalic acid, dodecylsuccinic acid, napthalene-2,6-dicarboxylic acid, naphthalene-2,7-dicarboxylic acid, cyclohexane dicarboxylic acid, itaconic acid, malonic acid, and mesaconic acid. Preferred polyacids include maleic acid and succinic acid.

Suitable polyester polyols may be selected from the group consisting of polycaprolactone diol (PCLD), poly(DL lactide) (DLLA) and poly(lactic acid-co-glycolic acid) (PLGA), and combinations thereof.

The invention also provides a method for preparing a biodegradable polymer according to the invention, said method comprising the step of polymerising a monomer-bioactive moiety conjugate of formula (II):

(II)

where:
X' and Y' are each independently functional groups that (a) are capable of undergoing polymerisation with monomer having compatible chemical functionality, and (b) react with the compatible chemical functionality to afford a biodegradable moiety;
R represents a linear or branched optionally substituted hydrocarbon;
Z is a spacer moiety; and
D is a releasable bioactive moiety;
with at least one monomer comprising compatible chemical functionality.

In a further aspect there is provided a method for preparing the biodegradable polymer of the present invention by providing at least one first monomer comprising at least one releasable bioactive moiety and at least one polymerisable moiety; optionally providing at least one second monomer comprising at least one polymerisable moiety reactive with at least one polymerisable moiety of said first monomer; polymerising said first monomer and optionally said second monomer optionally in the presence of one or more spacer moieties comprising two or more functionalities under conditions which are substantially non-interfering to the therapeutic efficacy of the bioactive moieties.

In another aspect, the invention also provides a process for preparing a biodegradable polymer-bioactive moiety conjugate comprising as part of its polymer backbone a plurality of moieties of general formula (Id):

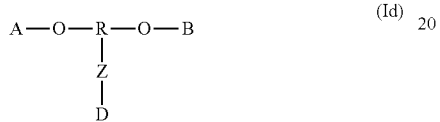

wherein:
A and B, which may be the same or different, represent the remainder of the polymer backbone and are selected from a copolymer of polyurethane and polyester;
R represents a linear or branched optionally substituted hydrocarbon;
Z is a linking group; and
D is a releasable bioactive moiety;
said process comprising the step of polymerising a monomer-bioactive moiety conjugate of formula (IIa):

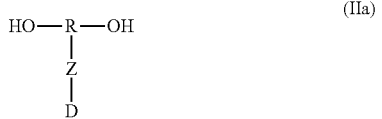

wherein:
R, Z and D are as defined above;
with at least one other monomer comprising compatible chemical functionality.

There is yet further provided a use of the biodegradable polymers of the invention in the preparation of an implantable scaffold, stent or a biomedical coating or dressing or an adhesive.

There is even yet further provided a method of using the biodegradable polymer of the invention to deliver a bioactive moiety, preferably a drug moiety.

The present invention also provides a monomer-bioactive moiety conjugate comprising: a) one or more releasable bioactive moieties; b) two or more polymerisable moieties; wherein one or more of the releasable bioactive moieties are capable of being released from the monomer before or after polymerisation under conditions which are non-interfering to the therapeutic efficacy of the bioactive moieties.

The monomer-bioactive moiety conjugate in accordance with the invention may also be defined in terms a molecular structure.

In another aspect, the invention therefore provides a monomer-bioactive moiety conjugate that is suitable for use in preparing a biodegradable polymer-bioactive moiety conjugate, the monomer-bioactive moiety conjugate having a structure of general formula (II):

where:
X' and Y' are each independently functional groups that (a) are capable of undergoing polymerisation with monomer having compatible chemical functionality so as to form a biodegradable polymer, and (b) react with the compatible chemical functionality to afford a biodegradable moiety;
R represents a linear or branched optionally substituted hydrocarbon;
Z is a spacer moiety; and
D is a releasable bioactive moiety.

In one embodiment, the two or more polymerisable moieties of the monomer-bioactive moiety conjugate (e.g. X' and Y' of general formula (II)) may each be independently selected from hydroxyl, amine, carboxylic acid, isocyanate, and carboxylic acid halide.

In another aspect, the invention provides a monomer-bioactive moiety conjugate that is suitable for use in preparing a biodegradable polymer-bioactive moiety conjugate, the monomer-bioactive moiety conjugate having a structure of general formula (IIa):

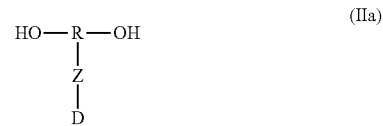

wherein:
R represents a linear or branched optionally substituted hydrocarbon;
Z is a linking group; and
D is a releasable bioactive moiety.

The monomer-bioactive moiety conjugates of the invention have been found to be particularly versatile and can advantageously be polymerised with one or more monomers using techniques well known in the art.

In another aspect the invention provides a process for preparing a monomer-bioactive moiety conjugate that is suitable for use in preparing a biodegradable polymer-bioactive moiety conjugate, the monomer-bioactive moiety conjugate having a structure of general formula (IIa):

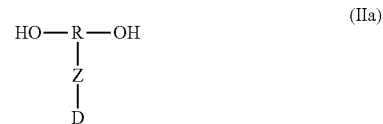

wherein:
R represents a linear or branched optionally substituted hydrocarbon;
Z is a linking group; and
D is a releasable bioactive moiety, said process comprising covalently coupling a linking precursor group Z' in a compound of formula (VI):

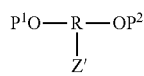
$$P^1O-R-OP^2$$
$$|$$
$$Z'$$
(VI)

wherein:
P¹ and P² are each independently H, a protecting group, or P¹ and P² together form a protecting group; and
R is as defined above,
with a group selected from D or D-Z",
wherein:
D is a bioactive moiety in protected or unprotected form or prodrug thereof; and
Z" is a linking precursor group,
wherein the coupling of Z' with D, or the coupling of Z' with Z" in the group D-Z", forms the

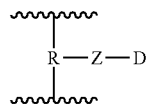
$$R-Z-D$$

moiety in the conjugate of formula (IIa),
and where P¹ and/or P² are protecting groups said process further comprises the step of removing the protecting group or groups.

Z' and Z" (when present) are each linking precursor groups which afford the linking group Z in the monomer-bioactive moiety conjugate of formula (IIa).

In some embodiments, Z' is a moiety comprising a functional group such as a carboxylic acid, acid halide, primary amino, secondary amino, hydroxy group, thiol group, phosphate group or sulphate group that couples to D or couples to Z" in the group D-Z".

In some embodiments, Z" is a moiety comprising a functional group such as a carboxylic acid, acid halide, primary amino, secondary amino, hydroxy group, thiol group, phosphate group or sulphate group that couples to When preparing monomers of general formula (IIa), it may also be desirable to modify the bioactive moiety (D) so as to facilitate its conjugation with compounds of formula (VI). For example, where Z' in formula (VI) comprises a hydroxy group, ester formation through reaction of this hydroxy group with a carboxylic acid group in D can in some cases prove difficult. Under these circumstances, ester formation may be facilitated by first converting the carboxylic acid group in D into an acid halide (e.g. acid chloride) group and then reacting the acid halide group with the hydroxy group.

In other embodiments, the bioactive moiety (D) may first undergo reaction with an appropriate reagent to form the conjugate D-Z". For example, reaction under appropriate conditions of a carboxylic acid functionality on D with a diol, such as 1,6-hexanediol, affords D-Z" where Z" is a linking precursor group derived from 1,6-hexanediol. Subsequent coupling of the remaining free alcohol from 1,6-hexanediol with a functional group on Z', such as an acid halide, affords a monomer of formula (IIa) comprising a linking group (Z) formed from the linking precursor groups Z' and Z".

The skilled worker will be familiar with techniques that may be used to promote reactions between functional groups of complementary reactivity, such as between a carboxylic acid and a hydroxy group. For example, coupling agents such as those mentioned in Tetrahedron Volume 60, Issue 11, 8 Mar. 2004, pages 2447-2467, could be employed (see further detail below).

Further aspects of the invention appear below in the detailed description of the invention.

BRIEF DESCRIPTION OF THE DRAWINGS

Preferred embodiments of the invention will herein be illustrated by way of example only with reference to the accompanying drawings in which.

DETAILED DESCRIPTION OF THE INVENTION

Figure 1:
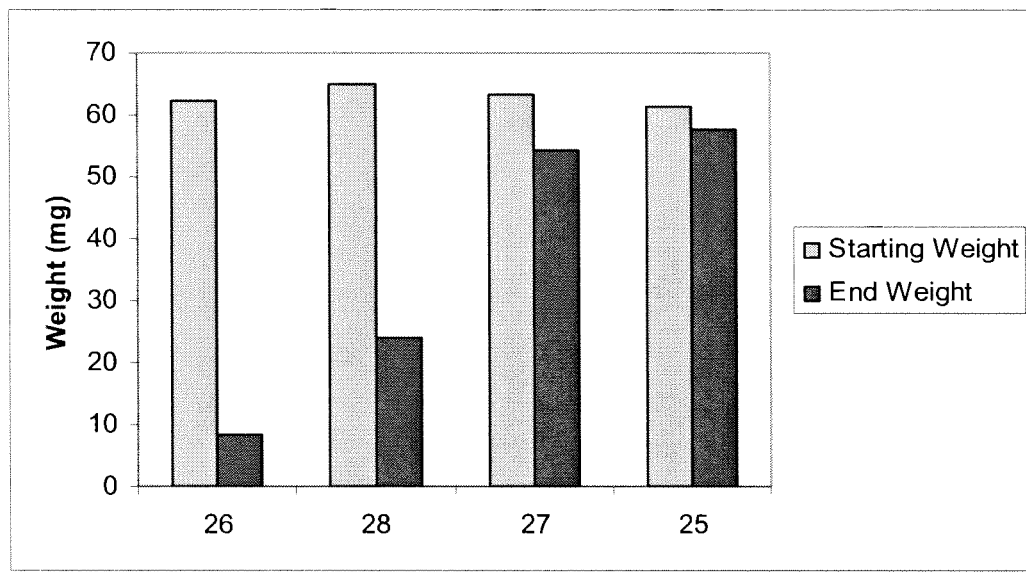
FIG. 1 illustrates weight loss of biodegradable polymers after incubation in physiological conditions at 37° C. demonstrating bioerosion.

The terms "labile" and "releasable" may be used herein synonymously.

Polymers having bioactive moieties covalently attached thereto are often referred to in the art as "polymer-bioactive moiety conjugates". It may therefore be convenient to refer to a biodegradable polymer of the invention as biodegradable polymer-bioactive moiety conjugate or simply as a conjugate.

A biodegradable polymer of the invention may also be described as being a "functionalised" biodegradable polymer by virtue of the bioactive moieties being covalently attached to or "functionalising" the polymer backbone.

An important feature of the conjugates in accordance with the invention is that they are "biodegradable". By being "biodegradable" in the context of the invention is meant that polymer or polymer backbone undergoes with the passage of time substantial degradation under physiological conditions or in a biological environment. In other words, the polymer backbone has a molecular structure that is susceptible to break down (i.e. a reduction in molecular weight) by chemical decomposition in a biological environment (e.g. within a subject or in contact with biological material such as blood, tissue etc), as opposed to physical degradation. Such chemical decomposition will typically be via the hydrolysis of labile or biodegradable moieties that form part of the molecular structure of the backbone. Accordingly, such labile or biodegradable moieties will generally be susceptible to hydrolytic cleavage.

Reference herein to biological material such as "biological tissue" is intended to include cells or tissue in vivo (e.g. cells or tissue of a subject) and in vitro (e.g. cultured cells).

By being biodegradable, the conjugates in accordance with the invention can advantageously be used to release bioactive moieties, for example within a subject, without the need to subsequently remove the remaining conjugate structure from the subject.

An important feature of the biodegradable properties of the polymers is its backbone is formed from monomeric units that are each coupled via a biodegradable moiety. By having such characteristics, the polymers in accordance with the invention can advantageously biodegrade into substantially non-toxic residues.

For example, the —X—R(ZD)-Y— moiety as shown in formula (I) is attached to the remainder of the polymer backbone (represented by A and B) via a biodegradable moieties X and Y, and A and B in their own right are each formed from monomeric units that are coupled via a biodegradable moiety.

As used herein the expression "biodegradable moiety" is intended to mean a moiety that can undergo chemical decomposition under physiological conditions or in a biological environment. Such chemical decomposition will typically be via hydrolysis. In other words, the biodegradable moiety with be susceptible to hydrolytic cleavage. In the context of the present invention, the biodegradable moieties function to link or couple the monomeric units that form the polymer backbone. Accordingly, it will be appreciated that the biodegradable moieties give rise to the biodegradable property of the polymer.

Those skilled in the art will appreciate the type of moieties that are typically susceptible to hydrolytic cleavage under physiological conditions or in a biological environment. Such moieties (represented by X and Y in general formula (I)) may include amide, urethane (carbamate), ester, anhydride, urea and carbonate. The biodegradable polymers in accordance with the invention may include a combination of such moieties.

The terms "carmbamate" and "urethane" referred to herein are used interchangeably. A person skilled in the art would understand that these terms "carmbamate" and "urethane" each refer to a —NC(=O)O— moiety.

In one embodiment, X and Y of all —X—R(ZD)-Y— moieties in the biodegradable polymer are each independently an ester or urethane moiety.

Those skilled in the art will appreciate the type of moieties that are not typically susceptible to hydrolytic cleavage in a biological environment. Such moieties may include carbonyl, siloxane, sulfone, ether, olefin (i.e. C—C, e.g. alkylene, alkenylene and alkynylene) and halogenated olefin.

As noted above, the biodegradable polymer in accordance with the invention will only include monomeric units that are coupled to each other via a biodegradable moiety. By "monomeric units" is meant the building blocks that are polymerised to form the polymer. The monomeric units may in their own right be macro-monomeric units (i.e. monomeric units that are typically low molecular weight polymers and contain monomeric units in their own right—commonly referred to as macromers). Where the monomeric units are macromers, they too must be formed only from monomeric units that are coupled via a biodegradable moiety.

For example, the biodegradable polymer may be a polyester. In that case, the monomeric units that are polymerised to form the polyester, typically a diacid and a diol, will each be coupled via a biodegradable ester moiety. The biodegradable polymer may also be a polyurethane. In that case, the monomeric units that are polymerised to form the polyurethane, typically a diisocyanate and a diol, will each be coupled via a biodegradable urethane moiety. The biodegradable polymer may also be a poly(urethane-ester) formed by polymerising a diisocyanate with a polyester macromer. In that case, the polyester macromer will be formed from monomeric units that are coupled via a biodegradable moiety (as discussed above), and the polymerisation of it with the diisocyanate will give rise to the poly(urethane-ester) having monomeric units that are all coupled via a biodegradable urethane or ester moiety. The biodegradable polymer may also be a poly(esterurethane) formed by polymerising an isocyanate terminated polyurethane macro-monomer or macromer with an ester containing monomer, for example, an ester linked dimer of hydroxy acids such as lactic acid and glyolic acid. In that case, the polyurethane macromer will be formed from monomeric units that are coupled via a biodegradable moiety (as discussed above), and the polymerisation of it with the ester monomer give rise to the poly(ester-urethane) having monomeric units that are all coupled via a biodegradable urethane or ester moiety.

Accordingly, it will be appreciated that the present invention is not intended to embrace the situation where the biodegradable polymer comprises monomeric units that are coupled to each other via a non-biodegradable moiety. For example, the biodegradable polymer can not be a polyether. The biodegradable polymer also can not be a polymer comprising a polyether such as a poly(urethane-ether) or poly (ester-ether) formed by polymerising a diisocyanate and diacid, respectively, with a polyether macromer (e.g. polyalkyleneglycols such as polyethyeneglycol and polypropyleneglycol). In that case, the polyether macromer will be formed from monomeric units (e.g. —(OR)n-) that are coupled via a non-biodegradable moiety (i.e. an ether), and the polymerisation of it with the diisocyanate or diacid will give rise to the poly(urethane-ether) or poly(ester-ether), respectively, that has monomeric units coupled via non-biodegradable moieties.

The biodegradable characteristics of the conjugates in accordance with the invention advantageously enable its polymer backbone to degrade into substantially non-toxic residues. This is in contrast with polymer-bioactive moiety conjugates that comprise within their polymer backbone a non-biodegradable polymer segment such as a polyether or polyvinyl that may give rise to toxic residues. For example, some polyethers are known to be toxic to humans and animals.

Furthermore, low molecular weight diols such as $C_{2-10}$, $C_{2-6}$ or $C_2$ diols (e.g. ethylene glycol) can also be toxic to humans and animals. Low molecular weight diols are commonly used as comonomers or chain extenders in the manufacture of polymers such polyurethanes and polyesters. If such diols are used in preparing the biodegradable polymers of the invention they can subsequently be liberated upon its biodegradation. Accordingly, it can be desirable to limit their use in the biodegradable polymers of the invention. In contrast, higher alcohols such as triols are typically less toxic to humans and animals.

In one embodiment, the biodegradable polymers of the invention comprise polymerised residues of a diol and less than 25 mol %, less than 10 mol %, or less than 5 mol % of those polymerised residues are derived from a low molecular weight diol ($C_{2-10}$, $C_{2-6}$ or $C_2$ diol).

In a further embodiment, the biodegradable polymers of the invention comprise substantially no polymerised residues of a low molecular weight diol ($C_{2-10}$, $C_{2-6}$ or $C_2$ diol).

In still a further embodiment, where the biodegradable polymers of the invention are prepared using diol monomer, less than 25 mol %, less than 10 mol %, or less than 5 mol % of that monomer comprises a low molecular weight diol ($C_{2-10}$, $C_{2-6}$ or $C_2$ diol).

In yet a further embodiment, where the biodegradable polymers of the invention are prepared using diol monomer, that monomer comprises substantially no low molecular weight diol ($C_{2-10}$, $C_{2-6}$ or $C_2$ diol).

The mol % diol/diol residue values referred to herein are those relative to the total moles of diol/diol residue.

In addition to the polymer backbone of the conjugates being biodegradable, it has covalently attached to it in pendant form a plurality of releasable bioactive moieties.

By the bioactive moieties being in "pendant form" is meant that they do not directly form part of the polymer backbone and as such can be released without causing a reduction in the chain length of the polymer backbone. This is more clearly illustrated by general formula (I).

By the bioactive moieties being "releasable", "labile", or "capable of being released" is meant that they can be covalently decoupled or cleaved from the polymer backbone so as to present in a biologically active form. In the context of general formulae I and II above, the moiety will therefore be capable of being released or cleaved from the Z group to afford D per se. Release of the moieties will generally be promoted by the conjugates being exposed to physiological conditions or a biological environment.

The ability of the bioactive moieties to be releasable will generally be as result of them being coupled in pendant form via a biodegradable moiety either directly or through a spacer moiety to the polymer backbone. Hydrolytic cleavage of the biodegradable moiety as herein described therefore will promote release of the bioactive moiety. Further detail in relation to this is discussed below.

The biodegradable polymers in accordance with the invention can advantageously be prepared such that they are suitable for administration to a subject (i.e. suitable for in vivo applications).

According to one embodiment there is provided a method of delivering a bioactive moiety to a subject, the method comprising administering to the subject a biodegradable polymer in accordance with the invention.

By the biodegradable polymer being "suitable" for administration to a subject is meant that administration of the conjugate to a subject will not result in unacceptable toxicity, including allergenic responses and disease states.

By the term "subject" is meant either an animal or human subject. By "animal" is meant primates, livestock animals (including cows, horses, sheep, pigs and goats), companion animals (including dogs, cats, rabbits and guinea pigs), and captive wild animals (including those commonly found in a zoo environment). Laboratory animals such as rabbits, mice, rats, guinea pigs and hamsters are also contemplated as they may provide a convenient test system. Generally, the subject will be a human subject.

By "administration" of the conjugate to a subject is meant that the composition is transferred to the subject such that the bioactive agent will be released. Provided the bioactive agent can be released, there is no particular limitation on the mode of administration, but this will generally be by way of oral, parenteral (including subcutaneous, intradermal, intramuscular, intravenous, intrathecal, and intraspinal), inhalation (including nebulisation), buccal, pulmonary, aural, ocular, nasal, topical, rectal and vaginal modes.

The biodegradable polymers may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Suitable pharmacologically acceptable carriers are described in Martin, Remington's Pharmaceutical Sciences, 18th Ed., Mack Publishing Co., Easton, Pa., (1990), and include, but are not limited to, liquids that may be sterilised such as water and oils, including those of petroleum, animal, vegetable or synthetic origin, such as peanut oil, soya bean oil, mineral oil, sesame oil, and the like.

The biodegradable polymers may also form part of or be formed into an article or device, or be applied as a coating on an article or device, and implanted in a subject. By being "implanted" is meant that the article or device is totally or partly introduced medically into a subjects body, or by medical intervention into a natural orifice of a subject, and which is intended to remain there after the procedure.

Suitable dosage amounts of the bioactive moiety and dosing regimens of the biodegradable polymers can be determined by a physician and may depend on the particular condition being treated, the rate of release of the moiety form the polymer backbone, the severity of the condition as well the general age, health and weight of the subject.

Dosing may occur at intervals of minutes, hours, days, weeks, months or years or continuously over any one of these periods. Suitable dosages of the bioactive moiety per se (i.e. that which is to be release from the polymer backbone within a given time frame) may lie within the range of about 0.1 mg per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The biodegradable polymers in accordance with the invention may be administered in a single dose or a series of doses.

Dosage forms adapted for administration by the above modes may also be formulated with the biodegradable polymer as one of the components of the dose formulation. In the case of ocular, aural or nasal administration the biodegradable polymer may be a component of a drop, cream or ointment or take the form of an implant, ointment or gel. In the case of oral administration the biodegradable polymer could take the form of or be a component in a tablet, capsule or liquid. In the case of topical administration the biodegradable polymer could take the form of or be a component in a cream, ointment, gel or liquid (e.g. eye drop). Parenteral administration would involve the biodegradable polymer to be part of or take the form of an injectable product or implantable device (e.g. coating on a pacemaker) that can be administered subcutaneously, intramuscularly, intravenously or by direct surgical placement within the body.

The form of the biodegradable polymer may be adjusted to be suited to the required application such as a coating, film, pellet, capsule, fibres, laminate, foam etc. The difference in the form of the biodegradable polymer provides a means to alter the release profile of the bioactive moiety. For example the amount of polymer and bioactive moiety may be the same in two different structures e.g. (a) polymer film, and (b) woven multifilament mat. The differences in the surface area to volume, rates of hydration and diffusion paths from the different physical structures can result in different rates of bioactive moiety release from essentially the same polymer.

The adjustment of the form of the polymer to suit the application and further to adjust the form to further control the bioactive moiety release profile provide an additional advantage over purely compositional and polymer structural means to control the release profile of the bioactive moiety.

Some of the compositional/structural means to control the release of the bioactive moiety include: controlling the loading of the bioactive; composition of the other comonomers to adjust criteria such as hydrophobicity, flexibility, susceptibility to degradation, ability of the fragments to autocatalyse the polymer degradation, thermal stability of the polymer, mouldability, polymer solubility to assist casting etc.

Additionally, the ability to produce the biodegradable polymers into a range of forms provide a means to produce three dimensional structures that can be beneficial is providing structural integrity to their application as well as providing a means to control cell growth by control of the placement of the conjugate in structures to allow release of the bioactive moiety at specific places (e.g. fibre coating or fibres in a stent to prevent or control restinosis) Other examples include the ability of the structures to be formed into porous three dimensional structures to control cell phenotype as well as the filter or limit different types of cell bodily fluid ingress.

The biodegradable polymers in accordance with the invention may also be used in in vitro applications such as assays. Such in vitro applications could involve the use of the biodegradable polymers as a coating of a reaction chamber that would have an affect on chamber constituents (e.g. encourage cell growth, discourage growth of contaminating organisms, etc) or as a component within the assay to provide a source of the bioactive moiety (e.g. as an antigen for an ELIZA test).

The use of the biodegradable polymers for in vitro applications could allow the use of the formed polymer to provide a host for bio-signals, essential additives drugs etc for the interaction controlled growth, cell segregation, controlled cell differentiation etc of cells/tissue components etc.

The formed biodegradable polymer could be made into a structure that is compatible with cell culture ware or in vitro devices used to act as indicators etc of certain conditions. The forms of the conjugate could range from simple pellets or films through to multilayer films, fibrous knitted, woven or electrospun structures, printed, spun cast, deposited or cast structures through to foams or composite type structures having multiple forms or components.

The expression "bioactive moiety" (also represented as "D" in certain formulae herein) is used to define any substance that is of medical or veterinary therapeutic, prophylactic or diagnostic utility capable of forming a conjugate in accordance with the invention. For example a bioactive moiety may be a drug or therapeutically active agent, including pharmacologically active agents (e.g. receptor binding agonist or antagonists, cytotoxic agents), pharmacologically inactive agents (e.g. antibiotics) and prodrugs thereof. The bioactive moiety will generally be a substance (e.g. pharmaceutical substance) for therapeutic use whose application (or one or more applications) involves: a chemical interaction, or physicochemical interaction, with a subject's physiological system; or an action on an infectious agent, or on a toxin or other poison, in subject's body; or with biological material such as cells in vitro.

As used herein, a "therapeutic agent" refers to a bioactive moiety that, when administered to a subject, will cure, or at least relieve to some extent, one or more symptoms of, a disease or disorder.

As used herein, a "prophylactic agent" refers to a bioactive moiety that, when administered to a subject either prevents the occurrence of a disease or disorder or, if administered subsequent to a therapeutic agent, prevents or retards the recurrence of the disease or disorder.

Upon being released, the bioactive moiety will either be bioactive or will be converted in vivo or in vitro to a bioactive moiety (e.g. as in the case of a prodrug). Despite the bioactive moiety being releasable from the monomer of formula II, it will be appreciated that the intention of the present invention is for the moiety to be released after the monomer has been polymerised to form polymer.

The bioactive moiety may be released from the biodegradable polymer such that it provides for a sustained bioactive delivery system. Such a delivery system may in its simplest form be the polymer provided in a desired shape, for example a pellet or more intricate shape. To promote surface area contact of the polymer under physiological conditions or with a biological environment, it may also be provided in the form of a foamed product or a coating on substrate.

By "sustained bioactive moiety delivery" is meant that the bioactive moiety is released from the biodegradable polymer over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

In order for the bioactive moiety (also denoted by D in certain formulae herein) to be released, the covalent bond that (a) directly couples the moiety to the polymer backbone, or (b) directly couples the moiety to a spacer moiety which itself is attached to the polymer backbone; (e.g. the covalent bond between D and the Z group in formula (I)), will of course need to be cleaved. For convenience, this covalent bond may be referred to as the "coupling" covalent bond.

In one embodiment the coupling covalent bond is not a carbon-carbon bond. In such an embodiment, the coupling covalent bond will generally form part of a functional group selected from: esters; amides; anhydrides; imides; carbonates; peroxides; peroxyesters; phosphates; thioesters; sulfates; disulfides; carbamates; ethers; siloxanes; azo; orthoesters; phosphonates; peroxy; and boronate esters. Of these functional groups, anhydrides, esters, imides, carbonates, carbamates, and boronate esters are preferred.

Cleavage of the coupling covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ester bond may be hydrolytically cleaved to produce a carboxylic acid and an alcohol, and an amide bond may be hydrolytically cleaved to produce a carboxylic acid and an amine. Those skilled in the art will appreciate that such cleavage amounts to the hydrolytic cleavage of the biodegradable moieties discussed herein. Accordingly, the bioactive moiety (D) may also be described as being coupled to the polymer backbone, optionally through a spacer moiety (Z) via a biodegradable moiety.

As indicated above, on being released the bioactive moiety may be in the form of a prodrug. As used herein, the term "prodrug" refers to a derivative of a bioactive moiety, wherein the derivative may have little or none of the activity of the bioactive moiety per se yet is capable of being converted in vivo or in vitro into a bioactive moiety. An example of such derivatisation is the acetylation of one or more hydroxyl groups on a bioactive moiety, such that subsequent to being released in vivo the released prodrug is deactylated to produce the bioactive moiety.

The terms "spacer", "spacer group" or "spacer moiety" refer to an atom or any straight chain or branched, symmetric or asymmetric compound capable of linking or coupling the bioactive moiety to a monomer or a polymer backbone.

For example, in the structures of formulae (I), (Ia), (Ib), (Ic), (Id), (II), and (IIa), the bioactive moiety (D) is coupled to R through a spacer moiety denoted by Z. Thus, "spacer", "spacer group" or "spacer moiety" refers to a substituent which is generally divalent and that couples D to R. As outlined above, the covalent bond between the spacer moiety and the bioactive moiety is cleavable so that the bioactive moiety is releasable.

Examples of suitable spacer moieties include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkyl acyloxy, alkyl oxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkyl alkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —CH$_2$— group in any alkyl chain may be replaced by a divalent group independently selected from —O—, —OP(O)$_2$—, —OP(O)$_2$O—, —S—, —S(O)—, —S(O)$_2$O—, —OS(O)$_2$O—, —N═N—, —OSi(OR$^a$)$_2$O—, —Si(OR$^a$)$_2$O—, —OB(OR$^a$)O—, —B(OR$^a$)O—, —NR$^a$—, —C(O)—, —C(O)O—, —OC(O)O—, —OC(O)NR$^a$— and —C(O)NR$^a$—, where the or each R$^a$ may be independently selected from hydrogen, alkyl, alkenyl, alkynyl, aryl, carbocyclyl, heteroaryl, heterocyclyl, arylalkyl, and acyl. The or each R$^a$ may also be independently selected from hydrogen, C$_{1-18}$alkyl, C$_{1-18}$alkenyl, C$_{1-18}$alkynyl, C$_{6-18}$aryl, C$_{3-18}$carbocyclyl, C$_{3-18}$heteroaryl, C$_{3-18}$heterocyclyl, and C$_{7-18}$arylalkyl.

The spacer moiety may be branched. In some embodiments where the spacer moiety is branched, two or more releasable bioactive moiety may be appended to the spacer moiety.

In the lists above defining groups (generally divalent) from which the or each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A] [group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

The biodegradable polymer of present invention can be readily prepared using monomer—bioactive moiety conjugates, such as those of general formula (II) or (IIa). Such monomers can themselves be prepared using commonly available reagents. Examples of such reagents that may be used to construct the spacer moiety (e.g. Z) include linear or branched hydrocarbons substituted with two or more reactive functional groups such as alcohols, primary and secondary amines, carboxylic acids and combinations thereof. Examples of such substituted hydrocarbons are diols, diacids, diamines, hydroxyacids, amino acids and amino alcohols. The substituted hydrocarbons may be α,ω-substituted alkylenes or α,ω-substituted (poly)oxycarbonylalkylenes [i.e. α,ω-substituted polyesters]. The skilled person will appreciate that when such α,ω-substituted alkylenes or α,ω-substituted (poly)oxycarbonylalkylenes are used as the linking group, the monomer—bioactive moiety conjugates of formula (II) or (IIa), and polymers produced therefrom, will typically comprise at least two functional groups that may be susceptible to cleavage so as to release the bioactive moiety. In these compounds, it is preferable that the functional group closest to the bioactive moiety is as susceptible to, or more susceptible to, cleavage than the functional group closest to the polymer backbone.

Specific examples of spacer moieties include: —O—; —C(O)—; and optionally substituted: —OC(O)—C$_{1-18}$alkylene-C(O)—; —C(O)O—C$_{1-18}$alkylene-C(O)—; —NR$^a$C(O)—C$_{1-18}$alkylene-C(O)—; C(O)O—C$_{1-18}$alkylene-O—; —O—C$_{1-18}$alkylene-O—; —O—C$_{1-18}$alkylene-NR$^a$—; —OC(O)—C$_{1-18}$alkylene-NR$^a$—; —C(O)—C$_{1-18}$alkylene-NR$^a$—; —OC(O)—C$_{1-18}$alkylene-O—; —C(O)—C$_{1-18}$alkylene-O—; and —C(O)NR$^a$—C$_{1-18}$alkylene-NR$^a$— where R$^a$ is as defined above.

Preferred examples of spacer moieties include: —O—; —C(O)—; and —OC(O)—C$_{1-18}$alkylene-C(O)—, such as —OC(O)—C$_{2-3}$alkylene-C(O)—.

An example of a monomer-bioactive moiety conjugate of formula (II) that comprises a —OC(O)—C$_{1-18}$alkylene-C(O)— spacer moiety (Z) is shown below:

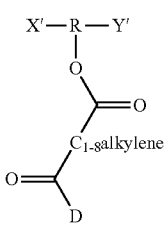

where:
X', Y' R and D are as herein defined.

In one embodiment, X' and Y' are each hydroxyl.

An example of a monomer-bioactive agent conjugate of formula (IIa) that comprises a —OC(O)—$C_{1-18}$alkylene-C(O)— linking group (Z) is shown below:

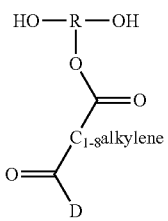

wherein:
R represents a linear or branched optionally substituted hydrocarbon; and
D is a releasable bioactive moiety.

The monomer-bioactive moiety conjugate precursor (i.e. the monomer prior to conjugate addition of the bioactive moiety—herein after conveniently referred to as the precursor monomer) must of course have a means for chemical attachment to the bioactive moiety or to a spacer moiety. The types of functional groups on the precursor suitable for such attachment include hydroxyl, carboxylate, amino, thiol, phosphate or combinations thereof. The precursor may be singly of multiply functionalised with bioactive moieties.

As discussed above, the bioactive moiety must correspondingly have a means for chemical attachment to the precursor monomer or to a spacer moiety. The types of functional groups on the bioactive moiety suitable for attachment include hydroxyl, carboxylate, amino, thiol, phosphate or combinations thereof.

Where a spacer moiety is used, as discussed above it must have at least two functional groups for chemical attachment, one to the bioactive moiety the other to the precursor monomer. Useful spacer moiety precursors (i.e. the spacer moiety prior to being covalently attached to the polymer or bioactive moiety) may include functional groups such as hydroxyl, carboxylate, amino, thiol, phosphate or combinations thereof.

The spacer moieties may be derived from precursors that comprise two or more functional groups which may be the same or different. Examples of precursors from which the spacer moieties may be derived that contain a single type of functional group include dicarboxylic acids (e.g., malonic acid), diols (e.g., propylene glycol), polyols (e.g., glycerol), dithiols (e.g., 1,3-propanedithiol). Examples of precursors from which the spacer moieties may be derived that contain two or more different functional groups include glycolic acid, citric acid, tartaric acid, lactic acid, salicylic acid, lysine, serine, aspartic acid, cysteine, etc. Using such precursors is advantageous when seeking to couple a bioactive moiety to a monomer precursor through the same type of functional group. For example, coupling the carboxylic acid on a bioactive moiety to a carboxylic acid on a monomer precursor can be achieved with a diol or polyol spacer. Conversely, coupling a hydroxyl on a bioactive moiety to a hydroxyl on a monomer precursor can be achieved with a diarboxylic acid (e.g., malonic acid) spacer.

Use of the spacer moieties can provide facile coupling of the bioactive moiety to the R group. In particular, spacer moieties may provide the skilled worker with the ability to couple the bioactive moiety at a sterically hindered position that could not otherwise be achieved by directly coupling the moiety to the R group.

The choice of spacer moieties will determine the spacing of the D from the X' and Y' groups in the monomers of formula (II). In this respect, the use of spacer moieties can provide a means to distance D from these groups. This can facilitate polymerisation of the monomers by reducing steric crowding around the X' and Y' groups.

In forming a monomer of formula (II), prior to conjugation the bioactive moiety (denoted by D) necessarily comprises compatible functionality so as to promote coupling of the bioactive moiety to the monomer through Z.

Examples of such compatible functionalities in D can include:
(i) carboxylic acids, sulfates and phosphates (e.g. for reacting with a spacer precursor moiety comprising a primary amino, secondary amino or hydroxy group to couple the bioactive moiety to the monomer through a nitrogen atom or an oxygen atom containing spacer moiety); and
(ii) carboxylic acids, hydroxyls, amines (primary and secondary) thiols and phosphates (e.g. for reacting with a spacer precursor moiety comprising a carboxylic acid or acid halide group to couple the bioactive moiety to monomer through a carbonyl group containing spacer moiety).

Those skilled in the art will appreciate that the process of preparing the monomer—bioactive moiety conjugate will typically result in expulsion of a small molecule such as water or hydrogen halide (e.g. HCl). For example, the formation of an ester bond through reaction of a carboxylic acid group with a hydroxy group liberates a water molecule.

In some embodiments, the bioactive moiety comprises a carboxylic acid, hydroxyl group, thiol group, amine group, or phosphate group, or combinations thereof for conjugate coupling. When conjugated through such groups, a part or the whole of the Z group can form part of an ester, an amide, an anhydride, an azo, an imide, a carbonate, a peroxyester, a thioester, a carbamate, a boronate ester, a sulfate or a phosphate linkage group. The skilled worker will recognise that each of these linkage groups comprises a covalent bond that is capable of being cleaved (for example hydrolytically, enzymatically and/or by a radical mechanism). Generally, such spacer groups will comprise a covalent bond that is capable of being cleaved hydrolytically so as to release the bioactive moiety.

Where a given bioactive moiety comprises more than one compatible functional group capable of conjugate coupling, the skilled worker may routinely adopt an appropriate protecting group strategy so that the bioactive moiety couples to the monomer in a preselected fashion. Protection group chemistry, and strategy, is well-known in the art in, for example, T. W. Greene and P. G. M. Wuts in "Protective Groups in Organic Chemistry", John Wiley and Sons, 1991. For example, where a bioactive moiety comprises a primary alcohol and a primary amine, the skilled worker may protect the primary amine prior to coupling the bioactive moiety so that the bioactive moiety couples through an ester moiety rather than an amide moiety. In another example a primary alcohol may be protected selectively over a secondary alcohol, so that the bioactive moiety may be coupled through an ester moiety derived from the secondary alcohol. Such protecting groups may or may not be removed following coupling. For example, the protecting group may be an acetyl group, and the acetylated amine or alcohol may undergo cleavage in vivo to return the unprotected amine or alcohol.

Provided that a suitable conjugate can be formed, there is no particular limitation on the type of bioactive moiety that may be used in accordance with the invention. The bioactive moiety may be exemplified by 5-alpha-reductase inhibitors, amebicides, aminosalicylates, anaesthetics (general and local), analgesics, angiotensin inhibitors, anorexiants, antacid agents, anti-angiogenic agents, antianginal agents, antiarrhythmic agents, antiarthritic agents, antibiotics, antibacterial agents, antibodies, anticoagulants, anticonvulsants, antidepressants, antiepileptic agents, antifungals, anthelmintics, antihistamines, antihypertensives, antihyperlipidemic agents, antiinfectives, antiinflammatories, antiemetics, antimalarial, antimetabolites, antimigraine, antimitotics, antiparasitic agents, antiparkinson agents, antipsychotics, antiprotozoals, antitussives, antiulcer agents, antivirals, anxiolytics, bronchodilators, decongestants and expectorants, cancer therapy and related pharmaceuticals, cardiovascular pharmaceuticals, central nervous system pharmaceuticals, benzopidazepines, beta-adrenergic blocking agents, bisphosphonates, calcium channel blockers, carbonic anhydrase inhibitors, chemokine receptor antagonist, coumarins and indadiones, cox-2 inhibitors, contraceptives, cytotoxics, diuretics, diabetes therapies, growth hormones, fertility pharmaceuticals, hematinics, glucose modifying agents, growth promoters, H2 antagonists, heparin and heparin antagonists, hormone replacement therapies, hemostatics, immunosuppressants, immunostimulants, inotropic agents, interferons, hormones and analogs, impotence agents, kinase inhibitors, laxatives, leukotriene modifiers, macrolides, mast cell stabilizers, muscle relaxants/stimulants, midrates, neuromuscular blocking agents, obesity therapeutics, ophthalmic pharmaceuticals, osteoporosis drugs, pain therapeutics (including paracetamol, opiates, nonsteroidal antinflammatory agents, tramadol), peptides and polypeptides, peripheral vasodilators, platelet inhibitors/stimulating agents, prolactin inhibitors, protease inhibitors, protein therapeutics, proton pump inhibitors, radiopharmaceuticals, respiratory pharmaceuticals, sedatives, spermicides, steroids (including androgens, anabolic and adrenal cortical), smoking cessation agents, statins, stimulants and tranquilizers, sulphonamides, thyroid drugs, urinary acidifiers/alkalinisers, and vasodilators.

The bioactive moiety may include any drug or therapeutically active agent, including pharmacologically active agents (e.g., receptor binding agonist or antagonists, cytotoxic agents) and pharmacologically inactive agents (e.g., antibiotics).

Specific examples of bioactive moieties that can be used in the present invention are listed below in categories according to their functional groups that may be used in conjugate formation. This list is in no way limiting the scope of drugs covered in this invention, but given as representative examples. All the amino—(including amide-NH and sulfonamide-NH, carbamate-NH, sulfamate-NH, hydrazone-NH, semicarbazone-NH, thiosemicarbazone-NH, urea-NH, phosphoramide-NH and the like), carboxyl- and hydroxyl-(including oxime-OH), containing drugs under various therapeutic categories as listed in Merck Index (13th editions) and other data bases such as prous science's ensemble, integrity, and the like and also all the qualified (i.e., amino-, and/or hydroxyl-, and/or carboxyl-containing) investigational drugs as listed in databases such Merck Index (14th. edition), iddb, ensemble, integrity, and the like, are covered under this invention without any limitation.

Anti-Inflammatory Drugs:

Amino-containing: Ampiroxicam, Bucolome, Celecoxib, Difenpiramide, Mofebutazone, Nimesulide, Paranyline, Parecoxib, Parsalmide, Piketoprofen, Talniflumate, Tenidap, Terofenamate, and Valdecoxib.

Hydroxyl-containing: 21-Acetoxypregnenolone, Alclometasone, Betamethasone, alfa-Bisabolol, Budesonide, Clobetasone, Cyclosporin, Deflazacort, Dexamethasone, Diflorasone, Desonide, Desoximetasone, Diflorasone, Diflucortolone, Difluprednate, Ditazol, Everolimus, Fluazacort, Fludrocortisone, Flumethasone, Fluocinolone, Fluocinonide, Fluocortin Butyl, Fluocortolone, Fluprednidene Acetate, Glucametacin, Halcinonide, Halobetasol Propionate, Halometasone, Halopredone Acetate, Hydrocortisone, Ibuproxam, Loteprednol Etabonate, Mazipredone, Memetasone, Methylprednisolone, Mometasone Furoate, Oxyphenbutazone, Perisoxal, Pimecrolimus, Prednisolone, Prednisone, Rimexolone, Sirolimus, Triamcinolone and Tacrolimus.

Hydroxyl-, and Amino-containing: Bufexamac, Etofenamate, Fepradinol, Ibuproxam, Isoxicam, Lornoxicam, Meloxicam, Oxametacine, Piroxicam, and Tenoxicam.

Carboxyl- and Amino-containing: Aceclofenac, Alminoprofen, Amfenac, 3-Amino-4-hydroxybutyric Acid, Carprofen, Diclofenac, Enfenamic Acid, Etodolac, Flufenamic Acid, Meclofenamic Acid, Mefenamic Acid, Niflumic Acid, and Tolfenamic Acid.

Carboxyl-containing: Acemetacin, Acetamidocaproic Acid, Bendazac, Benoxaprofen, Bermoprofen, Bucloxic Acid, Butibufen, Cinmetacin, Clidanac, Clopirac, Felbinac, Fenbufen, Fenclozic Acid, Fenoprofen, Fentiazac, Flunoxaprofen, Flurbiprofen, Ibuprofen, Indomethacin, Isofezolac, Isoxepac, Ketoprofen, Lonazolac, Loxoprofen, Metiazinic Acid, Mofezolac, Naproxen, Oxaprozin, Pirazolac, Pirprofen, Pranoprofen, Protizinic Acid, Sulindac, Suprofen, Suxibuzone, Tiaprofenic Acid, Tolmetin, and Tropesin. Bermoprofen, Bucloxic Acid, Isoxepac, Ketoprofen, Loxoprofen, and Zaltoprofen.

Carboxyl- and Hydroxyl-containing: Balsalazide, Enoxolone, Fendosal, Olsalazine, Oxaceprol, and Ximoprofen.

Amino-, Carboxyl- and Hydroxyl-containing: 3-Amino-4-hydroxybutyric Acid, Mesalamine, and Sulfasalazine.

Analgesic and/or Antipyretic Drugs:

Amino-containing: Aminochlorthenoxazin, Aminopropylon, Anileridine, Antrafenine, Benorylate, Benzpiperylon, p-Bromoacetanilide, Butacetin, Carsalam, Difenamizole, Etersalate, Ethenzamide, Ethoxazene, Flipirtine, Isonixin, Nifenazone, Phenacetin, Phenazopyridine, Phenocoll, Phenopyrazone, Piminodine, Piritramide, Propacetamol, Ramifenazone, Piperylone, Salverine, and Tinoridine.

Hydroxyl-containing: Aluminum bis(acetylsalicylate), Benzylmorphine, Buprenorphine, Butorphanol, Chlorobutanol, Ciramadol, Codeine, Desomorphine, Dihydrocodeine, Dihydromorphine, Dihydroxyaluminum acetylsalicylate, Dimepheptanol, Eptazocine, Ethylmorphine, Eugenol, Hydromorphone, Hydroxypethidine, Levorphanol, Meptazinol, Metazocine, Morphine, Nalbuphine, Oxycodone Pentazocine, Phenazocine, Phenoperidine, Phenylsalicylate, Salicin, Tramadol, and Viminol. Hydromorphone, Ketobemidone, Metopon, Oxycodone, and Oxymorphone.

Carboxyl-containing: Acetylsalicylsalicylic acid, Alclofenac, Aspirin, Benoxaprofen, 5-Bromosalicylic acid acetate, Cinchophen, Diacerein, Dipyrocetyl, Fosfosal, Ibufenac, Indoprofen, and Salicysulfuric acid. Clometacin, Ketorolac, and Zomepirac.

Amino- and Hydroxyl-containing: Acetaminophen, Acetaminosalol, Bucetin, Capsaicine, Dezocine, Floctafenine, Glafenine, Isoladol, p-Lactophenetide, Norlevorphanol, Normorphine, Phenylramidol, Salacetamide, and Salicylamide.

Amino- and Carboxyl-containing: Actarit, Bumadizone, Clonixin, and Salicylamide O-acetic acid.

Carboxyl- and Hydroxyl-containing: Diflunisal, Gentisic acid, and Salsalate.

Antihypertensive Drugs:

Amino-containing: Alfuzosin, Benzylhydrochlorothiazide, Bethanidine, Bopindolol, Budralazine, Bunazosin, Ciclosidomine, Clonidine, Clopamide, Cyclopenthiazide, Debrisoquin, Edeserpidine, Diazoxide, Dihydralazine, Doxazosin, Endralazine, Guanabenz, Guanacline, Guanazodine, Guanethidine, Guanochlor, Guanadrel, Guanfacine, Guanoxan, Hydracarbazine, Hydralazine, Hydroflumethiazide, Indapamide, Indoramin, Irbesartan, Ketanserin, Lofexidine, Mebutamate, Mecamylamine, Methyl 4-pridyl ketone thiosemicarbazone, Mibefradil, Minoxidil, Monatepil, Moxonidine, Pheniprazine, Pinacidil, Prazosin, Raubasine, Rescinnamine, Reserpiline, Reserpine, Rilmenidine, Syrosingopine, Tasosartan, Terazosin, Tiamenidine, Todralazine, Tolonidine, Tripamide, and Urapidil.

Hydroxy-containing: Ajmaline, Cicletanine, Levcromakalim, Naftopidil, Phenactropinium chloride, and Protoveratrines.

Carboxyl-containing: Eprosartan, Fosinopril, and Telmisartan, Captopril, and Omapatrilat.

Amino- and Carboxyl-containing: Alacepril, gama-Aminobutyric acid, Benazepril, Candesartan, Carmoxirole, Caronapril, Cilazapril, Delapril, Enalapril, Enalaprilat, Imidapril, Lisinopril, Moexipril, Moveltipril, Perindopril, Quinapril, Ramipril, Saralasin, Spirapril, Temocapril, Trandolapril, and Valsartan.

Amino- and Hydroxyl-containing: Acebutolol, Alprenolol, Amosulalol, Arotinolol, Atenolol, Betaxolol, Bisoprolol, Bosentan, Bucindolol, Bufeniode, Bunitrolol, Bupranolol, Butofilolol, Cadralazine, Celiprolol, Carazolol, Carteolol, Cetamolol, Carvedilol, Epanolol, Indenolol, Nadolol, Dilevalol, Fenoldopam, Guanoxabenz, Labetalol, Losartan, Mepindolol, Metipranolol, Metoprolol, Moprolol, Nebivolol, Olmesartan, Oxprenolol, Penbutolol, Phentolamine, Pildralazine, Pindolol, Propranolol, Rescimetol, Sulfinalol, Talinolol, Tertatolol, Timolol, and Trimazosin.

Amino-, Hydroxyl- and Carboxyl-containing: Methyldopa, and Sampatrilat.

Antibiotics:

All the known amino-, hydroxyl-, and carboxyl-containing antibiotics such as Amoxicillin, Ampicillin, Olivanic acid, Metronidazole, and the like as listed in Merck Index. 13.sup.th edition and other drug databases integrity, ensemble, iddb, and the like. These antibiotics can be used in combination with beta-lactamase inhibitor such as clavulanic acid, penicillinic acid sulfone and the like. The following lists of antibacterial and antifungal agents are given for clarity.

Antibacterial Agents:

Amino-containing: Acedapsone, Acetosulfone sodium, Ambazone, Bacampicillin, Benzylsulfamide, Brodimoprim, Cefcapene pivoxil, Cefpodoxime proxetil, Chloramine-B, Chloramine-T, Capreomycin, Clofazimine, Cyacetacide, Cycloserine, Dapsone, Ethionamide, Furazolium chloride, N2-Formylsulfisomidine, Furonazide, Isoniazid, Lenampicillin, Linezolide, Mafenide, 4'-(Methylsulfamoyl)sulfanilanilide, Morphazinamide, Nifuradene, Nitrofurantoin, Penamecillin, Penethamate hydriodide, Pexiganan, Pivampicillin, Pivcefalexin, Picloxydine, Protionamide, Pyrazinamide, Solasulfone, Subathizone, 4,4'-Sulfinyldianiline, Sulfoxone sodium, 4'-Sulfanilylsulfanilamide, Sulfoniazide, Sulfabenzamide, Sulfacetamide, Sulfachlorpyridazine, Sulfacytine, Sulfadiazine, Sulfadicramide, Sulfadimethoxine, Sulfadoxine, Sulfaethidole, Sulfaguanidine, Sulfaguanole, Sulfalene, Sulfamerazine, Sulfameter, Sulfamethazine, Sulfamethizole, Sulframethomidine, Sulfamethoxazole, Sulfamethoxypyridazine, Sulfamethylthiazole, Sulfametrole, Sulfamidochrysoidine, Sulfamoxole, Sulfanilamide, p-Sulfanilylbenzylamine, Sulfanilylurea, N-Sulfanilyl-3,4-xylamide, Sulfaperine, Sulfaphenazole, Sulfaproxyline, Sulfapyrazine, Sulfasomizole, Sulfasymazine, Sulfathiazole, Sulfathiourea, Sulfisomidine, Sulfisoxazole, Sultamicillin, Sulfatolamide, Talampicillin, Taurolidine, Tetroxoprim, Thiazosulfone, Thiacetazone, Tiocarlide, and Trimethoprim.

Hydroxyl-containing: Azithromycin, Chloroxylenol, Chlorquinadol, Clindamycin, Clofoctol, Cloxyquin, Diathymosulfone, Doxycycline, Glucosulfone sodium, Nifurpirinol, Nifurtoinol, Nitroxoline, Roxarsone, Roxithromycin, Xanthocillin, and Xibomol. Carbomycin, Clarithromycin, Erythromycin, all erythromycin ester derivatives, Oleandomycin, and Telithromycin.

Carboxyl-containing (including sulfate, phosphate and phosphonate-containing): Amdinocillin, Cinoxacin, Difloxacin, Fosfomycin, and Hydnocarpic acid. Fleroxacin, Flumequine, Miloxacin, Nalidixic acid, Ofloxacin, Oxolinic acid, Pefloxacin, Piromidic acid, Prulifloxacin, Rosoxacin, and Rufloxacin.

Amino- and Carboxyl-containing (including sulfate-, sulfonic acid-, phosphate and phosphonate-containing): Acediasulfone, Amphomycin, Ampicillin, Azidocillin, Azlocillin, Aztreonam, Bacitracin, Balofloxacin, Betamipron, Carbenicillin, Carindacillin, Carumonam, Cefaclor, Cefazedone, Cefazolin, Cefclidin, Cefditoren, Cefepime, Cefetamet, Cefixime, Cefinenoxime, Cefinetazole, Cefodizime, Ceforanide, Cefotaxime, Cefotetan, Cefotiam, Cefoxitin, Cefozopran, Cefpimizole, Cefpirome, Cefroxadine, Cefsulodin, Ceftazidime, Cefteram, Ceftezole, Ceftibuten, Ceftizoxime, Ceftriaxone, Cefuroxime, Cefuzonam, Cephacetrile sodium, Cephalexin, Cephaloglycin, Cephaloridine, Cephalosporin C, Cephalothin, Cephapirin sodium, Cephradine, Cilastatin, Ciproflaxacin, Clinafloxacin, Clometocillin, Cyclacillin, Dicloxacillin, Enoxacin, Epicillin, Fenbenicillin, Floxacillin, Hetacillin, Loracarbef, Metampicillin, Methicillin, Mezlocillin, Nafcillin, Noprysulfamide, Opiniazide, Oxacillin, Penicillin(s), Penimepicycline, Phenethicillin, Phthalylsulfacetamide, Phthalylsulfathiazole, Piperacillin, Propicillin, Quinacillin, Succinylsulfathiazole, Succisulfone, Sulbenicillin, Sulfachrysoidine, Sulfanilic acid, Temocillin, Ticarcillin, and Tigemonam. Garenoxacin, Gatifloxacin, Gemifloxacin, Grepafloxacin, Lomefloxacin, Moxifloxacin, Norfloxacin, Pazufloxacin, Pipemidic acid, Sitafloxacin, Sparfloxacin, Tosufloxacin, and Trovafloxacin.

Amino- and Hydroxyl-containing: Amikacin, p-Aminosalicylic acid hydrazide, Arbekacin, Azidamfenicol, Bambermycins, 5-Bromosalicylhydroxamic acid, Butirosin, Clindamycin, Clomocycline, Chloramphenicol, Cloxacillin, Colistin, Demeclocycline, Deoxydihydrostreptomycin, Dibekacin, Dihydrostreptomycin, Dirithromycin, Doxycycline, Enviomycin, Ethambutol, Forimicins, Gentamycin, Glyconiazide, N4-beta-D-Glucosylsulfanilamide, Gramicidin(s), Isepamicin, Kanamycin(s), Lincomycin, Meclocycline, Methacycline, Micronomicin, Neomycin, Netilmicin, Novobiocin, Paromomycin, Phenyl aminosalicylate, Pipacycline, Polymyxin, Primycin, Ramoplanin, Ribostamycin, Rifabutin, Rifalazil, Rifamide, Rifamycin SV, Rifampin, Rifapentine, Rifaximin, Ristocetin, Salinazid, Sancycline, Sisomicin, Streptolydigin, Streptomycin, Streptonicozid, 2-p-Sulfanilylanilinoethanol, Thiamphenicol, Thiostrepton, Tobramycin, Tuberactinomycin, Viomycin, and Virginiamycin. Chlortetracycline, Dalfopristin, Guamecycline, Mikamycin, Minocycline, Oxytetracycline, Pristinamycin, Quinupristin, Rolitetracycline, Spectinomycin, and Trospectomycin.

Hydroxyl- and Carboxyl-containing (including sulfate, phosphate and phosphonate-containing): Fropenem, Nadifloxacin, Biapenem, Fusidic acid, and Merbromin.

Amino-, Hydroxyl-, and Carboxyl-containing (including sulfate, phosphate and phosphonate-containing): p-Aminosalicylic acid, Apicycline, Amoxicillin, Apalcillin, Aspoxicillin, Benzoylpas, Cefadroxil, Cefamandole, Cefatrizine, Cefbuperazone, Cefdinir, Cefminox, Cefonicid, Cefoperazone, Cefoselis, Cefpiramide, Cefprozil, Ertapenem, Flomoxef, Imipenem, Lymecycline, Meropenem, Moxalactam, Negamycin, Panipenem, Ritipenem, Salazosulfadimidine, Sulfaloxic acid, 4-Sulfanilamidosalicylic acid, Teicoplanin, Tyrocidine, and Vancomycin.

Antifungal Agents:
Amino-containing: Chlordantoin, Exalamide, Flucytosine, Loflucarban.

Hydroxy-containing: Chlorphenesin, Ciclopirox, Delmostatin, Filipin, Fluconazole, Fungichromin, Pecilocin, Posaconazole, Ravuconazole, Rubijervine, Siccanin, 2,4,6-Tribromo-m-cresol and Voriconazole.

Carboxyl-containing: Undecylenic acid (10-undecenoic acid), and Propionic acid.

Amino- and Carboxyl-containing: Azaserine.

Amino- and Hydroxyl-containing: Salicylanilide, Acrisorcin (9-Aminoacrindine compound with 4-Hexylresorcinol (1:1)), Anidulafungin, Bromosalicylchloranilide, Buclosamide, Caspofungin, Micafungin, and Tubercidin.

Amino-, Carboxyl- and Hydroxyl-containing: Natamycin, Amphotericin B, Lucensomycin, and Nystatin.

Antiviral Drugs:
Hydroxy-containing: Edoxudine, Floxuridine, Idoxuridine, Kethoxal, Podophyllotoxin, Sorivudine, Stavudine, Trifluridine, and Zidovudine.

Amino-containing: Amantadine, Amidinomycin, Atevirdine, Capravirine, Delavirdine, Efavirenz, Famciclovir, Imiquimod, Lamivudine, Methisazone, Moroxydine, Nevirapine, Oseltamivir, Rimantadine, Stallimycin, mantadine, and Valacyclovir.

Amino- and Hydroxyl-containing: Abacavir, Acyclovir, Adefovir, Amprenavir, Atazanavir, Cidofovir, Didanosine, Dideoxyadenosine, Emtricitabine, Entecavir, Indinavir, Lamivudine, Lopinavir, 5-(methylamino)-2-deoxyuridine (MADU), Nelfinavir, Penciclovir, Resiquimod, Ribavirin, Ritonavir, Saquinavir, Tenofovir, Tipranavir, Valganciclovir, Vidarabine, and Zalcitabine.

Carboxyl- and Hydroxyl-containing: Foscarnet sodium, and Ganciclovir.

Amino-, Carboxyl- and Hydroxyl-containing: Zanamivir.

Antimalarial:
Amino-containing: Chlorguanide, Chloroquine, Chlorproguanil, Cycloguanil, Pamaquine, Plasmocid, Primaquine, Quinocide, and Tafenoquine.

Hydroxyl-containing: Artemisinin alcohol, Bebeerines, Cinchonidine, Cinchonine, Dihydroartemisinin, Halofantrine, Lumefantrine, Quinine and Yingzhaosu A.

Carboxyl-containing: Arteflene and Artesunate.

Amino-, and Hydroxyl-containing: Amodiaquin, Hydroxychloroquine, Mefloquine, and Pyronaridine.

Antineoplastic Drugs:
Hydroxy-containing: Aclacinomycins, Arzoxifene, Batimastat, Broxuridine, Calusterone, Capecitabine, CC-1065, Chromomycins, Diethylstilbestrol, Docetaxel, Doxifluridine, Droloxifene, Dromostanolone, Enocitabine, Epitiostanol, Estramustine, Etanidazole, Etoposide, Fenretinide, Flavopiridol, Formestane, Fosfestrol, Fulvestrant, Gemcitabine, Irinotecan, Melengestrol, Menogaril, Miltefosine, Mitobronitol, Mitolactol, Mopidamol, Nitracrine, Nogalamycin, Nordihydroguaiaretic Acid, Olivomycins, Paclitaxel and other known paclitaxel analogs, Plicamycin, Podophyllotoxin, Retinoic acid (including all trans-retinioc acid), Roquinimex, Rubitecan, Seocalcitol, Temoporfin, Teniposide, Tenuazonic Acid, Topotecan, Valrubicin, Vinblastine, Vincristine, and Zosuquidar.

Amino-containing (including Amide-NH and Sulphonamide-NH, Carbamate-NH, Sulfamate-NH, and Phosphomide-NH): 9-Aminocamptothecin, Aminolevulinic Acid, Amsacrine, Bisantrene, Cactinomyc in, Carboquone, Carmofur, Carmustine, Cyclophosphamide, Dacarbazine, Dactinomycin, Demecolcine, Diaziquone, 6-Diazo-5-oxo-L-norleucine (DON), Edatrexate, Efaproxiral, Eflornithine, Eniluracil, Erlotinib, Fluorouracil, Gefitinib, Gemcitabine, Goserelin, Histamine, Ifosfamide, Imatinib, Improsulfan, Lanreotide, Leuprolide, Liarozole, Lobaplatin, Cisplatin, Carboplatin, Lomustine, Lonafarnib, Mannomustine, Melphalan, Methotrexate, Methyl Aminolevulinate, Miboplatin, Mitoguazone, Mitoxantrone, Nilutamide, Nimustine, Nolatrexed, Oxaliplatin, Pemetrexed, Phenamet, Piritrexim, Procarbazine, Raltitrexed, Tariquidar, Temozolomide, Thiamiprine, Thioguanine, Tipifamib, Tirapazamine, 3-Aminopyridine-2-carboxaldehyde thiosemicarbazone (3-AP)/3-Aminopyridine-4-methyl-2-carboxaldehyde thiosemicarbazone (3-AMP/Triapine/OCX-191/OCX-0191), Trimetrexate, Uracil Mustard, Uredepa ([Bis(1-aziridinyl)phosphinyl]carbamic acid ethyl ester, ethyl carbamate and Meturedepa.

Both Hydroxy-& Amino-containing (including Amide-NH and Sulphonamide-NH, Carbamate-NH, Sulfamate-NH, and Phosphomide-NH): Ancitabine, Anthramycin, Azacitidine, Bleomycins, Bropirimine, Buserelin, Carubicin, Chlorozotocin, Cladribine, Cytarabine, Daunorubicin, Decitabine, Defosfamide, Docetaxel, Doxorubicin, Ecteinascidins, Epirubicin, Gemcitabine, Hydroxyurea, Idarubicin, Marimastat, 6-Mercaptopurine, Pentostatin, Peplomycin, Perfosfamide, Pirarubicin, Prinomastat, Puromycin, Ranimustine, Streptonigrin, Streptozocin, Tiazofurin, Troxacitabine, Vindesine and Zorubicin.

Carboxyl-containing: Butyric acid.

Antiglaucoma Agents:
Amino-containing: Acetazolamide, Brimonidine and Pilocarpine.

Amino- and Hydroxyl-containing: Bimatoprost and Timolol.

Hydroxyl-containing: Latanoprost, Bimatoprost and Travoprost.

Benzodiazepine Tranquilizers and Hypnotics:
Diazepam, Triazolam, Alprazolam, and the like.

Antiulcer Agents:
Amino-containing (including Amide NH and Sulphonamide NH and Phosphomide NH, etc.): Aldioxa, Benexate HCl, Cimetidine, Ebrotidine, Ecabapide, Esaprazole, Esomeprazole, Famotidine, Irsogladine, Lafutidine, Lansoprazole, Omeprazole, Pantoprazole, Pirenzepine, Polaprezinc, Rabeprazole, Ranitidine, Roxatidine, and Troxipide.

Hydroxyl-containing: Enprostil, Misoprostol, Ornoprostil, Plaunotol, Rioprostil, Trimoprostil, and Oryzanol A.

Carboxyl-containing: Acetoxolone, Carbenoxolone, Rebamipide, and Sofalcone.

Amino (or Hydroxyl)- and Carboxyl-containing: Cetraxate, Ecabet, S-Methylmethionine, Rosaprostol, and Rotraxate.

Anticonvulsants:

Amino-containing (including Amide NH and Sulphonamide NH and Phosphomide NH, etc.): Acetylpheneturide, Albutoin, N-benzyl-3-chloropropionamide, Carbamazepine, Cinromide, Clonazepam, Decimemide, Dimethadione, Doxenitoin, Ethosuximide, Ethotoin, Felbamate, Fosphenyloin, Lamotrigine, Levetiracetam, Mephenyloin, Mephobarbital, Metharbital, Methetoin, Nitrazepam, Oxcarbazepine, Oxicarbamazepine, Phenacemide, Phenetharbital, Pheneturide, Phenobarbital, Phenylmethylbarbituric Acid, Phenyloin, Phethenylate Sodium, Primidone, Progabide, Remacemide, Rufinamide, Suclofenide, Sulthiame, Talampanel, Tetrantoin, Topiramate, Valpromide, Zonisamide, 5-Methyl-5-(3-phenanthryl)hydantoin, and 3-Methyl-5-phenylhydantoin.

Hydroxyl-containing: Ganaxolone.

Hydroxyl-, and Amino-containing (including Amide NH and Sulphonamide NH and Phosphomide NH): 4-Amino-3-hydroxybutyric Acid, Atrolactamide, and Buramate.

Carboxyl- and Amino-Containing (including Amide NH and Sulphonamide NH and Phosphomide NH): Gabapentin, Pregabalin, and Vigabatrin.

Carboxyl-containing: Tiagabine, and Valproic Acid.

Antiparkinson

Levodopa and Carbidopa.

Antidepressant:

Amino-containing (including Amide NH and Sulphonamide NH and Phosphomide NH, etc.): Amoxapine, Caroxazone, Demexiptiline, Desipramine, Duloxetine, Fluoxetine, Fluvoxamine, Indalpine, Indeloxazine Hydrochloride, Iproclozide, Iproniazid, Isocarboxazid, Levophacetoperane, Maprotiline, Metapramine, Milnacipran, Minaprine, Moclobemide, Nialamide, Nomifensine, Nortriptyline, Octamoxin, Oxypertine, Paroxetine, Protriptyline, Reboxetine, Rolipram, Sertraline, Tofenacin, Tranylcypromine, Viloxazine, Benmoxine, and Rolicyprine.

Hydroxyl-containing: Befloxatone, Bupropion, Fenpentadiol, Hypericin, Opipramol, Pyrisuccideanol, Toloxatone, and Venlafaxine.

Hydroxyl-, and Amino-containing (including Amide NH and Sulphonamide NH and Phosphomide NH): S-Adenosyl-methionine, 5-Hydroxytryptophan, and Roxindole.

Carboxyl- and Amino-Containing (including Amide NH and Sulphonamide NH and Phosphomide NH): Amineptine, and Tianeptine.

Antihistaminic

Amino-containing (including Amide NH and Sulphonamide NH and Phosphomide NH, etc.): Antazoline, Astemizole, Clobenzepam, Desloratadine, Epinastine, Metron S, Mizolastine, and Tritoqualine.

Hydroxyl-containing: Terfenadine, and N-Hydroxyethylpromethazine Chloride.

Hydroxyl-, and Amino-containing (including Amide NH and Sulphonamide NH and Phosphomide NH, etc.): Cetoxime.

Carboxyl-containing: Acrivastine, Bepotastine, Cetirizine, and Levocabastine.

Carboxyl- and Hydroxyl-containing: Fexofenadine.

Anticancer, Antioxidative, Antiinflammatory, and Cardioprotective Agent:

Trans-Resveratrol [(E)-3,4',5-trihydroxystilbene).

Antidiabetic:

Metformin, and Nateglinide/Glipizide/Glibenclamide (Glyburide).

Local Anaesthetics

Amino-containing: Benzocaine, Chloroprocaine, Proparacaine, Tetracaine, Cocaine, Propoxycaine, Procaine, Proparacaine, Tetracaine, Articaine, Bupivacaine, Carticaine, Cinchocaine, Etidocaine, Levobupivacaine, Lignocaine, Mepivacaine, Piperocaine, Prilocalne, Ropivacaine, Trimecaine It should be understood that while the lists of names of various categories of drugs have been included above, such lists are presented in a way of illustration of the structural features of the qualifying drugs in this invention and therefore, the number and types of listed drugs are not necessarily limited thereto. In principal, any amino-, and/or carboxyl, and/or carbonyl-, and/or hydroxyl-containing drug (from both known and investigational drugs), irrespective of its therapeutic category and their mechanism of action, as listed in drug databases such as Merck Index, prous science's ensemble, integrity, iddb, and the like, are generally covered within the true spirit and scope of the present invention. For clarity, in addition to the above lists of drugs, any amino-, and/or carboxyl-, and/or carbonyl-, and/or hydroxyl-containing drug(s) (both known and investigational drugs) from the following therapeutic areas are covered without any limitation:

Central Nervous System:

Sedatives, Hypnotics, Antidepressants, Antipsychotics and Antimanics, Analgesics & Antipyretics, Antimigraine agents, Anticonvulsants, Drugs used in parkinsonism and movement disorders, Drug for dementia, Antiemetics, drugs for Vertigo, CNS Stimulants & activators. Quetiapine, Paliperidone (active metabolite of risperidone), Fluphenazine Eye:

Antiinfective eye preparations, Antiinflammatory and anti-allergic preparations, antiglaucoma drugs and other preparations to cure eye diseases.

Ear, Nose and Oropharynx:

Drugs used aural, nasal and oropharyngeal preparation.

Cardiovascular System:

Antiarrhythemic drugs, Antihypertensives (including alfa/beta-blockers, channel blockers, ACE inhibitors, Angiotensin H receptor antagonists, diuretics, etc.), Antianginals (including nitrates, calcium channel blockers, etc.), Drugs for cardiac failure and shock, Vasodilators, Coagulants, Anticoagulants, Thrombolytics and antiplatelet drugs.

Respiratory System:

Respiratory stimulants, Antitussives, Expectorants, Mucolytics and Decongestants, Antihistamine agents, and antiasthmatics.

Gastro Intestinal Tract:

Antiulcer and Antisecretory drugs (including H.sub.2 receptor antagonists, Proton Pump Inhibitors, Prostaglandin analogues, etc.), Antacids, Antispasmodics and drugs modifying intestinal motility, Antidiarrhoeals (including antimotility and antimicrobial drugs) and drugs acting on gall bladder.

Genito Urinary System:

Urinary antiinfectives, Diuretics, Urinary analgesics & antispasmodics, Antiinfective drugs acting on urethra and vagina, drugs acting on uterus, Drugs for prostatic hypertrophy (including alfa blockers and antiandrogens), Drugs for erectile dysfunction, and Spermicidal & nonhormonal contraceptives.

Skin:

Keratolytics, topical antiinfectives, topical antifungals, topical parasiticidals, topical steroids, topical drugs for acne vulgaris, drugs for psoriasis, pigmentation disorders, and Antiseborrhoeics.

Musculo-Skeletal Disorders:

Non Steroidal Anti Inflammatory Drugs (NSAIDs) including COX-2 inhibitors, Antiarthritic agents, Immunosuppressants, Topical analgesics, Muscle relaxants and Neuromuscular Drugs.

Infections and Infestations:

Penicillin antibiotics, Cephalosporin antibiotics, Quinolone & Fluoroquinolone antibiotics, Macrolide antibiotics, Chloramphenicol, Tetracycline antibiotics, Sulfonamides, Antianaerobics such as Metronidazole, Antitubercular drugs, Antileprosy drugs, Antifungals, Antiprotozoals, Anthelminthics & Antiinfestive Drugs, Antimalarials and Antivirals.

Endocrine System:

Anabolic and androgenic steroids, Corticosteroids, Oestrogens, Progestogens and Hormonal contraceptives, Fertility Agents, Trophic hormones and related drugs, Thyroid and antithyroid drugs, Antidiabetics and hyperglycaemics.

Metabolism:

Hypolipidaemic drugs (including fibric acid derivatives, statins [(i.e., HMG CoA reductase inhibitors), nicotinic acid group, etc.], Drugs used for Gout and Drugs affecting bone metabolism (including bisphosphonates).

Neoplastic Disorders:

Anticancer drugs such as alkylating agents, cytotoxic antibiotics, antimetabolites such as cytarbine, Fludarbine, 5-Fluorouracil, Mercaptopurine, Thioguanine, etc., Vinca alkaloids and Etoposide, Taxanes, Topoisomerase 1 inhibitors, Cytotoxic immunosuppressants, Immunostmulants, Cytoprotectives such as Amifostine, Oestrogens, Progestogens, hormon antagonists and other antineoplastic drugs.

Allergy and Immunology:

Antiallurgics such as non-sedative antihistamins (e.g., Cetirizine, Desloratadine, Terfenadine, Fexofenadine, etc.), sedative histamines and histamine receptor blockers.

Anaesthetics & Surgicals:

Local anaesthetics, intravenous anaesthetics, inhalation anaesthetics and muscle relaxants.

In addition to the above list of drugs, the present invention also covers newer drugs with the above mentioned active functional groups as listed in the Merck index (14.th edition) and other drug databases such as Prous Science's ensemble, integrity and the investigational drugs as listed in databases such as iddb, ensemble, integrity, and the like without any limitation.

Preferred bioactive agents include the fluoroquinolone antibiotics, local anesthetics and valproic acid. Preferred fluoroquinolone antibiotics include; alatrofloxacin, balofloxacin, ciprofloxacin, clinafloxacin, danofoxacin, delafloxacin, dextrofloxacin, difloxacin, enoxacin, enrofloxacin, garenoxacin, gatifloxacin, gemifloxacin, grepafloxacin, levofloxacin, lomefloxacin, marbofloxacin, moxifloxacin, nadifloxacin, norfloxacin, ofloxacin, orbifloxacin, pefloxacin, sitafloxacin, sparfloxacin, temafloxacin, tosufloxacin, tosulfloxacin and trovafloxacin. Still further preferred are: danafloxacin, detrofloxacin, difloxacin, enrofloxacin, marbofloxacin, moxifloxacin, levofloxacin, ofloxacin, pefloxacin. Still further preferred is levofloxacin and moxifloxacin. Most preferred is levofloxacin and moxifloxacin. The preferred local anaesthetics are benzocaine and procaine, most preferred is benzocaine.

Preferred bioactive moieties that can be utilised in the present invention are those containing one or more functional groups such as carboxylate, hydroxyl, amino, thiol, phosphate or sulphate.

Examples of preferred bioactive moieties that can be utilised in the present invention are levofloxacin and valproic acid.

In accordance with the invention the bioactive moieties are capable of being released at a rate equal to or faster than the rate of biodegradation of the polymer backbone. By providing the biodegradable polymer with such properties, structural integrity of the polymer backbone (and hence the physical form (e.g. shape and size etc) in which the polymer is provided) can be maintained while the drug is being released.

By the bioactive moieties being "released at a rate equal to or faster than the rate of biodegradation of the polymer backbone" is meant that the biodegradable polymer is constructed such that under given physiological conditions or in a given biological environment the measurable concentration of the released bioactive moiety in its biologically active form is equal to or greater than the measurable concentration of the corresponding monomer-bioactive moiety conjugate from which the polymer is derived (e.g. formula (II)). Such concentration measurement may be readily conducted by those skilled in the art, for example by using HPLC or GC analytical techniques.

In one embodiment, the bioactive moieties are capable of being released at a rate faster than the rate of biodegradation of the polymer backbone. In that case, the biodegradable polymer is constructed such that under given physiological conditions or in a given biological environment the measurable concentration of the released bioactive moiety in its biologically active form is greater than the measurable concentration of the corresponding monomer-bioactive moiety conjugate from which the polymer is derived (e.g. formula (II)).

In one a further embodiment, the measurable concentration of the released bioactive moiety in its biologically active form is at least 5%, at least 10%, at least 20%, at least 40%, at least 50%, at 1×, at least 2× at least 5× greater than the measurable concentration of the corresponding monomer-bioactive agent conjugate from which the polymer is derived (e.g. formula (II)).

In connection with providing the biodegradable polymers with an appropriate structure to promote a desired rate of release of the bioactive moiety, those skilled in the art will appreciate, for example, that hydrolysis of an ester moiety will typically occur more readily than that of an amide or carbamate moiety. Thus to promote a rate of release of the bioactive moiety from the polymer backbone that is, for example, faster than the rate of biodegradation of the polymer backbone, one might construct the conjugate such that the polymer backbone comprises only amide and/or carbamate biodegradable moieties and the bioactive moiety is covalently coupled to the backbone via an ester moiety.

Those skilled in the art will also appreciate that factors such as steric crowing and electronic effects around a given biodegradable moiety can alter its propensity to undergo hydrolytic cleavage. Both the polymer backbone and the pendant bioactive moiety can be a source of such effects. For example, a biodegradable moiety having a non hydrogen substituent (e.g. alkyl, aryl, alkylaryl, carbocyclyl) located α and/or β to it will typically be less susceptible to hydrolytic cleavage relative to the same moiety having hydrogen substituents located α and/or β to it. Accordingly, steric crowing around a given biodegradable moiety can be used to influence the rate of release of the bioactive moiety and/or the rate bio of the polymer backbone.

The skilled artisan would be capable of selecting the appropriate spacer based on an evaluation of steric constraints, phase chemistry and surface chemistry. For example, larger bioactive moieties can be advantageously spaced from the monomer by the choice of a longer spacer.

The skilled artisan would also be capable of selecting the appropriate linkage chemistry in the synthesis of the biodegradable polymer so that the rate of bioactive moiety release was equal to or faster than the rate of polymer degradation.

Generally, the rate of hydrolytic cleavage will be in the order: anhydride moiety, ester moiety (including carboxylic acid esters, sulphate esters and phosphate esters) >carbamate>amide.

By tailoring at least the rate at which the bioactive moiety is released from the polymer backbone, the polymer-bioactive moiety conjugates of the invention can advantageously function as a sustained bioactive moiety delivery system.

At the very least the bioactive moiety must be releasable from the polymer conjugate per se. However, the polymer may also biodegrade in vivo or in vitro to a degree such that the polymer backbone fragments, with the moiety remaining tethered to such a fragment(s). In that case, the moiety will nevertheless still be capable of being released or cleaved from the fragment. Having said this, the bioactive moieties must still be released at a rate equal to or faster than the rate of biodegradation of the polymer backbone as herein defined.

In one embodiment, the bioactive moiety is releasable where the polymer backbone undergoes substantially no biodegradation during the release time frame.

A consequence of having a higher rate of bioactive moiety release is that it avoids the situation of statistical hydrolysis of a long chain polymer (e.g., polyanhydride) wherein there is the possibility to produce oligomers of the bioactive moieties in fragments that may consequently be eluted from the body as the oligomer before it can be released as the active component.

As used herein, the term "constituent monomer" refers to the residue of that monomer as it appears in the polymer backbone.

Figure 9:
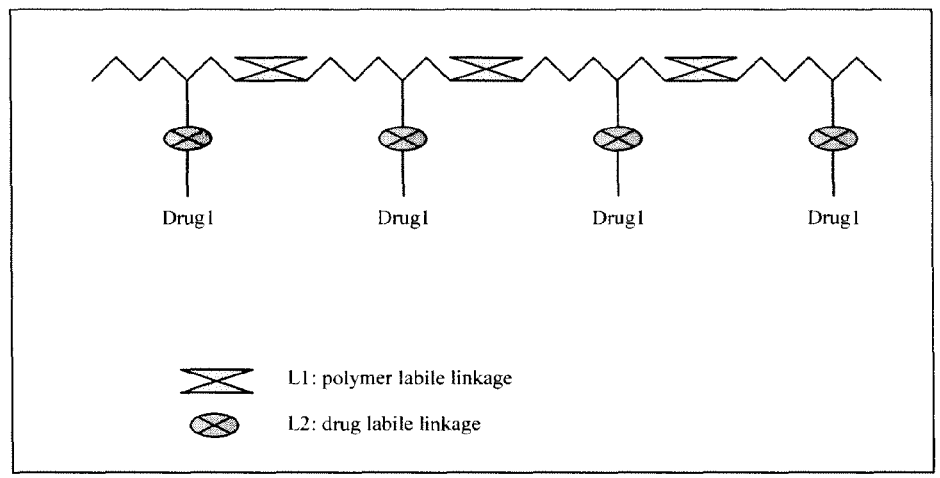
FIG. 9 illustrates a simplified structure of a biodegradable polymer in accordance with the invention.

The biodegradable polymers of the present invention may have a structure as represented in FIG. 9. The bioactive moiety, will be attached to the polymer via a labile linkage that allows release of the bioactive moiety after administration. Furthermore, the polymer backbone will also include biodegradable moieties that allow degradation of the polymer after administration.

The biodegradable polymer will be designed such that release of the bioactive moiety occurs at a rate that is faster than or equal to the rate of degradation of the polymer.

Thus, with reference to FIG. 9 the rate of breakdown of the linkages L2 is faster than or equal to, preferably faster than, the rate of breakdown of the linkages L1. The labile linkage L1 may be characterised by a covalent bond between the bioactive moiety and the polymer backbone. Alternatively, the labile linkage may be characterised by the presence of a spacer moiety between the bioactive moiety and the polymer backbone.

The linkage within the polymer backbone L2 may be characterised by the presence of a covalent bond between backbone fragments containing one or more monomers and/or by a spacer moiety between backbone fragments containing two or more monomers. Polymer backbones containing side chains may be further characterised by labile linkages within the side chains.

It will be appreciated that such labile linkages are those through which the bioactive moiety is released and the polymer backbone biodegrades. The labile linkages or linkers may therefore also be referred to as biodegradable moieties.

Providing the bioactive moiety with a different rate of release relative to the rate of biodegradation of the polymer backbone allows for the release of substantially all the bioactive moiety prior to the onset of significant polymer backbone degradation.

The biodegradable polymers of the present invention can accommodate high bioactive moiety loadings, minimising the amount of material required to deliver a dose of bioactive moiety. Bioactive moiety loadings of at least 10% by weight, preferably at least 20% by weight, more preferably at least 30% by weight relative to the total weight of the biodegradable polymer may be achieved.

The bioactive moiety loading may also be expressed in terms of its mol % relative to the total number of moles of monomer that form the polymer. Generally, the polymer-bioactive moiety conjugate will comprise at least 10, at least 25, at least 35, at least 45 or up to 50 mol % of bioactive moiety, relative to the total number of moles of monomer that form the polymer.

In some embodiments, the polymer-bioactive moiety conjugate will comprise up to 60, up to 70, up to 80, up to 90 and even up to 100 mol % of conjugated bioactive moiety, relative to the total number of moles of monomer that form the polymer. However, in that case, it will be appreciated that the amount of conjugated bioactive moiety greater than 50 mol % will necessarily be derived from moieties other than the —X—R(ZD)-Y— type moieties shown in general formula (I). For example, the other monomers which a polymerised with the monomer-bioactive moiety conjugate of the invention (formula (II)) may also comprise conjugated bioactive moiety.

Figure 10:
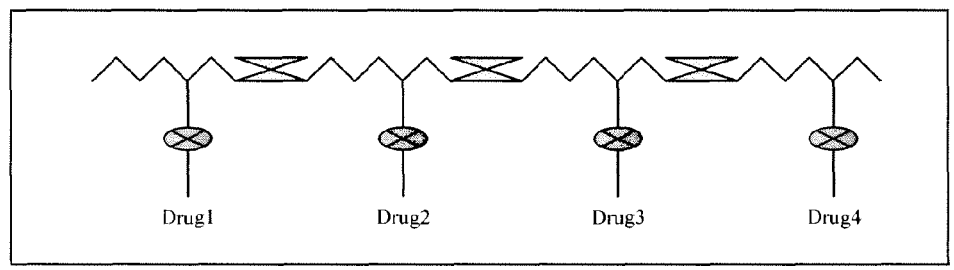
FIG. 10 illustrates a simplified structure of a biodegradable polymer according to the invention with multiple drugs.

The biodegradable polymer may contain more than one type of bioactive moiety as illustrated in FIG. 10.

Figure 11:
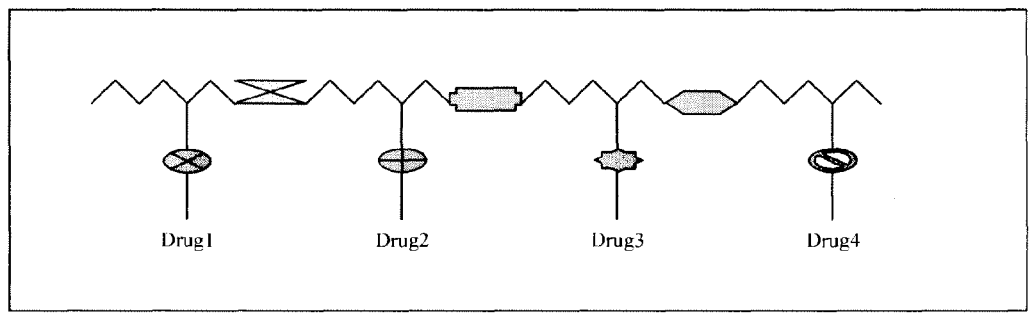
FIG. 11 illustrates a simplified structure of a biodegradable polymer according to the invention with multiple linker types and drugs.

The biodegradable polymer may contain more than one type of linker or biodegradable moieties as illustrated in FIG. 11.

As discussed above, varying the lability of linker moieties provides control over the release profile of the bioactive moieties. More than one type of linker moiety can be used combined with more than one type of bioactive moiety so as to provide a method of sequential controlled release of multiple bioactive moieties.

In the context of multiple bioactive moieties, the biodegradable polymers of the present invention offer the advantage of being able to control a) the relative proportions of the bioactive moieties, b) their relative positions as attached to the polymer backbone and c) their degree of dispersability (e.g. they may be linked to only certain segments in the polymer).

The rate of breakdown of the labile linkages L2 may be influenced by external stimuli so as to externally modulate the release of the bioactive moiety.

The biodegradable polymer can be homogeneous or heterogeneous with respect to the bioactive moiety(ies) used.

Preferably the biodegradable polymer is designed such that the bioactive moieties are released unencumbered by excess molecular fragments. In other words, the bioactive moieties are released such that they do not comprise a residue derived from the polymer backbone or spacer moiety. By this it is meant that the bioactive moieties are released in their substantially original form (i.e. before being conjugated) and are essentially free from, for example, fragments of oligomer or polymer derived from the polymer backbone. This is highly desirable in avoiding situations in which a loss of bioactive moiety efficiency occurs through loss of pharmacological effect through poor transport of, for example, sterically demanding bioactive/oligomer moieties through physiological barriers may occur, resulting in elution of the active bioactive moiety away from the target site.

The biodegradable polymers of the present invention employ polymer backbones (as illustrated by A and B in formula (I)) which is preferably selected from or comprises polyurethane optionally comprising one or more chain extenders (e.g. polyester), polyanhydride, polycarbonate, polyurea, polyamide, polyimide and polyester (eg PLGA (poly(lactic-co-glycolic acid)), PLA (polylactic acid), PGA (polyglycolic acid), PHB (polyhydroxybutyrate), PCL (polycaprolactone); and copolymers thereof. More preferably the polymer backbones are selected from or comprise: polyurethanes, polyesters, polyamides and copolymers thereof. Suitable copolymers include poly(urethane-ester) and poly(ester-urethane).

Provided that the polymer backbone is biodegradable, it may also include chain extenders, star compounds and dendrimers to introduce branching and spacing between segments within the polymer. The polymer backbone may be linear, substantially linear, branched, hyperbranched, stars, a block polymer or co-polymer. Co-polymers may be advantageous in allowing incorporation of more that one bioactive moiety with known relative positions in the final polymer.

It may also be desirable for the biodegradable polymers to be substantially amorphous and thus contain a low amount of crystalline segments. Such polymers can provide a more predictable rate of bioactive moiety release as well as assisting with the production of materials that are more flexible which can assist with producing coatings as well as assisting with the rate of polymer degradation.

Additional variables such as the choice of co-monomers and the means to produce the polymers can also assist with the production of highly amorphous and/or flexible polymers. For example, using monomers such as caprolactone or polyester polyols such as polycaprolactone diol can decrease the crystallinity and increase the flexibility of the resulting polymer.

For the polyurethanes it may be important to limit the content of hard segment (use conventional definition of hard segment—chain extenders+diisocyanates). One example of a typical class of chain extender are low molecular weight diols. Examples of such chain extenders include ethylene glycol, propane diol, propylene glycol, butane diol etc. Apart from the potential toxicity of such chain extenders, limiting the hard segments in the polyurethanes also provides a reason to reduce the low molecular weight diol content as described above.

The polymer backbone of the biodegradable polymers of the present invention have a molecular weight of about 250 Daltons to about 2 MM Daltons, preferably from 500 Daltons to 500,000 Daltons.

In one embodiment, the biodegradable polymer in accordance with the invention comprises as part of its polymer backbone a plurality of moieties of general formula (I):

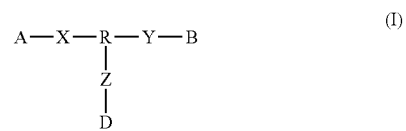

A and B, which may be the same or different, represent the remainder of the biodegradable polymer backbone. As per the discussion above in respect of the polymer backbone, A and B may be selected from or comprises polyurethane optionally comprising one or more chain extenders (e.g. polyester), polyanhydride, polycarbonate, polyurea, polyamide, polyimide and polyester (eg PLGA (poly(lactic-co-glycolic acid)), PLA (polylactic acid), PGA (polyglycolic acid), PHB (polyhydroxybutyrate), PCL (polycaprolactone); and copolymers thereof. In some embodiments, A and B are selected from or comprise: polyanhydrides; polyurethanes; polyesters; polyamides and copolymers thereof. In some embodiments, A and B are selected from or comprise a copolymer of polyurethane and polyester. A and/or B will also comprise one or more bioactive moieties covalently coupled to the polymer backbone.

In some embodiments, the polymer-bioactive moiety conjugate in accordance with the invention comprises as part of its polymer backbone a plurality of moieties of general formula (Id):

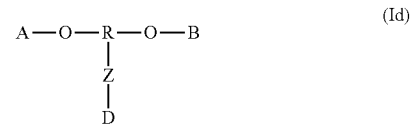

A and B, which may be the same or different, represent the remainder of the biodegradable polymer backbone, wherein A and B are selected from or comprise a copolymer of polyurethane and polyester. Examples of polyesters include PLGA (poly(lactic-co-glycolic acid)), PLA (polylactic acid), PGA (polyglycolic acid), PHB (polyhydroxybutyrate) and PCL (polycaprolactone). In some embodiments, the polyurethanes optionally comprise one or more chain extenders (e.g. polyester). A and/or B will also generally comprise one or more bioactive moieties covalently bonded to the polymer backbone.

Depending upon the intended application, A and B may be selected for their biocompatible and/or their biodegradable properties. Those skilled in the art can readily select polymers to provide for such properties.

As used herein, "biocompatible polymer" refers to a polymer that both in its intact, that is, as synthesized, state and in its decomposed state (i.e. its degradation products), is compatible with living tissue in that it is not, or at least is minimally, toxic to living tissue; does not, or at least minimally and reparably does, injure living tissue; and/or does not, or at least minimally and/or controllably does, cause an immunological reaction in living tissue.

The moiety "R" present in formulae (I), (Ia), (Ib), (Ic), (Id), (II), (IIa) and (VI) represent a linear or branched optionally substituted hydrocarbon. In some embodiments the hydrocarbon may comprise between 1 and 12 carbon atoms, for example between 1 and 6 carbon atoms or 2 or 3 carbon atoms. The hydrocarbon may be partially or completely saturated or unsaturated (including moieties that are aromatic). Specific examples of R include a moiety having one of the following structures:

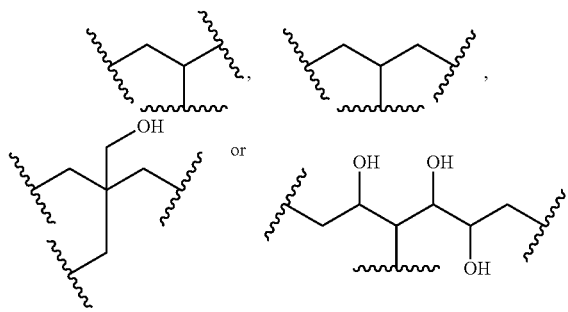

A bioactive moiety can be conjugated to all monomers that form the biodegradable polymer, or only to monomers of a particular character (e.g., polyalcohols) or proportions of monomers.

Monomers conjugated with one bioactive moiety may be polymerised with monomers conjugated with another different bioactive moiety.

In one embodiment, a monomer-bioactive moiety conjugate that may be used in preparing the biodegradable polymers has general formula (II):

(II)

where, X', Y', R, Z and D are as herein defined.

In some embodiments, the monomer-bioactive moiety conjugate has general formula (IIa):

(IIa)

where, R, Z and D are as herein defined.

In some embodiments, the monomer-bioactive moiety conjugate may have a more specific structure of formula (III), (IV), (V) or (Va):

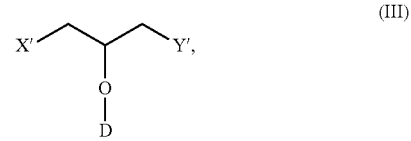
(III)

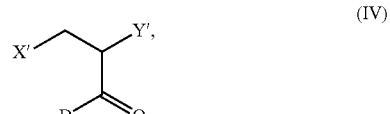
(IV)

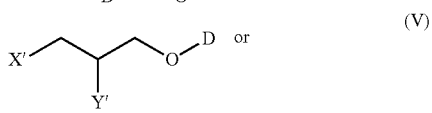
(V)

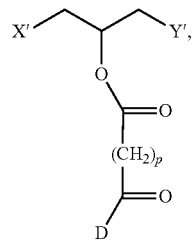
(Va)

where D, X' and Y' are as herein defined, and p is between 1 and 18.

In some embodiments, in formulae (III), (IV), (V) and (Va), X' and Y' are each hydroxyl.

Monomers that are polymerised with the monomer-bioactive moiety conjugate to form the biodegradable polymers of the invention will not only comprise compatible chemical functionality to react with the monomer-bioactive moiety conjugate but that reaction will of course give rise to a biodegradable moiety.

The expression "compatible chemical functionality" refers to chemical functionality that is capable of undergoing reaction with the monomer-bioactive moiety conjugate to form the polymer. For example, the monomers of formula (II) comprise at least two terminal reactive functional groups X' and Y'. These functional groups will react with compatible functional groups of one or more monomers to form the polymer and give rise to a biodegradable moiety. Thus, where both X' and Y' are hydroxyl groups, those skilled in the art will appreciate that they will react with a variety of functional groups such as: isocyanate functionality to form carbamate or urethane linkages; carboxylic acid functionality to produce ester linkages; carboxylic acid halide functionality to produce ester linkages; ester functionality to produce trans-esterified ester linkages; and anhydride functionality (including cyclic anhydride groups) to produce ester linkages. The expression "compatible chemical functionality" therefore refers to functionality or groups such as isocyanate, carboxylic acid, carboxylic acid halide, ester and anhydride (including cyclic anhydride groups) groups.

In some embodiments of a monomer-bioactive moiety conjugate of formula (II), X' and Y' are each hydroxyl groups. The hydroxyl groups are capable of undergoing polymerisation with at least one monomer having compatible chemical functionality, and react with the compatible chemical functionality to afford a biodegradable moiety. In some embodiments, the polymerisation of the monomer of formula (II) with at least one monomer having compatible chemical functionality affords a biodegradable moiety selected from an ester and urethane (carbamate) moiety.

Accordingly, where both X' and Y' are hydroxyl groups, the expression "at least one other monomer comprising compatible chemical functionality" used herein typically refers to monomers comprising one or more compatible chemical functional groups selected from isocyanate, carboxylic acid, carboxylic acid halide, ester, anhydride (including cyclic anhydride groups) groups and combinations thereof. Thus in some embodiments, the monomer-bioactive moiety conjugate of formula (II) where X' and Y' are each hydroxyl groups can polymerise with at least one other monomer comprising one or more compatible chemical functional groups, where the one or more compatible chemical functional groups are selected from isocyanate, carboxylic acid, carboxylic acid halide, ester, anhydride (including cyclic anhydride groups)

groups and combinations thereof. Preferably, the at least one other monomer comprises a plurality of compatible chemical functional groups. Examples of such monomers are polyisocyanates and polyacids. Typically the monomers will be a diisocyanate or a diacid.

In some embodiments the at least one other monomer may contain one group of compatible chemical functionality (as defined herein) in addition to one group such as an amino, thio or hydroxy group which is not, of itself, compatible for undergoing polymerisation with a monomer of formula (II) where both X' and Y' are hydroxyl groups. Examples of such monomers are hydroxy-acids and amino acids. In the case of a hydroxy-acid, the carboxylic acid is capable of reacting with a hydroxy group of the monomer of formula (II) to produce a hydroxy-terminated compound.

Likewise in the case of an amino acid, the carboxylic acid is capable of reacting with the monomer of formula (II) where both X' and Y' are hydroxyl groups to produce an amino-terminated compound. Likewise in the case of a thio acid, the carboxylic acid is capable of reacting with the monomer of formula (II) where both X' and Y' are hydroxyl groups to produce a thio-terminated compound. These hydroxy/amino/thio terminated compounds may subsequently undergo reaction with another monomer bearing a carboxylic acid, isocyanate group, etc. so that the polymer backbone may comprise one or more ester, amide, thioester, urea, urethane, thiocarbamate functional groups.

For example, polymerisation of formula (II) where both X' and Y' are hydroxyl groups with a diisocyanate produces a polyurethane. Such a polyurethane will typically comprise 50 mol % diol residue and 50 mol % diisocyanate residue. Where each diol monomer of formula (II) comprises one bioactive moiety, the "loading" of the bioactive moiety in the polymer-bioactive moiety conjugate may be designated as 50%.

The polymerisation formula (II) where both X' and Y' are hydroxyl groups with a diacid produces a polyester. Such a polyester will typically comprise 50 mol % diol residue and 50 mol % diacid residue. Where each diol monomer of formula (II) comprises one bioactive moiety, the "loading" of the bioactive moiety in the polymer-bioactive moiety conjugate is designated herein as 50 mol %, relative to the monomers that form the polymer.

Those skilled in the art will also recognise that polymerisation of formula (II) where both X' and Y' are hydroxyl groups with a polyisocyanate, polyacid or polyester may also take place in the presence of one or more other types of polyols (e.g. polyester polyols). In some embodiments, the conjugate of formula (II) where both X' and Y' are hydroxyl groups is polymerised with a polyisocyanate and at least one other monomer selected from the group consisting of a polyacid, a polyester and a polyester polyol. The structures of the one or more other types of polyols may or may not comprise one or more bioactive moieties. An example of this second type of polyol is 1,6-hexanediol. The polymer-bioactive moiety conjugate so-formed may or may not have a bioactive moiety loading of less than 50 mol %. For example when formula (II) (where both X' and Y' are hydroxyl groups) is polymerised in the presence of an equimolar amount of 1,6-hexanediol and 2 molar equivalents of diisocyanate, the polyurethane so-formed will typically comprise the residues of the three components in the ratio of 1:1:2. Such conjugates are contemplated by the present invention. Such polymer systems may provide a useful means of modifying the physical properties of the polymer conjugates.

Similar comments also apply where X' and/or Y' represent different functional groups (i.e. other than both being hydroxyl groups). For example, X' and Y' may each be independently selected from hydroxyl, amine, carboxylic acid, isocyanate, and carboxylic acid halide.

In some embodiments, the present invention provides a monomer-bioactive moiety conjugate of formula (II) where X' and Y' are each hydroxyl and the bioactive moiety (D) is selected from fluorquinolone antibiotics. Preferred fluorquinolone antibiotics are levofloxacin and moxifloxacin.

In one aspect, the present invention also provides a biodegradable polymer of formula (I) obtainable by polymerising a monomer-bioactive moiety conjugate of formula (II):

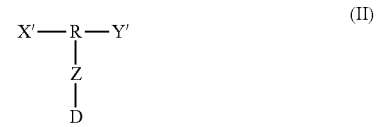

where:
X' and Y' are each hydroxyl;
R represents a linear or branched optionally substituted hydrocarbon;
Z is a spacer moiety; and
D is a releasable bioactive moiety;
with a polyisocyanate and at least one selected from the group consisting of a polyacid, a polyester, and a polyester polyol.

In one embodiment, the biodegradable polymer of formula (I) is obtainable by polymerising a monomer-bioactive moiety conjugate of formula (II), where X' and Y' are each hydroxyl, with a polyisocyanate and a polyester polyol.

Suitable polyisocyanates may be selected from the group consisting of m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4'diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, polymethylene polyphenhyl polyisocyanates and alkyl esters of lysine diisocyanate (preferably ethyl ester of lysine diisocyanate) and combinations thereof. Preferred polyisocyanates include 1,6-hexamethylene diisocyanate and alkyl esters of lysine diisocyanate (preferably ethyl ester of lysine diisocyanate).

Suitable polyester polyols may be selected from the group consisting of polycaprolactone diol (PCLD), poly(DL lactide) (DLLA) and poly(lactic acid-co-glycolic acid) (PLGA), and combinations thereof.

Suitable polyacids may be selected from the group consisting of oxalic acid, fumaric acid, maleic acid, succinic acid, glutaric acid, adipic acid, pimelic acid, suberic acid, azelaic acid, sebacic acid, phthalic acid, dodecanediacid, isophthalic acid, terephthalic acid, dodecylsuccinic acid, napthalene-2,6-dicarboxylic acid, naphthalene-2,7-dicarboxylic acid, cyclohexane dicarboxylic acid, itaconic acid, malonic acid, and mesaconic acid. Preferred polyacids include maleic acid and succinic acid.

Those skilled in the art will be able to selected both X' and Y' for reaction with one more monomers having compatible chemical functionality to afford the biodegradable polymers according to the invention. Where X' is a compatible chemical functionality with Y' (e.g. hydroxyl and carboxylic acid), those skilled in the art will also appreciate that the monomer-bioactive moiety conjugate may be polymerised with itself (e.g. where the monomer-bioactive moiety conjugate is a hydroxy-acid).

The invention also provides a process for preparing a monomer-bioactive moiety conjugate of formula (IIa):

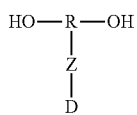

wherein:
R represents a linear or branched optionally substituted hydrocarbon;
Z is a linking group; and
D is a releasable bioactive moiety,
said process comprising covalently coupling a linking precursor group Z' in a compound of formula (VI):

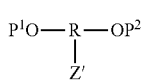

wherein:
$P^1$ and $P^2$ are each independently H, a protecting group, or $P^1$ and $P^2$ together fond a protecting group; and
R is as defined above,
with a group selected from D or D-Z",
wherein:
D is a bioactive moiety in protected or unprotected form or prodrug thereof; and
Z" is a linking precursor group,
wherein the coupling of Z' with D, or the coupling of Z' with Z" in the group D-Z", forms the

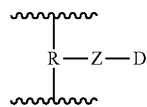

moiety in the conjugate of formula (IIa),
and where $P^1$ and/or $P^2$ are protecting groups said process further comprises the step of removing the protecting group or groups.

Z' and Z" (when present) are each linking precursor groups which afford the linking group Z in the monomer-bioactive moiety conjugate of formula (IIa).

In some embodiments, Z' is a moiety comprising a functional group such as a carboxylic acid, acid halide, primary amino, secondary amino, hydroxy group, thiol group, phosphate group or sulphate group that couples to D or couples to Z" in the group D-Z".

In some embodiments, Z" is a moiety comprising a functional group such as a carboxylic acid, acid halide, primary amino, secondary amino, hydroxy group, thiol group, phosphate group or sulphate group that couples to Z'.

For example, the compound of formula (VI) may be derived from a compound of formula (VII):

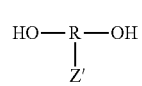

wherein Z' and R are as defined above.

To promote reaction between D or D-Z" and the Z' moiety in general formula (VI), those skilled in the art will appreciate that the relevant coupling functional group on the bioactive agent may be suitably modified. For example, where Z' in formula (VI) comprises a hydroxy group, ester formation through reaction of this hydroxy group with a carboxylic acid group in D or a carboxylic acid group on Z" in D-Z" can in some cases prove difficult. Under these circumstances, ester formation may be facilitated by first converting the carboxylic acid group in D or D-Z" into an acid halide (e.g. acid chloride) group and then reacting the acid halide group with the hydroxy group. Coupling agents such as those mentioned in Tetrahedron Volume 60, Issue 11, 8 Mar. 2004, pages 2447-2467, could also be employed. Exemplary coupling agents include those listed below in Table 1.

TABLE 1

Coupling agents for promoting reaction between carboxylic acid, acid halide and hydroxy groups.

| Acronym | Chemical name |
|---|---|
| DCC | N,N'-dicyclohexylcarbodiimide |
| DIEA(DIPEA) | diisopropylethylamine |
| EDC | 1-[3-(dimethylamino)propyl]-3-ethylcarbodiimide hydrochloride |
| HATU | O-(7-azabenzotriazol-1-yl)-1,1,3,3-tetramethyluronium hexafluorophosphate |
| HBTU | O-(benzotriazol-1-yl)-1,1,3,3-tetramethyluronium hexafluorophosphate |
| HOBt | 1-hydroxybenzotriazole |

The compound of formula (VI), where Z' comprises a hydroxyl group, may be derived from a compound of formula (VII) through alcohol group protection. The compound of formula (VI), where Z' comprises a primary or secondary amino group, may be derived from a compound of formula (VII) through amino group protection. In some cases, the compound of formula (VI), where Z' comprises a carboxylic acid group, may be derived from a compound of formula (VII) using a protection group strategy. The skilled worker will recognise that the compound of formula (VI), where Z' comprises an acid halide, may be derived from the corresponding compound where Z' comprises a carboxylic acid.

Where the bioactive agent has more than one functional group that can be used to covalently couple it to a compound of formula (VI), those skilled in the art will be able to select appropriate reaction conditions, reagents and/or protecting groups to promote the desired coupling reaction.

Techniques, equipment and reagents well known in the art can advantageously be used to prepare the monomer-bioactive agent conjugates in accordance with the invention.

Examples of general strategies for synthesising monomer-bioactive moiety conjugates of formula (IIIa), which employ protecting group strategies, are represented in Scheme 1 below (where D is a releasable bioactive agent; and D' is that part of the releasable bioactive moiety other than the hydroxyl, amine, carboxylic acid, etc):

Scheme 1: General strategies for synthesising monomer-bioactive moiety conjugates of formula (IIa).
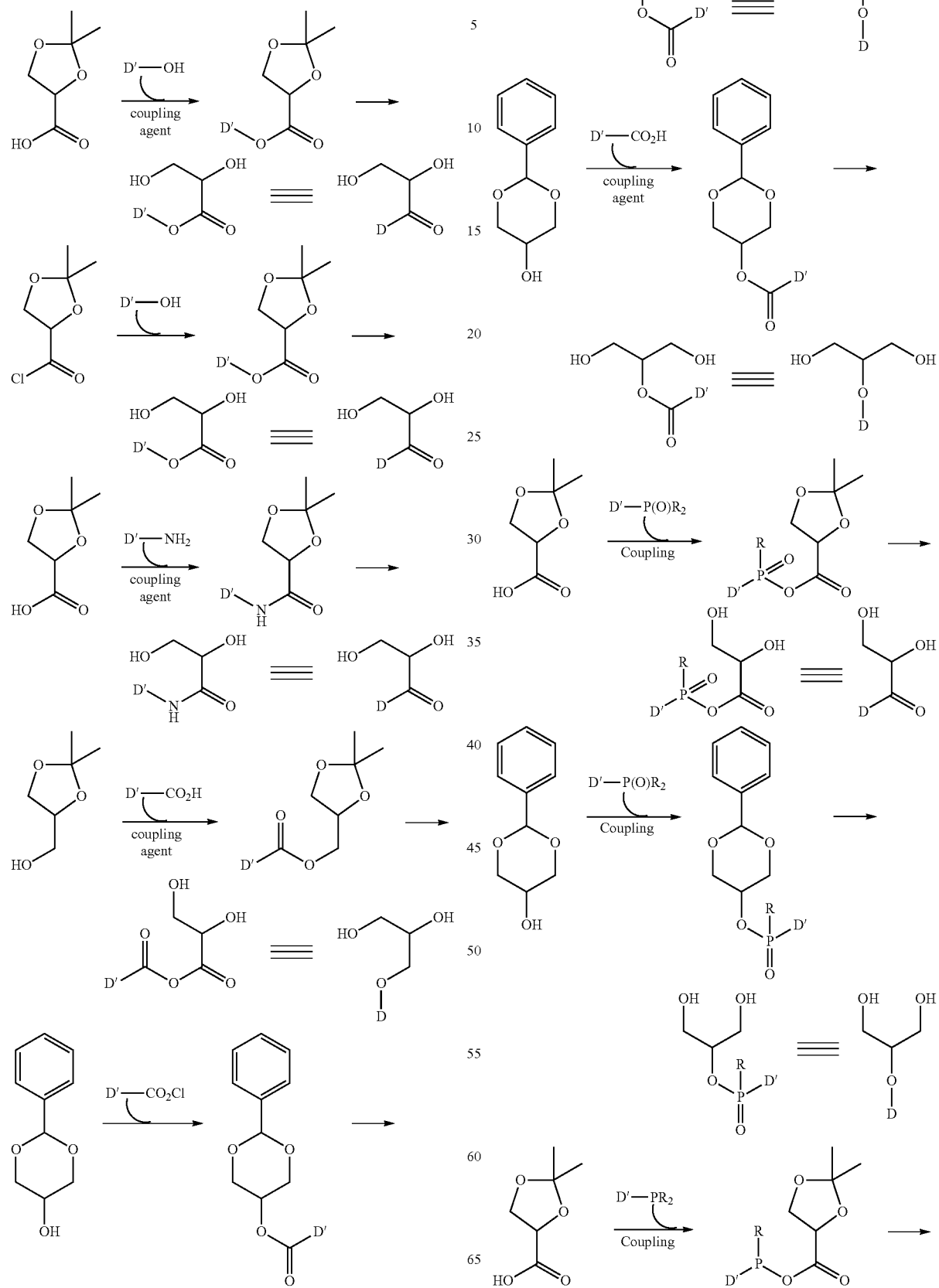

-continued

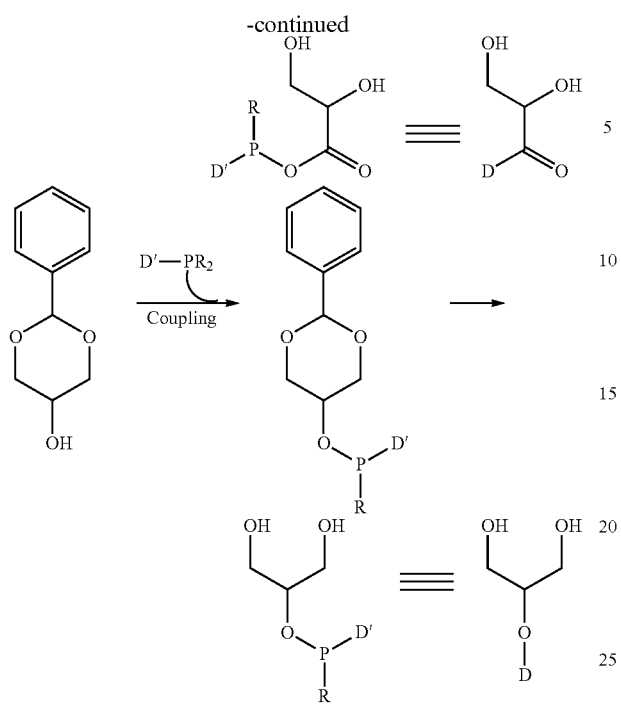

The R group may be substituted with one or more groups comprising a releasable bioactive agent (D), as shown in the following structure derived from pentaerythritol:

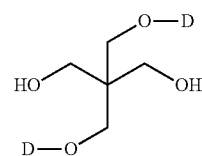

Where there is more than one bioactive moiety within the monomer-bioactive moiety conjugate (or polymer-bioactive moiety conjugate) of the invention, each bioactive moiety may be the same or different, but typically each bioactive moiety will be the same.

It will be appreciated that in the conjugates shown in Scheme 1, each of the linking groups is either a —O— or —C(O)— group. The Scheme will of course be equally applicable for other linking groups (Z) herein described.

Examples of general strategies for synthesising monomer-bioactive moiety conjugates of formula (IIa), which employ protecting group strategies and use diacid-based linking groups, are represented in Scheme 2 below (where p is an integer from eg 1 to 18, D is a releasable bioactive moiety; and D' is that part of the releasable bioactive moiety other than the hydroxyl, amine, carboxylic acid, etc):

Scheme 2: General strategies for synthesising monomer - bioactive moiety conjugates of formula (IIa)

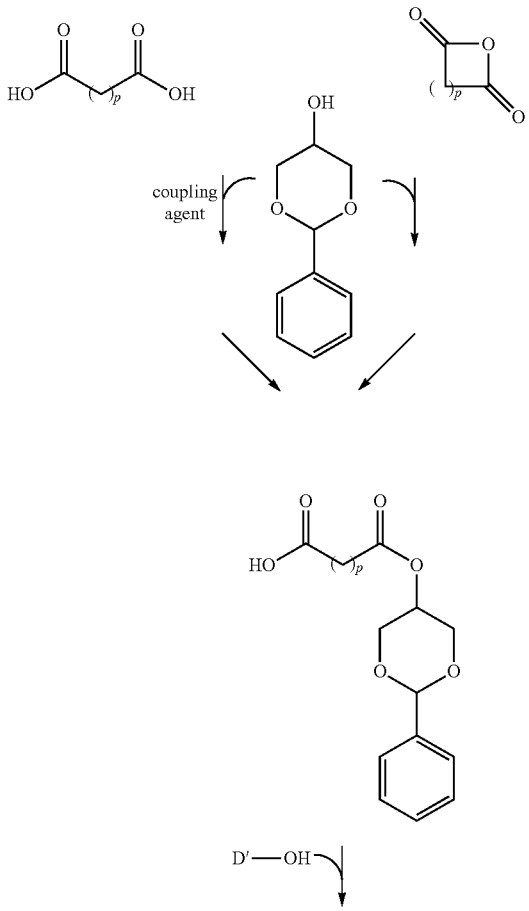

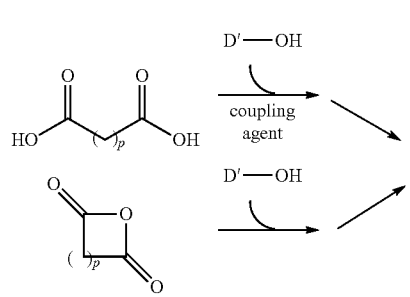

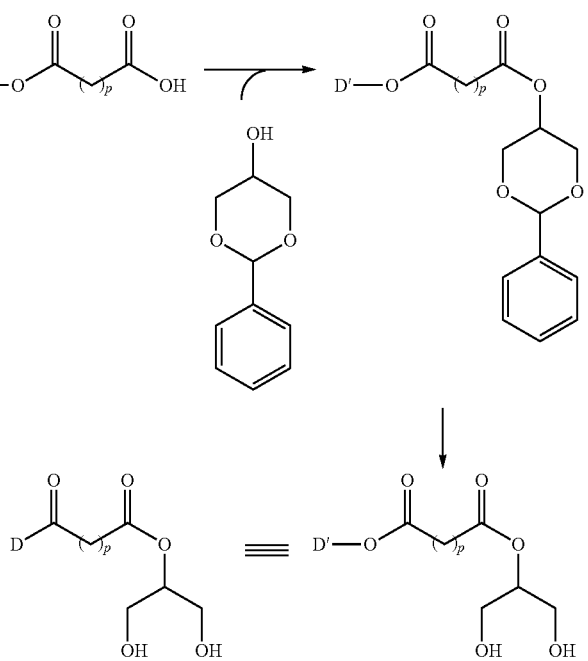

With reference to the aspect of the present invention that provides a process for the preparation of a monomer-bioactive agent conjugate of formula (IIa), Scheme 2 provides strategies for coupling compounds of formula (VI) to D and D-Z". In particular, in the synthesis of the compound of formula (IIa) denoted by:

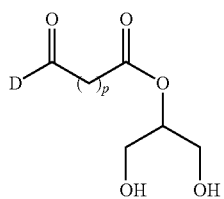

the Z group of the conjugate of formula (IIa) may be denoted by:

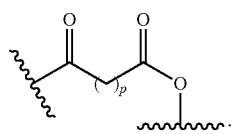

This Z group is formed through either:
i) the reaction of Z' as

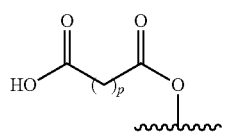

in a compound of formula (VI) with D as D'-OH; or
ii) the reaction of Z' as

in a compound of formula (VI) with D-Z" as

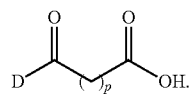

Specific examples of monomer-bioactive moiety conjugates are shown below, with the bioactive moiety being presented on the left and the monomer-bioactive moiety conjugate being presented on the right:

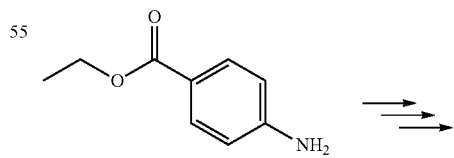

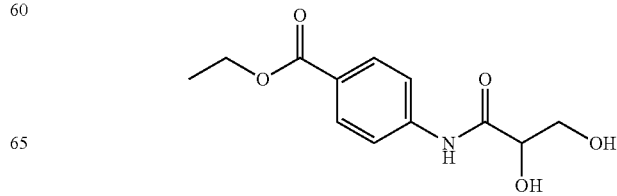

47 -continued
48 -continued
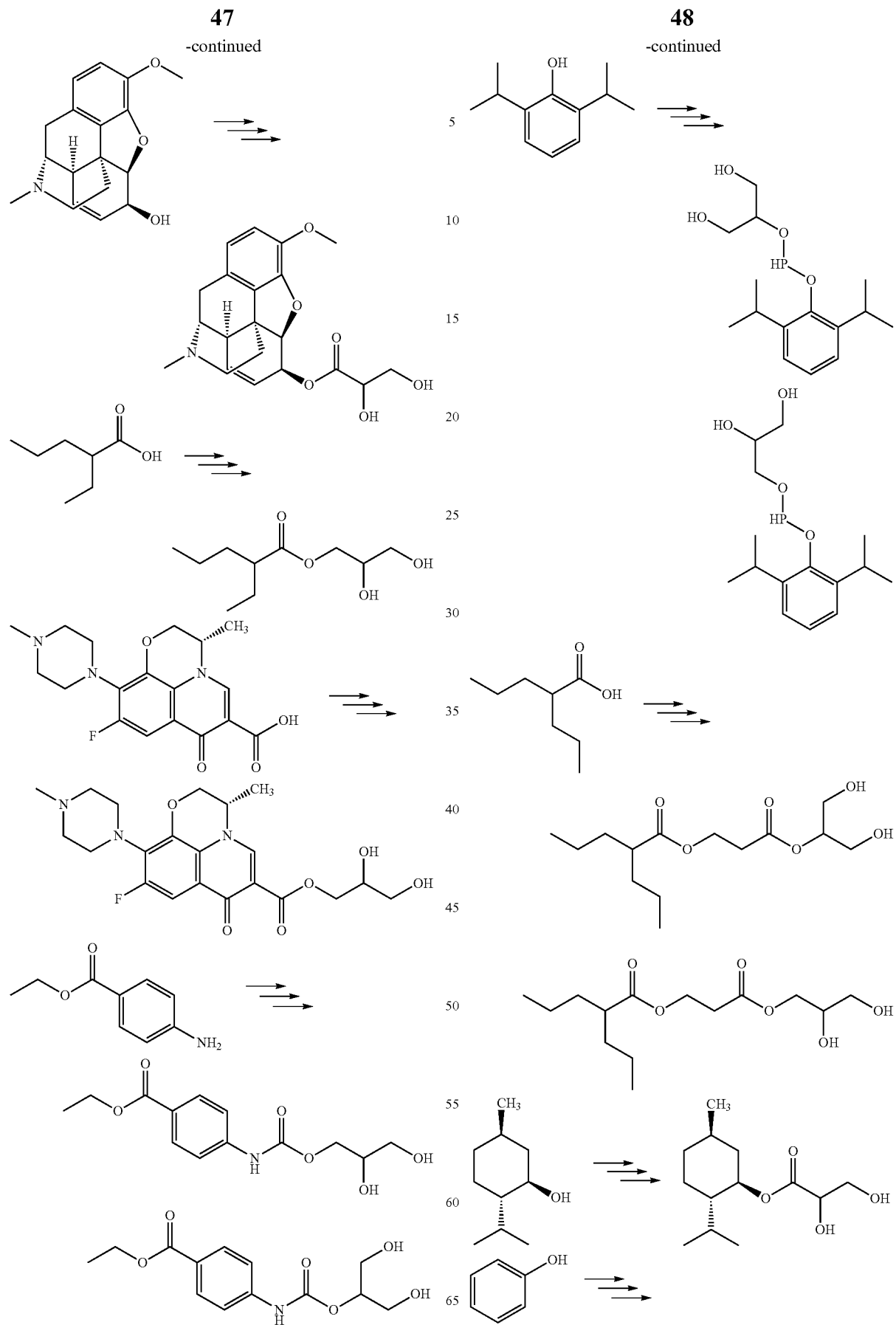

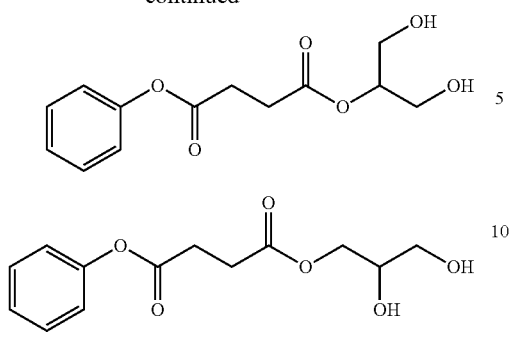

Further specific examples of monomer-bioactive moiety conjugates are shown below, with the bioactive moiety being presented on the left and the monomer-bioactive moiety conjugate being presented on the right. The acetylated latanoprost monomer-bioactive moiety conjugates (lower structures) represent examples of bioactive moieties conjugated in prodrug form such that the acetyl groups will cleave in vivo:

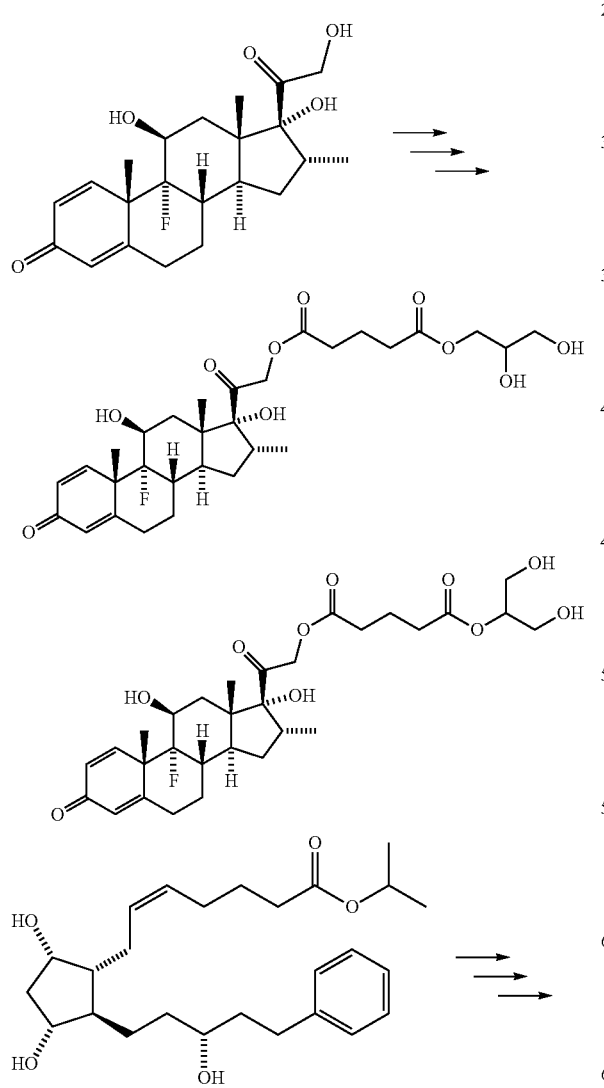

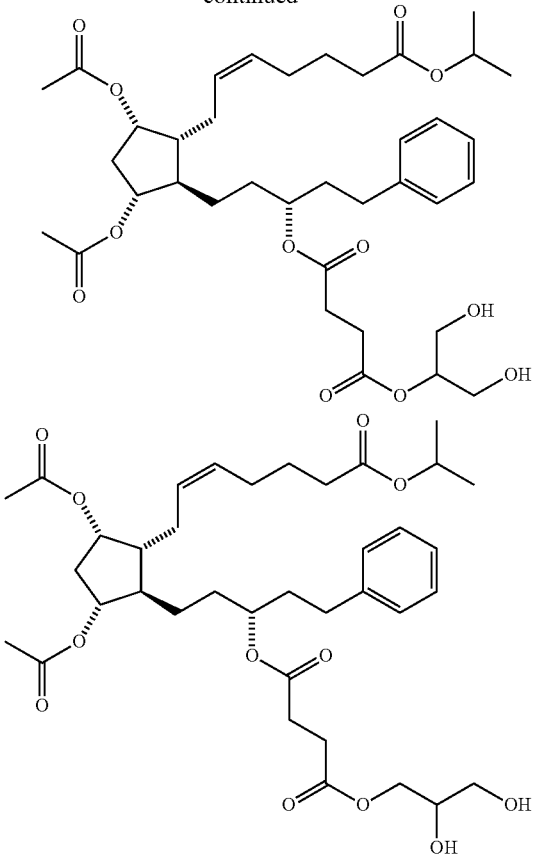

In one aspect, the invention provides a method for preparing a biodegradable polymer according to the invention, said method comprising the step of polymerising a monomer-bioactive moiety conjugate of formula (II):

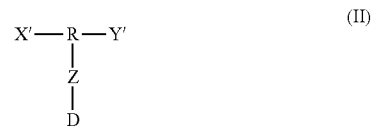

where: X', Y', R, Z and D are as herein defined; with at least one monomer comprising compatible chemical functionality.

The invention also provides a method for preparing a polymer-bioactive agent conjugate comprising as part of its polymer backbone a moiety of general formula (Id):

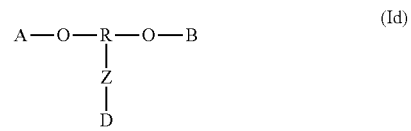

wherein:
A and B, which may be the same or different, represent the remainder of the polymer backbone and are selected from a copolymer of polyurethane and polyester;
R represents a linear or branched optionally substituted hydrocarbon;

Z is a linking group; and

D is a releasable bioactive moiety;

said process comprising the step of polymerising a monomer of formula (IIa):

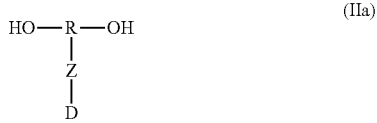

wherein:

R, Z and D are as defined above;

with at least one other monomer comprising compatible chemical functionality.

The at least one other monomer preferably comprises a compatible chemical functional group selected from the group consisting of isocyanate, carboxylic acid, carboxylic acid halide, ester, anhydride (including cyclic anhydride) groups and combinations thereof. In some embodiments the monomer of formula (II) or (IIa) is polymerised with a polyisocyanate and at least one selected from the group consisting of a polyacid, a polyester, and a polyester polyol. In one form of the invention, the monomer of formula (II) or (IIa) is polymerised with a polyisocyanate and a polyester polyol.

In a further aspect, the invention provides a method for preparing the biodegradable polymer according to the invention by providing at least one first monomer comprising at least one releasable bioactive moiety and at least one polymerisable moiety; optionally providing at least one second monomer comprising at least one polymerisable moiety reactive with at least one polymerisable moiety of said first monomer; polymerising said first monomer and optionally said second monomer optionally in the presence of one or more spacer moieties comprising two or more functionalities under conditions which are substantially non-interfering to the therapeutic efficacy of the bioactive moieties.

Techniques, equipment and reagents well known in the art can advantageously be used to prepare the polymer-bioactive moiety conjugates in accordance with the invention.

For example, polyurethanes might be prepared batch wise by mixing all components together and waiting until an exotherm occurs followed by casting the mixture into a container. The mixture can be subsequently heated to drive the reaction. When adopting this approach, the components to be mixed might first be made up into two parts before mixing: Part-1 might include a compound of general formula (II) where both X' and Y' are hydroxyl groups and one or more of: a polyol (e.g. polyester polyol), a chain extender, blowing agent (e.g. water), catalyst, and surfactants etc. Part-2 will generally comprise the polyisocyanate. Part-1 or Part-2 can also contain other additives such as fillers, pigments etc.

The polyurethanes might also be prepared as a prepolymer that is subsequently reacted with a chain extender. For example, through suitable adjustment of molar ratios, an isocyanate terminated pre-polymer may be prepared by mixing Parts-1 and -2 mentioned above. The isocyanate terminated polymer could then be reacted with a chain extender/branching molecule such as a short chain diol (e.g. 1,4-butanediol), polyol (such as a triol), a hydroxy acid (such as lactic acid or glycolic acid, or combinations thereof) or an ester containing monomer or macromonomer (such as a ester linked dimer, trimer or oligomer of two or more hydroxy acids). Alternatively, through suitable adjustment of molar ratios, the prepolymer could be produced such that it was hydroxy terminated. This hydroxy terminated prepolymer could then be reacted with a polyisocyanate to produce the desired polyurethane.

The polyurethane forming reactions can be carried out in a range of different equipment including batch kettles, static mixers, reactive injection moulders or extruders.

It also may be advantageous to heat the reagents prior to or during the reaction process to improve their solubility or to enhance their reactivity. The reaction process may also be conducted in solvent.

Suitable polyisocyanates that may be used to prepare the polymer-bioactive moiety conjugates include aliphatic, aromatic and cycloaliphatic polyisocyanates and combinations thereof. Specific polyisocyanates include, but are not limited to, diisocyanates such as m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4'diphenylmethane diisocyanate, 4,4'-biphenylene diisocyanate, 3,3'-dimethoxy-4,4'-biphenylene diisocyanate, and 3,3'-dimethyl-diphenylpropane-4,4'-diisocyanate; triisocyanates such as 2,4,6-toluene triisocyanate; higher-isocyanates such as 4,4'-dimethyl-diphenylmethane-2,2',5,5'-tetraisocyanate, polymethylene polyphenyl-polyisocyanates and alkyl esters of lysine diisocyanate (for example ethyl ester of lysine diisocyanate—ELDI); and combinations thereof. It will be appreciated that the use of polyisocyanates comprising greater than two isocyanate moieties provides for branched structures.

Polyesters might be prepared batch wise by mixing all components together with heating and continued stirring. A condensate of the reaction such as water or low molecular weight alcohol (depending if acids or esters are used as the co-monomer) can be removed by distillation. To promote further reaction produce higher molecular weight polyester the temperature may be increased and vacuum applied.

A polycondensation catalyst well known to those skilled in the art can be included in the reaction mixture to increase the rate of polymerisation.

The reaction may also be conducted in an appropriate solvent to help increase the rate of polymerisation. The solvent will generally be selected to have only minimal solubility with the condensate (e.g. water or low molecular weight alcohol). For example the reaction may be carried out in toluene and a toluene/condensate mixture distilled off continuously and the condensate allowed to separate in a Dean-Stark trap.

To further increase the molecular weight of the polyester a second stage reaction in either a wiped film reactor or a solid state reactor may be employed. The need to use such reactors will depend upon the target molecular weight as well as the suitability of the polymer for further reaction.

Suitable polyacids that may be used to prepare the polymer-bioactive moiety conjugates include aliphatic, aromatic and cycloaliphatic polyacids and combinations thereof. Specific polyacids include, but are not limited to, the following, oxalic acid, fumaric acid, maleic acid, succinic acid, glutaric acid, adipic acid, pimelic acid, suberic acid, azelaic acid, sebacic acid, phthalic acid, dodecanediacid, isophthalic acid, terephthalic acid, dodecylsuccinic acid, napthalene-2,6-dicarboxylic acid, naphthalene-2,7-dicarboxylic acid, cyclohexane dicarboxylic acid, fumaric acid, itaconic acid, malonic acid, mesaconic acid. Esters, diesters and anhydrides of the above diacids are also suitable in the process of the invention.

Where the polyesters are prepared using a carboxylic acid halide monomer, those skilled in the art will appreciate that the condensation reaction is driven by the removal of HX (where X is a halide). For example, if a di-acid chloride co-monomer is with the monomer-bioactive moiety conjugate of formula (II) where both X' and Y''' are hydroxyl groups, HCl will be liberated from the reaction. Such a reaction may be carried out in solution at an elevated temperature to drive the reaction. It is also possible to add an appropriate base to form a salt with the liberated acid halide. For example an excess of triethyl amine may be included in a reaction mixture containing a 1:1 molar ratio of a di-acid chloride co-monomer and the monomer-bioactive moiety conjugate of formula (II) where both X' and Y''' are hydroxyl groups. The reaction will afford the desired polymer-bioactive moiety conjugate and a triethyl-amine hydrochloride salt.

With all such polycondensation reactions, it is possible to some extent to control the molecular weight of the resulting polyester, its degree of branching (through control of monomer functionality) and its end group functionality by adjustment of the molar ratio's and the functionality of the monomers used in the reaction.

For example, in some instances it may be desirable to produce lower molecular weight polyesters that could be used as polymer-bioactive moiety conjugate polyester polyols for reaction with polyisocyanates and perhaps other reagents for the production of polyester-urethanes.

Additionally, it may be possible to increase the molecular weight and/or degree of branching of the polyester through the inclusion in the reaction mixture of coupling/branching agents. Examples of such coupling/branching agents include: polyepoxides, polyisocyanates, polyoxazolines. The term "poly" is used to indicate a reactive functionality of 2 or more (e.g. 2 or more epoxy groups). Having a reactive functionality of 2 will tend to produce higher molecular polymers still with a significant polyester-like character. Agents having a functionality of more than 2 will produce a branched polymer, still with significant polyester-like character.

A poly(urethane-ester) might be prepared by polymerising a diisocyanate with a hydroxy terminated polyester polyol macromer. In that case, the polyester polyol macromer will be formed from monomeric units that are coupled via a biodegradable ester moiety, and the polymerisation of it with the diisocyanate will give rise to the poly(urethane-ester) having monomeric units that are all coupled via a biodegradable urethane or ester moiety.

Suitable polyester polyols may be selected from the group consisting of polycaprolactone diol (PCLD), poly(DL lactide) (DLLA) and poly(lactic acid-co-glycolic acid) (PLGA), and combinations thereof.

A poly(ester-urethane) might be prepared by polymerising an isocyanate terminated polyurethane macromer with an ester containing monomer or macromonomer. The ester containing monomer or macromonomer may be formed from the condensation of two or more hydroxy acids. In one form, the ester containing monomer is an ester linked dimer of two hydroxy acids. Suitable hydroxy acids include lactic acid, glycolic acid, and combinations thereof. The polyurethane macromer will be formed from monomeric units that are coupled via a biodegradable urethane moiety, and the polymerisation of it with the ester containing monomer or macromonomer will give rise to the poly(ester-urethane) having monomeric units that are all coupled via a biodegradable urethane or ester moiety.

As discussed in more detail in the Example section below, the synthesis monomer bioactive moiety conjugates typically required the optimization of reaction conditions and the alteration of known purification methodologies. The desired hydrolytic instability of the monomer bioactive moiety conjugates restricted the usage of several traditional purification methodologies and made the development of alternative pathways necessary.

The presence of any impurities in the monomer bioactive moiety conjugates can also affect the molecular weight, and structure of the final polymer as well as the release rate of the bioactive moiety from the polymer conjugate.

Further, the use of the monomer bioactive moiety conjugates in the formation of the polymers in some cases required specific polymerisation methodology to be developed to allow the efficient incorporation of the monomer bioactive moiety conjugates into the polymer. This included selection of appropriate solvents/heating/mixing/catalyst/order of monomer additions etc to allow the incorporation of the monomer bioactive moiety conjugates as well as to minimise the amount of degradation or premature release of the bioactive moiety.

Careful selection of co-monomers/reaction conditions etc may also be required for a given monomer bioactive moiety conjugate in order to produce a polymer conjugate with appropriate bioactive moiety loading as well as have mechanical properties, bioactive moiety release rate, formability etc.

Additionally, methods were developed to remove impurities from the polymer bioactive moiety conjugates in order provide control of the release rate of the bioactive moiety from the polymer conjugate.

Irrespective of the manner in which the biodegradable polymer-bioactive moiety conjugates are prepared, as discussed above all repeat units that make up the polymer backbone will be coupled via a biodegradable moiety. Accordingly, any monomer or macromer used in the preparation of the conjugates shall not contain repeat units that are coupled by a non-biodegradable moiety such as an ether.

While the use of polyether segments can provide desirable improvements in the flexibility and in some cases can provide an improvement in the desired rate of release of the bioactive the release of polyethers having a molecular weight below 1000 g/mol can result in increased toxicity from the degradation products.

In most cases it is possible to use polyester polyols such as polycaprolactone diol to also provide desired increase in the flexibility of the polymer as well as providing improvements in the release of the bioactive agent. However, the polyester polyols can advantageously degrade into more benign monomeric components.

Additionally the use of polyester polyols such as DLLA (DL lactide) or PLGA (poly(lactic-co-glycolic acid)) can provide an increase rate of degradation of the polymer as well as release of the drug through the autocatalytic effect of the released acidic components.

The biodegradable polymer may be formed and delivered as a liquid/wax that can be injected, polymerised, cured, set or solidified in situ.

In one embodiment, the methods of the invention allow the formation of biodegradable moieties with multiple bioactive moieties, known loadings, evenly distributed bioactive moieties in the polymer chain, predetermined relative proportions and predetermined relative positions.

Scheme 3 illustrates the method with a valproic acid-polyurethane conjugate.

Scheme 3: Valproic acid-polyurethane conjugate

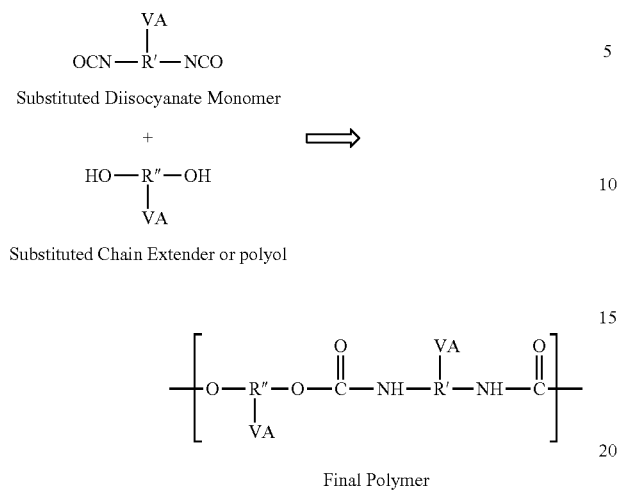

Substituted Diisocyanate Monomer

+

Substituted Chain Extender or polyol

Final Polymer

VA: Valporic Acid (Drug)
R', R': Organic groups
(same or different)

Scheme 4 illustrates the method with a ciprofloxacin-polyurethane conjugate.

Scheme 4: Ciprofloxacin-polyurethane conjugate

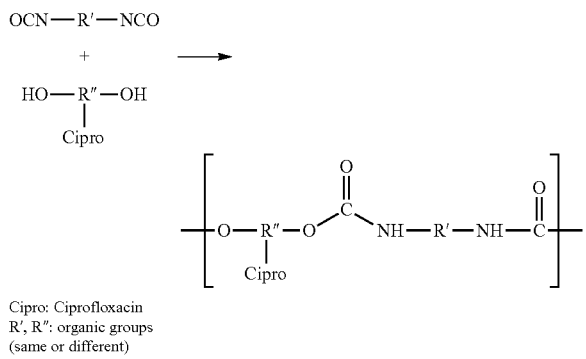

Cipro: Ciprofloxacin
R', R": organic groups
(same or different)

Schemes 5 and 6 illustrate the method with a ciprofloxacin-polyester conjugate and a valproic acid-polyester conjugate respectively.

Scheme 5: Ciprofloxacin-polyester conjugate

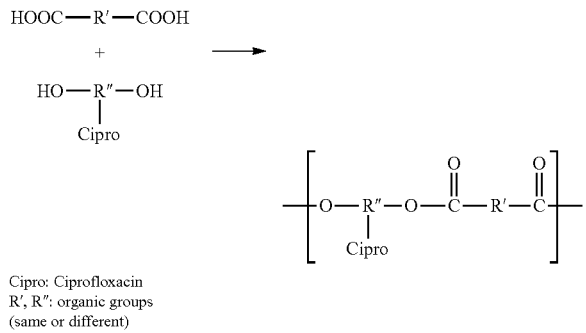

Cipro: Ciprofloxacin
R', R": organic groups
(same or different)

Scheme 6: Valproic acid-polyester conjugate

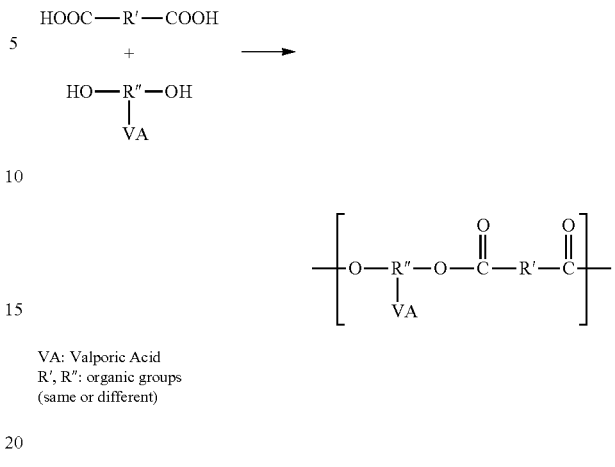

VA: Valporic Acid
R', R": organic groups
(same or different)

The composition of the polymer can be advantageously altered to incorporate other monomers to provide appropriate polymer properties to suit a particular application (e.g. hydrophobicity, structural strength, rate of release of bioactive moieties).

A further advantage is that side chain and end functional attachment of the bioactive moiety to the polymer (by control of the monomer structure) allows the control of the polymer mechanical and other properties. In this sense the polymer therapeutic can be viewed and used as a scaffold.

In a further aspect the control of the mechanical properties in that the bioactive moiety attached to the polymer may have different mechanical/surface properties in the bioactive moiety attached state compared to when the bioactive moiety is not attached, i.e., (i) as the bioactive moiety is released the polymer may alter in properties and (ii) forming a polymer from monomers functionalised with bioactive moieties may have different (more desirable) properties compared to an analogous polymer without bioactive moiety functionalisation (i.e., bioactive moiety functionalisation breaks up the crystallinity to produce a more flexible polymer).

The physical properties of final material can be altered through changing the composition of the polymer backbone.

The biodegradable polymers of the present invention may be blended with one or more other polymers (generally biodegradable polymers).

The present invention also provides a monomer comprising: a) one or more releasable bioactive moieties; b) one or more polymerisable moieties; wherein one or more of the releasable bioactive moieties are capable of being released from the monomer before or after polymerisation under conditions which are non-interfering to the therapeutic efficacy of the bioactive moieties.

The skilled artisan would be able to select suitable chemistry so as protect other functionalities on the bioactive moieties during attachment to the spacer or monomer during or after polymerisation.

There follows potential Schemes 7 and 8 for the protection/deprotection and breakdown of polymer-bioactive moiety conjugates of the invention. Examples are illustrated for Ciprofloxacin attached to a polyurethane or to a polyester.

Scheme 7: Example shown for polyurethane formed from the reaction of a diol and a diisocyanate, where the bioactive molecule (e.g., Ciprofloxacin) is attached to one of the monomers (to the diol monomer in this case).

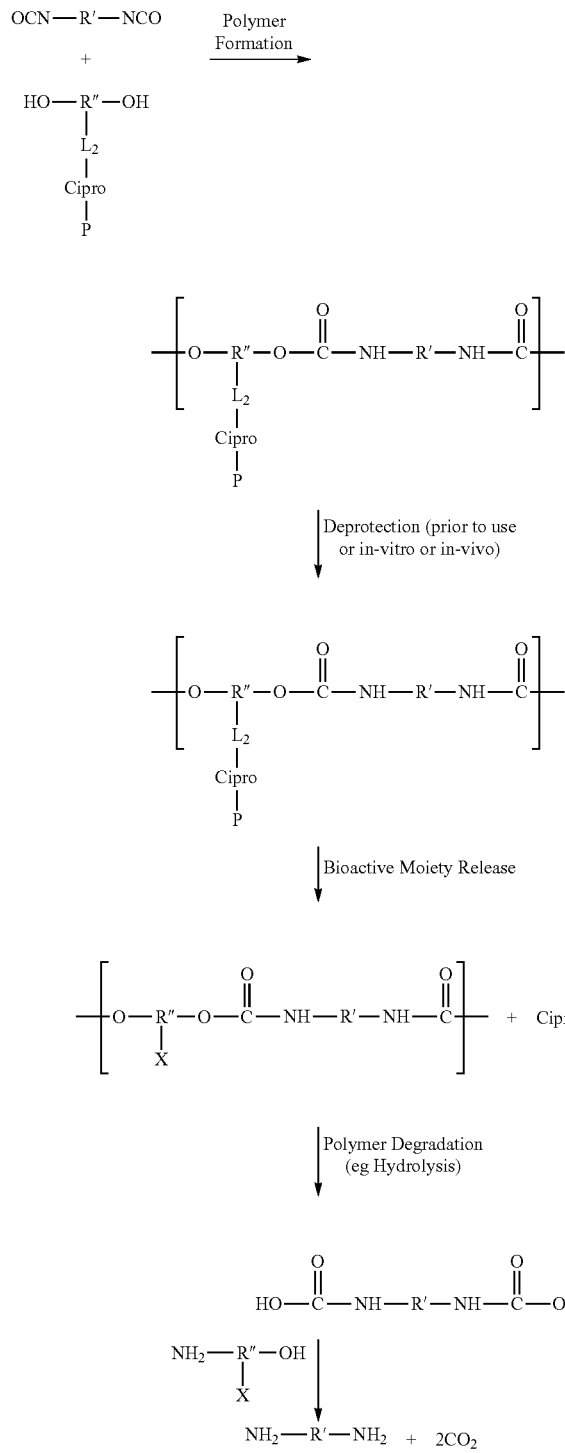

L2 = biodegradable moiety,
P = protection group
Rate of breakdown P >= L2
Cipro = Ciprofloxacin
R', R" = organic groups (same or different)
Rate of Cipro release >= rate of polymer breakdown
X = product from cleavage of linker L2 For an ester linkage of Ciprofloxacin X would be an OH Scheme 8: Example shown for polyester formed from the reaction of a diol and a diacid, where the bioactive molecule (e.g., Ciprofloxacin) is attached to one of the monomers (to the diol monomer in this case).

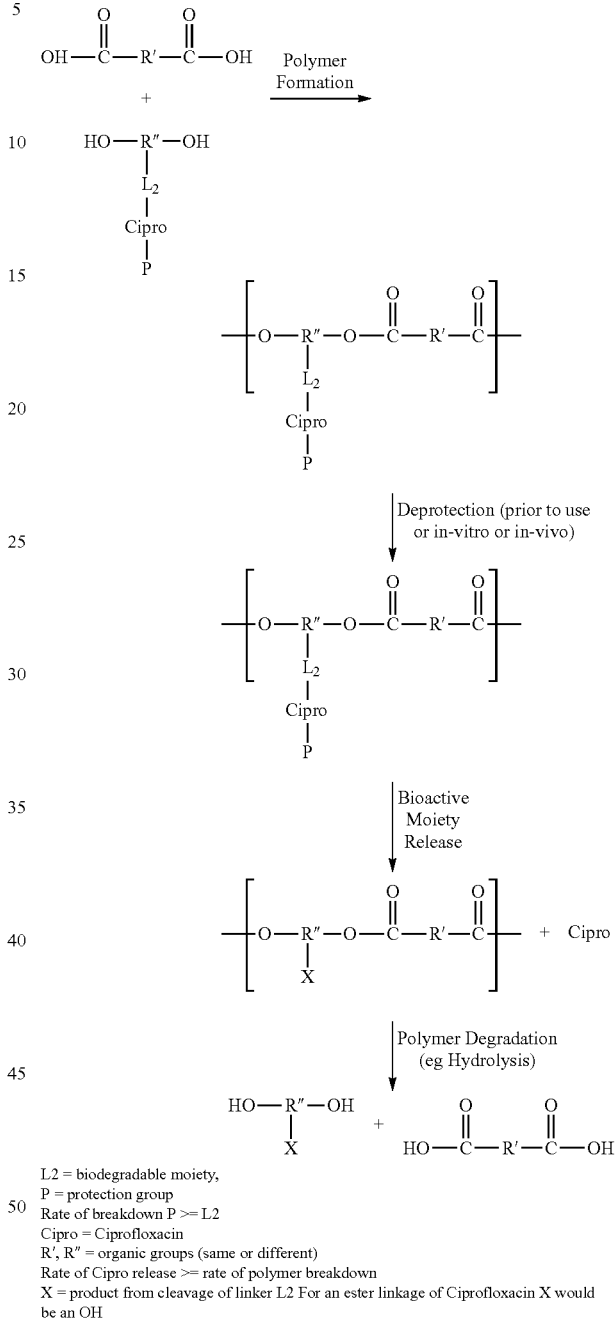

L2 = biodegradable moiety,
P = protection group
Rate of breakdown P >= L2
Cipro = Ciprofloxacin
R', R" = organic groups (same or different)
Rate of Cipro release >= rate of polymer breakdown
X = product from cleavage of linker L2 For an ester linkage of Ciprofloxacin X would be an OH In one embodiment a biodegradable polymer of the present invention may be prepared by the polymerisation of a hydroxy functionalised ester of valproic acid and a diisocyanate in the presence of a suitable catalyst.

A biodegradable polymer of the present invention may also be prepared by the polymerisation of a dihydroxy functionalised ester of valproic acid, 2,3-dihydroxypropyl-2-propylpentanoate, with hexamethyldiisocyanate in the presence of a suitable catalyst.

In a further aspect there is provided a functionalised biodegradable polymer comprising a plurality of labile bioactive moieties pendant from and chemically bonded to a polymer backbone wherein the rate of bioactive moiety release from the polymer backbone is equal to or faster than the rate of polymer backbone breakdown and wherein the polymer backbone is substantially degradable.

The biodegradable polymers in accordance with the invention can be incorporated or made into coatings and scaffolds for target in vitro and in vivo applications in a variety of ways.

For example, the biodegradable polymers of the invention may be used in the manufacture of sutures, dental devices, orthopaedic fixation devices, transdermal patches, ligating clips, vascular grafts, stents, and tissue-engineering scaffolds. The polymers may be applied to the outside or inside of the body of the subject in need of treatment.

In one embodiment, the biodegradable polymers of the invention may be used in the manufacture of an ocular implant. In some embodiments, the ocular implant comprises a biodegradable polymer as described herein, where the bioactive moiety is a fluoroquinolone antibiotic. Preferred fluoroquinoline antibiotics include levofloxacin and moxifloxacin.

The present invention also provides a method for treating an eye condition in a subject by administering a biodegradable polymer as described herein to the subject, where the bioactive moiety is selected from fluoroquinoline antibiotics. The eye condition may be an eye infection. In one form of the invention, the biodegradable polymer is administered in an ocular implant. For the effective treatment of an eye infection, it would be desirable for the biodegradable polymer to release an amount of fluoroquinolone antibiotic selected from the group consisting of at least 5 µg/24 hours, at least 10 µg/24 hours, at least 15 µg/24 hours, and at least 20 µg/24 hours. Preferred fluoroquinoline antibiotics include levofloxacin and moxifloxacin.

Coatings containing the biodegradable polymers can advantageously be directly produced using techniques well known in the art including: solution casting, spray coating, melt pressing, transfer moulding, lamination, moulding onto a premade film containing the conjugate, rotomoulding, spin coating, extrusion coating, electrospinning etc.

Premade films for use in subsequent application as coatings can advantageously also be produced using techniques well known in the art including: film extrusion, film blowing, tentering etc.

The premade films may be applied as coatings by: melt pressing, vacuum forming, thermoforming, transfer lamination, adhesive bonding.

Coatings may be included as films, multilayer films, non-uniform or graded coatings as dots, patterns or structures according to some form of mask or template.

Three dimensional scaffolds containing the polymer-bioactive moiety conjugate(s) can also be formed in a number of means including:

Fibre based structures which in turn are knitted, woven, spunbonded or formed into non-woven mats etc. Additionally, fibre structures could be formed with a binder resin into composite structures. The fibres could be formed by melt extrusion, wet spinning or the bioactive conjugate could be over-coated or dispersed within fibres by bicomponent fibre extrusion, dip or spray coating etc.

Moulded structures could be produced by injection moulding, blow moulding, reactive injection moulding, casting or moulding with subsequent machining etc.

Porous structures could be made by moulding/extrusion in the presence of the porogen. Additionally porous 3D structures could be produced by moulding or polymerisation in the presence of an extractable material. For example, a polyurethane containing the monomer-bioactive moiety conjugate or polymer-bioactive moiety conjugate could be formed by casting around a sufficient content of polystyrene beads. The polystyrene beads could be removed by extraction with an appropriate solvent.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

In some embodiments, it may be desirable that a group (for example the R group) is optionally substituted with a polymer chain. An example of such a polymer chain includes a polyester, polyurethane, or copolymers thereof. Such a polymer chain may, or may not, have one or more bioactive moieties appended thereto. For example, the R group of the formulae disclosed herein may be substituted with a polymer chain. The skilled worker will recognise that the R group may therefore represent a point of branching of the polymer backbone within the polymer-bioactive moiety conjugate of the present invention. If R is substituted with a polymer chain, that polymer chain should also be biodegradable and not contain any repeat units that are coupled with a non-biodegradable moiety as described herein.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro $OC(O)C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro $OC(O)C_{1-6}$ alkyl, and amino), phenoxy (wherein phenyl itself may be further substituted e.g., by $C_{1-6}$ alkyl, halo, hydroxy, hydroxy$C_{1-6}$alkyl, $C_{1-6}$alkoxy, halo$C_{1-6}$ alkyl, cyano, nitro $OC(O)C_{1-6}$ alkyl, and amino), benzyloxy (wherein benzyl itself may be further substituted e.g., by $C_{1-6}$ alkyl, halo, hydroxy, hydroxy$C_{1-6}$alkyl, $C_{1-6}$alkoxy, halo$C_{1-6}$ alkyl, cyano, nitro $OC(O)C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. $NHC(O)CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$ alkyl, and amino), nitro, formyl, —C(O)-alkyl (e.g. $C_{1-6}$ alkyl, such as acetyl), O—C(O)-alkyl (e.g. $C_{1-6}$ alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro $OC(O)C_{1-6}$alkyl, and amino), replacement of $CH_2$ with C═O, $CO_2H$, $CO_2$ alkyl (e.g. $C_{1-6}$ alkyl such as methyl ester, ethyl ester, propyl ester, butyl ester), $CO_2$-phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro $OC(O)C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro $OC(O)C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro $OC(O)C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl) aminoalkyl (e.g., HN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkylO$_2$CC$_{1-6}$ alkyl-), amidoalkyl (e.g., $H_2N(O)CC_{1-6}$ alkyl-, $H(C_{1-6}$ alkyON(O)CC$_{1-6}$ alkyl-), formylalkyl (e.g., OHCC$_{1-6}$alkyl-), acylalkyl (e.g., $C_{1-6}$ alkyl(O)CC$_{1-6}$ alkyl-), nitroalkyl (e.g., $O_2NC_{1-6}$ alkyl-), sulfoxidealkyl (e.g., $R^3(O)SC_{1-6}$ alkyl, such as $C_{1-6}$ alkyl(O)SC$_{1-6}$ alkyl-), sulfonylalkyl (e.g., $R^3(O)_2SC_{1-6}$ alkyl- such as $C_{1-6}$ alkyl(O)$_2$SC$_{1-6}$ alkyl-), sulfonamidoalkyl (e.g., $_2$HRN(O)SC$_{1-6}$ alkyl, $H(C_{1-6}$ alkyl)N (O)SC$_{1-6}$ alkyl-).

As used herein, the term "alkyl", used either alone or in compound words denotes straight chain, branched or cyclic alkyl, for example $C_{1-40}$ alkyl, or $C_{1-20}$ or $C_{1-10}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl, tridecyl, tetradecyl, pentadecyl, hexadecyl, heptadecyl, octadecyl, nonoadecyl, eicosyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

As used herein, term "alkenyl" denotes groups formed from straight chain, branched or cyclic hydrocarbon residues containing at least one carbon to carbon double bond including ethylenically mono-, di- or polyunsaturated alkyl or cycloalkyl groups as previously defined, for example $C_{2-40}$ alkenyl, or $C_{2-20}$ or $C_{2-10}$. Thus, alkenyl is intended to include propenyl, butylenyl, pentenyl, hexaenyl, heptaenyl, octaenyl, nonaenyl, decenyl, undecenyl, dodecenyl, tridecenyl, tetradecenyl, pentadecenyl, hexadecenyl, heptadecenyl, octadecenyl, nondecenyl, eicosenyl hydrocarbon groups with one or more carbon to carbon double bonds. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined, for example, $C_{2-40}$ alkenyl, or $C_{2-20}$ or $C_{2-10}$. Thus, alkynyl is intended to include propynyl, butylynyl, pentynyl, hexaynyl, heptaynyl, octaynyl, nonaynyl, decynyl, undecynyl, dodecynyl, tridecynyl, tetradecynyl, pentadecynyl, hexadecynyl, heptadecynyl, octadecynyl, nondecynyl, eicosynyl hydrocarbon groups with one or more carbon to carbon triple bonds. Examples of alkynyl include ethynyl, 1-propynyl, 2-propynyl, and butynyl isomers, and pentynyl isomers. An alkynyl group may be optionally substituted by one or more optional substituents as herein defined.

An alkenyl group may comprise a carbon to carbon triple bond and an alkynyl group may comprise a carbon to carbon double bond (i.e. so called ene-yne or yne-ene groups).

As used herein, the term "aryl" (or "carboaryl") denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may be optionally substituted by one or more optional substituents as herein defined.

As used herein, the terms "alkylene", "alkenylene", and "arylene" are intended to denote the divalent forms of "alkyl", "alkenyl", and "aryl", respectively, as herein defined.

The term "halogen" ("halo") denotes fluorine, chlorine, bromine or iodine (fluoro, chloro, bromo or iodo). Preferred halogens are chlorine, bromine or iodine.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, and furazanyl.

The term "acyl" either alone or in compound words denotes a group containing the agent C=O (and not being a carboxylic acid, ester or amide) Preferred acyl includes C(O)—$R^x$, wherein $R^x$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexanoyl; and heterocyclicglyoxyloyl such as thiazolyglyoxyloyl and thienylglyoxyloyl. The $R^x$ residue may be optionally substituted as described herein.

The term "sulfoxide", either alone or in a compound word, refers to a group —S(O)$R^y$ wherein $R^y$ is selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl.

The term "sulfonyl", either alone or in a compound word, refers to a group $S(O)_2$—$R^y$, wherein $R^y$ is selected from hydrogen, alkyl, alkenyl, alkynyl, aryl, heteroaryl, heterocyclyl, carbocyclyl and aralkyl. Examples of preferred $R^y$ include $C_{1-20}$alkyl, phenyl and benzyl.

The term "sulfonamide", either alone or in a compound word, refers to a group S(O)N$R^y R^y$ wherein each $R^y$ is independently selected from hydrogen, alkyl, alkenyl, alkynyl, aryl, heteroaryl, heterocyclyl, carbocyclyl, and aralkyl. Examples of preferred $R^y$ include $C_{1-20}$alkyl, phenyl and benzyl. In a preferred embodiment at least one $R^y$ is hydrogen. In another form, both $R^y$ are hydrogen.

The term, "amino" is used here in its broadest sense as understood in the art and includes groups of the formula $NR^A R^B$ wherein $R^A$ and $R^B$ may be any independently selected from hydrogen, alkyl, alkenyl, alkynyl, aryl, carbocyclyl, heteroaryl, heterocyclyl, aralkyl, and acyl. $R^A$ and $R^B$, together with the nitrogen to which they are attached, may also form a monocyclic, or polycyclic ring system e.g. a 3-10 membered ring, particularly, 5-6 and 9-10 membered systems. Examples of "amino" include $NH_2$, NHalkyl (e.g. $C_{1-20}$alkyl), NHaryl (e.g. NHphenyl), NHaralkyl (e.g. NHbenzyl), NHacyl (e.g. $NHC(O)C_{1-20}$alkyl, NHC(O)phenyl), Nalkylalkyl (wherein each alkyl, for example $C_{1-20}$, may be the same or different) and 5 or 6 membered rings, optionally containing one or more same or different heteroatoms (e.g. O, N and S).

The term "amido" is used here in its broadest sense as understood in the art and includes groups having the formula $C(O)NR^A R^B$, wherein $R^A$ and $R^B$ are as defined as above. Examples of amido include $C(O)NH_2$, C(O)NHalkyl (e.g. $C_{1-20}$alkyl), C(O)NHaryl (e.g. C(O)NHphenyl), C(O)NHaralkyl (e.g. C(O)NHbenzyl), C(O)NHacyl (e.g. $C(O)NHC(O)C_{1-20}$alkyl, C(O)NHC(O)phenyl), C(O)Nalkylalkyl (wherein each alkyl, for example $C_{1-20}$, may be the same or different) and 5 or 6 membered rings, optionally containing one or more same or different heteroatoms (e.g. O, N and S).

The term "carboxy ester" is used here in its broadest sense as understood in the art and includes groups having the formula $CO_2 R^z$, wherein $R^z$ may be selected from groups including alkyl, alkenyl, alkynyl, aryl, carbocyclyl, heteroaryl, heterocyclyl, aralkyl, and acyl. Examples of carboxy ester include $CO_2 C_{1-20}$alkyl, $CO_2$aryl (e.g. $CO_2$-phenyl), $CO_2$aralkyl (e.g. $CO_2$ benzyl).

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

It is understood that the compounds of the present invention (including monomers and polymers) may exist in one or more stereoisomeric forms (eg enantiomers, diastereomers). The present invention includes within its scope all of these stereoisomeric forms either isolated (in for example enantiomeric isolation), or in combination (including racemic mixtures).

The following examples are intended to illustrate the scope of the invention and to enable reproduction and comparison. They are not intended to limit the scope of the disclosure in any way.

EXAMPLES

General

Proton NMR spectra were obtained on Bruker AV400 and Bruker AV200 spectrometers, operating at 400 MHz and 200 MHz respectively. All spectra were obtained at 23° C. unless specified. Chemical shifts are reported in parts per million (ppm) on the δ scale and relative to the chloroform peak at 7.26 ppm (1H). Oven dried glassware was used in all reactions carried out under an inert atmosphere (either dry nitrogen or argon). All starting materials and reagents were obtained commercially unless otherwise stated. Removal of solvents "under reduced pressure" refers to the process of bulk solvent removal by rotary evaporation (low vacuum pump) followed by application of high vacuum pump (oil pump) for a minimum of 30 min. Analytical thin layer chromatography (TLC) was performed on plastic-backed Merck Kieselgel KG60F254 silica plates and visualised using short wave ultraviolet light, potassium permanganate or phosphomolybdate dip. Flash chromatography was performed using 230-400 mesh Merck Silica Gel 60 following established guidelines under positive pressure. Tetrahydrofuran and dichloromethane were obtained from a solvent dispensing system under an inert atmosphere. All other reagents and solvents were used as purchased.

Molecular weights of polymers were characterized by gel permeation chromatography (GPC) performed in tetrahydrofuran (THF) or dimethylformamide (DMF) 1.0 mL/min, 25° C. using a Waters GPC instrument, with a Waters 2414 Refractive Index Detector, a series of four Polymer Laboratories PLGel columns (3×5 µm Mixed-C and 1×3 µm Mixed-E), and Empower Pro Software. The GPC was calibrated with narrow polydispersity polystyrene standards (Polymer Laboratories EasiCal, MW from 264 to 256000), and molecular weights are reported as polystyrene equivalents.

Acid number and hydroxy number were performed using the methods outlined below

Valproic Acid (2-propylpentanoic Acid)

Example 1

Valproic Acid Monoglyceride (VA-MG)—For comparative Examples (a) 2-propylpentanoic acid, 2,2-dimethyl-1,3-dioxolane-4-yl methyl ester

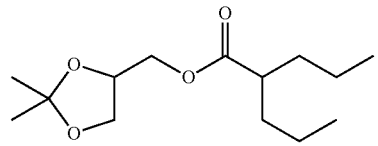 [SMILES: CCCC(CCC)C(=O)OCC1COC(C)(C)O1]

2-propylpentanoic acid (10.00 g; 0.07 mol) was dissolved in dichloromethane (anhydrous) (500 ml), under an argon atmosphere. 2,2-dimethyl-1,3-dioxolane-4-methanol (solketal) (11.00 g; 0.08 mol; 1.2 equiv) and p-dimethylaminopyridine (1.02 g; 8.30 mmol; 0.12 equiv) were added. The solution was cooled to 0° C. and a solution of 1,3-dicyclohexylcarbodiimide (17.17 g; 0.08 mol; 1.20 equiv) in dichloromethane (anhydrous) (100 ml) was added dropwise over 30 minutes. A white precipitate formed during the addition. The reaction mixture was allowed to warm to ambient temperature and stirred at ambient temperature for 16 hours. The reaction mixture was cooled in a dry ice/acetone bath (−78° C.) followed by filtration to remove the urea precipitate. The solvent was removed in vacuo to obtain the crude product as a clear, colourless oil (23.29 g) which was purified by column chromatography (silica gel, 5% ethyl acetate/petroleum ether 40-60) to obtain a colourless oil (14.40 g, 80%).

¹H-NMR (CDCl₃, 200 MHz): δ[ppm]=4.30 (quintet, 1H, J=5.8 Hz); 4.03-4.17 (m, 3H); 3.74 (dd, 1H, J=6.1 Hz, J=8.3 Hz); 2.34-2.47 (m, 1H); 1.19-1.69 (m, 14H); 0.89 (t, 6H, J=7.1 Hz)

(b) 2,3-dihydroxypropyl 2-propylpentanoate (VA-MG)

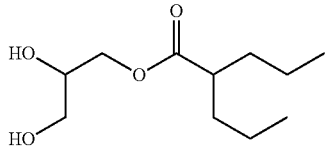

2-propylpentanoic acid 2,2-dimethyl-1,3-dioxolane-4-yl methyl ester was dissolved in 95% (v/v) aqueous ethanol (200 ml). Amberlyst 15 (wet) ion exchange resin (sulfonic acid) (6.40 g) and antibumping granules were added. The reaction mixture was refluxed for 5 hours without stirring. The reaction mixture was cooled to ambient temperature, followed by filtration and removal of the solvent in vacuo to obtain a pale brown oil (12.89 g) which was purified by column chromatography (silica gel, 50% ethyl acetate/petroleum ether 40-60) to obtain a colourless oil (10.40 g, 86%).

¹H-NMR (CDCl₃, 200 MHz): δ[ppm]=4.27-4.11 (m, 2H); 3.80-4.01 (m, 1H); 3.52-3.76 (m, 2H); 2.52 (d, 1H, J=5.0 Hz); 2.34-2.49 (m, 1H); 2.09 (t, 1H, J=6.0 Hz); 1.20-1.70 (8H); 0.90 (t, 6H, J=6.9 Hz)

Example 2

3-(1,3-dihydroxypropan-2-yloxy)-3-oxopropyl 2-propylpentanoate a) 3-hydroxypropyl 2-propylpentanoate

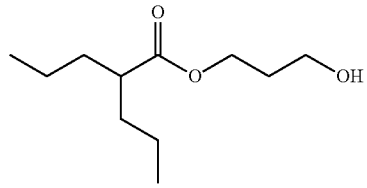

2-propylpentanoic acid (10.0 g, 69.3 mmol) was mixed with propane-1-3-diol (42.1 g, 555.0 mmol) and methyl-sulfonic acid (5 drops) in toluene (200 ml) and the mixture was heated under reflux using a Dean Stark trap for 12 h. After that, toluene was removed under reduced pressure and the crude mixture was dissolved in dichloromethane (200 ml) and extracted with water (pH 5, 3×200 ml). The combined organic layers were dried over sodium sulfate and the volatiles were removed under reduced pressure giving a clear oil (14.0 g, 60.0 mmol, 99%).

¹H-NMR (CDCl₃, 200 MHz): δ[ppm]=4.24 (tr, 2H, J=6.1 Hz), 3.68 (tr, 2H, J=6.1 Hz), 2.37-2.31 (m, 1H), 1.93-1.77 (m, 2H), 1.69-1.16 (m, 8H), 0.89 (tr, 6H, 6.9 Hz)

b) 3-(2-propylpentanoyloxy)propanoic acid

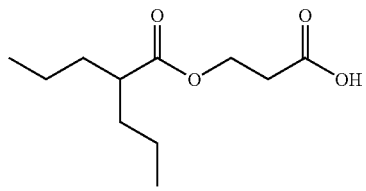

3-hydroxypropyl 2-propylpentanoate (2.08 g, 10.3 mmol) was dissolved in 120 ml of acetone. 3.1 ml of a solution of Jones Reagent (prepared by dissolving 26.72 g of chromium trioxide in 23 ml of concentrated sulfuric acid, and then diluting the mixture to 100 ml with water) was added. Propan-2-ol (5 ml) was added to the reaction mixture which was filtered through a pad of celite. The filtrate was washed with 0.01M HCl solution (3×50 ml), dried over sodium sulfate, filtered and concentrated under reduced pressure. The crude product (2.05 g, 9.5 mmol, 92%) was used in the next step without any further purification.

¹H-NMR (CDCl₃, 200 MHz): δ[ppm]=4.35 (tr, 2H, J=6.3 Hz), 2.70 (tr, 2H, J=6.3 Hz), 2.47-2.28 (m, 1H), 1.70-1.15 (m, 8H), 0.88 (tr, 6H, J=6.9 Hz)

c) 3-oxo-3-(2-phenyl-1,3-dioxan-5-yloxy)propyl 2-propylpentanoate

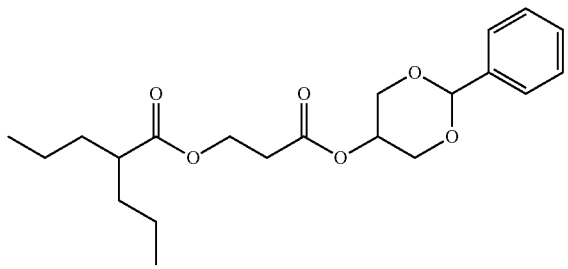 [SMILES: CCCC(CCC)C(=O)OCCC(=O)OC1COC(c2ccccc2)OC1]

3-(2-propylpentanoyloxy)propanoic acid (2.05 g, 9.5 mmol) was dissolved in anhydrous CH₂Cl₂ (200 ml) under argon. 1,3-O-benzylideneglycerol (2.50 g, 13.67 mmol triethylamine (4.04 g, 40.0 mmol) and O-benzotriazol-1-yl-N,N,N',N'-trimethyluronium hexafluorophosphate (4.2 g, 11.0 mmol) were added successively. The reaction mixture was stirred under argon for 72 h. The reaction mixture was washed with saturated NaHCO₃ solution (1×90 ml), water (1×90 ml) and dried over Na₂SO₄. The organic solvent was removed under reduced pressure giving a pale, pink solid (2.99 g, 7.9 mmol, 83%).

$^1$H-NMR (CDCl$_3$, 200 MHz): δ[ppm]=7.63-7.29 (m, 5H), 5.55 (m, 5H), 4.75-4.66 (m, 1H), 4.42-4.06 (m, 4H), 3.01-2.78 (m, 2H), 2.74-2.24 (m, 3H), 2.07-1.18 (m, 8H), 0.92 (tr, 6H, J=6.9 Hz)

d) 3-(1,3-dihydroxypropan-2-yloxy)-3-oxopropyl 2-propylpentanoate

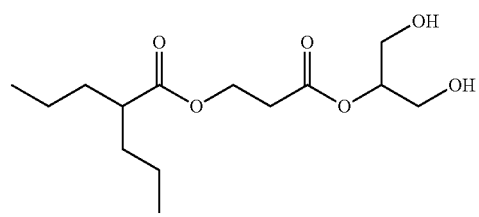 [SMILES: CCCC(CCC)C(=O)OCCC(=O)OC(CO)CO]

3-oxo-3-(2-phenyl-1,3-dioxan-5-yloxy)propyl 2-propylpentanoate (2.99 g, 7.9 mmol) was dissolved in ethanol (90 ml) under argon. Palladium catalyst (10 wt % Pd/C) (300 mg) was added, the flask was evacuated and allowed to stir 1 atm of hydrogen gas at room temperature for 16 hours. The crude reaction mixture was passed through a glass microfiber on a sintered funnel. The volatiles were removed under reduced pressure yielding 2.01 g (6.95 mmol, 88%) of a clear oil. The product was used without any further purification $^1$H-NMR (CDCl$_3$, 400 MHz): δ[ppm]=4.99-4.90 (m, 1H), 3.86-3.80 (m, 4H), 2.80-2.70 (m, 2H), 2.48-2.37 (m, 2H), 1.89-1.80 (m, 2H), 1.68-1.54 (m, 2H), 1.50-1.22 (m, 6H), 0.91 (tr, 6H, J=7.2 Hz)

Example 3

Production of a mixture of 1,2-dihydroxy-5,14-di-oxo-4,15-dioxa-6,13-diazanonadecan-19-yl 2-propylpentanoate and 1-hydroxy-2-(hydroxymethyl)-4,13-dioxo-3,14-dioxa-5,12-diazaoctadecan-18-yl 2-propylpentanoate a) 4-hydroxybutyl 2-propylpentanoate

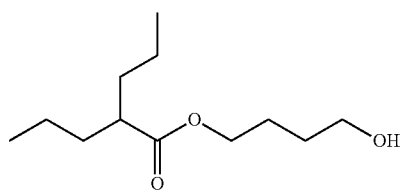

2-propylpentanoic acid (40.16 g, 278.5 mmol) was mixed with butane-1-4-diol (114.65 g, 1272.2 mmol) and methylsulfonic acid (5 drops) in toluene (3500 ml) and the mixture was heated under reflux using a Dean Stark trap for 12 h. After that, toluene was removed under reduced pressure and the crude mixture was dissolved in chloroform (200 ml) and extracted with water (pH 5, 3×200 ml). The combined organic layers were dried over sodium sulfate and the volatiles were removed under reduced pressure giving a clear oil (99%).

The product was analysed by NMR and found to be VA-BDO b) 4-(6-isocyanatohexylcarbamoyloxy)butyl 2-propylpentanoate

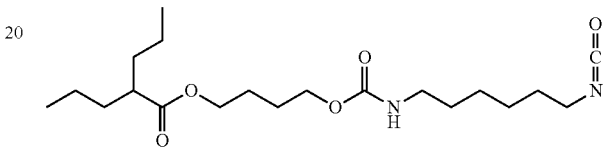

Solution A: 4-hydroxybutyl 2-propylpentanoate (VA-BDO) (10.4518 g 48.3) mmol) was dried under vacuum and placed in a dried flask fitted with a magnetic stir bar and closed with a subaseal. The flask was also fitted with a dry nitrogen gas purge line. Approximately 100 mL of chloroform which had been previously dried over molecular sieve was introduced to the flask.

Solution B. hexamethylene diisocyanate (HDI) (7.900 µg 47.0 mmol) which had been distilled under vacuum was placed in a round bottom flask fitted with a magnetic stir bar and closed with a subaseal. The flask was also fitted with a dry nitrogen gas purge line. Approximately 120 mL of chloroform which had been previously dried over molecular sieve was introduced to the flask. Additionally 5 drops of Tin 2-ethyl hexanoate was added to the flask as a catalyst.

The content of Solution A was slowly added over a 15 minute period to Solution B with stirring.

The mixture was stirred overnight at room temperature under dry nitrogen. The reaction mixture/solvent=Solution C A 10 mL subsample was removed and the chloroform removed by under vacuum by rotovap. The compound was analysed by NMR in CDCl$_3$ and found to contain a high proportion of 4-(6-isocyanatohexylcarbamoyloxy)butyl 2-propylpentanoate (VA-BDO-HDL)

c) Mixture of 1,2-dihydroxy-5,14-dioxo-4,15-dioxa-6,13-diazanonadecan-19-yl 2-propylpentanoate and 1-hydroxy-2-(hydroxymethyl)-4,13-dioxo-3,14-dioxa-5,12-diazaoctadecan-18-yl 2-propylpentanoate

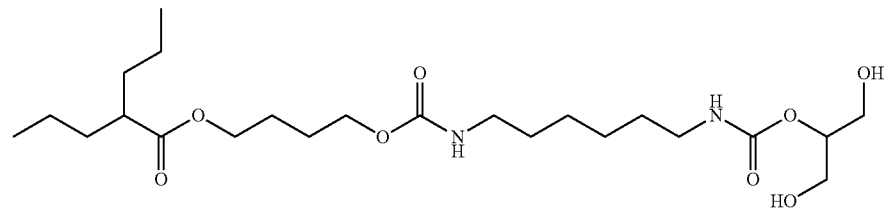

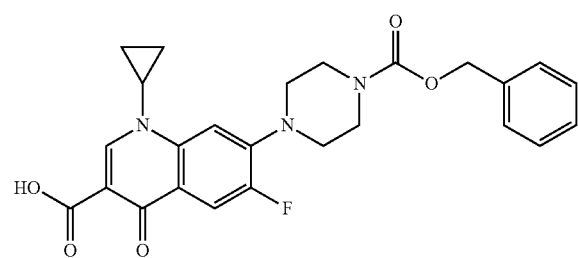 [SMILES: O=C(O)c1cn(C2CC2)c2cc(N3CCN(C(=O)OCc4ccccc4)CC3)c(F)cc2c1=O]

The remaining amount if Solution C from was added slowly over 15 mins to Solution D—which consisted of glycerol (4.4499 g 48.3 mmol) which was dried overnight at 110 C under vacuum) and 100 mL dried chloroform.

The amount of glycerol in solution D was adjusted to give a 1:1 mole ratio of VA-BDO-HDI to Glycerol, with a slight excess of glycerol.

The solution was stirred for 24 hours at 90 C under a nitrogen purge. At various timepoints 4 Ml samples were removed and the chloroform was removed by rotovap and the products were analysed by NMR.

Once high conversion was confirmed by NMR the solution was cooled, more chloroform added to make up to 200 mL and extracted with water (pH 5, 3×200 ml). The combined organic layers were dried over sodium sulfate and the volatiles were removed under reduced pressure giving a white solid A subsample was dissolved in d-DMSO for analysis by NMR. The sample appears to be a mixture of SN1 and SN2 coupling of the VA-BDO-HDI to Glycerol.

The product was dried and stored under nitrogen for use in the production of polymers.

Ciprofloxacin (1-cyclopropyl-6-fluoro-4-oxo-7-[4'-N-[(tert-butyloxy) carbonyl]piperazin]-1-yl-quinoline-3-carboxylic acid)

Example 4

Ciprofloxacin Monoglyceride (2,3-dihydroxypropyl 1-cyclopropyl-6-fluoro-4-oxo-7-(piperazin-1-yl)-1,4-dihydroquinoline-3-carboxylate)

a) 7-(4-(benzyloxycarbonyl)piperazin-1-yl)-1-cyclopropyl-6-fluoro-4-oxo-1,4-dihydroquinoline-3-carboxylic acid

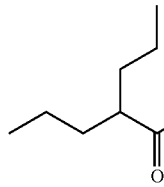

Ciprofloxacin (1-cyclopropyl-6-fluoro-4-oxo-7-piperazin-1-yl)-1,4-quinoline-3-carboxylic acid (0.33 g, 1.0 mmol), was taken up in 2N NaOH solution (10 ml) and cooled to 0° C. (ice/water bath). Benzyloxycarbonyl chloride (0.40 ml, 0.48 g, 2.8 mmol) was added dropwise. The reaction mixture was stirred at 0° C. for 1 h and then gradually warmed to room temperature and stirred for another 16 h. After that the reaction mixture was brought to pH 5 through dropwise addition of 2N HCl solution. The reaction mixture was extracted with $CHCl_3$ (3×50 ml). The combined organic layers were dried over $Na_2SO_4$ and the solvent was removed under reduced pressure. The crude product was purified through crystallisation from acetonitrile to give a colourless solid (0.23 g, 0.49 mmol, 49%)

$^1$H-NMR ($CDCl_3$, 400 MHz): δ[ppm]=8.78 (s, 1H, H-2); 8.10-8.00 (m, 1H, H-5); 7.44-7.28 (m, 6H, 1H of H-8+5H of ArH); 5.17 (s, 2H, Ar$CH_2$); 3.81-3.63 (m, 4H, 2×$CH_2$ of piperazine); 3.56-3.46 (m, 1H of cyclopropane); 3.38-3.23 (m, 4H, 2×$CH_2$ of piperazine); 1.44-1.33 (m, 2H, $CH_2$ of cyclopropane); 1.24-1.13 (m, 2H, $CH_2$ of cyclopropane)

b) (2,2-dimethyl-1,3-dioxolan-4-yl)methyl 7-(4-(benzyloxycarbonyl)piperazin-1-yl)-1-cyclopropyl-6-fluoro-4-oxo-1,4-dihydroquinoline-3-carboxylate

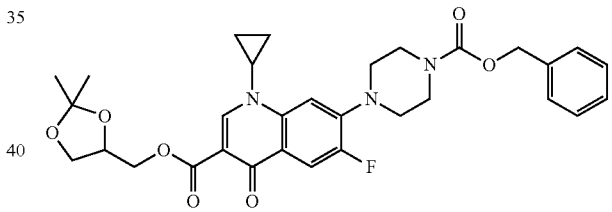

7-(4-(benzyloxycarbonyl)piperazin-1-yl)-1-cyclopropyl-6-fluoro-4-oxo-1,4-dihydroquinoline-3-carboxylic acid (0.47 g, 1.0 mmol) was dissolved in anhydrous $CH_2Cl_2$ (47 ml) under argon. 2,2-dimethyl-1,3-dioxolane-4-methanol (0.20 g, 1.5 mmol) triethylamine (0.40 g, 4.0 mmol) and O-benzotriazol-1-yl-N,N,N',N'-trimethyluronium hexafluorophosphate (0.42 g, 1.1 mmol) were added successively. The reaction mixture was stirred under argon for 72 h. The reaction mixture was washed with saturated $NaHCO_3$ solution (1×50 ml), water (1×50 ml) and dried over $Na_2SO_4$. The organic solvent was removed under reduced pressure, giving a pale, pink solid (0.54 g, 0.93 mmol, 93%).

$^1$H-NMR ($CDCl_3$, 400 MHz): δ[ppm]=8.56 (s, 1H, H-2); 8.10-7.97 (m, 1H, H-5); 7.42-7.13 (m, 6H, 5×ArH+1H of H-8); 5.16 (s, 2H, Ar$CH_2O$); 4.52-4.40 (m, 1H, CH); 4.40-4.30 (m, 2H, 1H of $CH_2O$+1H of $CH_2O$); 4.08-3.96 (m, 1H, 1H of $CH_2O$); 3.86-3.81 (m, 1H, 1H of $CH_2O$); 3.62-3.51 (m, 4H, 2×$CH_2$ of piperazine); 3.37-3.33 (m, 1H, CH of cyclopropane); 3.31-3.14 (m, 4H, 2×$CH_2$ of piperazine); 1.44 (s, 3H, $CH_3$); 1.36 (s, 3H, $CH_3$); 1.34-1.26 (m, $CH_2$ of cyclopropane); 1.26-1.03 (m, $CH_2$ of cyclopropane)

MS (MeCN) 580 [M+1] 602 [M+23]

c) 2,3-dihydroxypropyl 7-(4-(benzyloxycarbonyl)piperazin-1-yl)-1-cyclopropyl-6-fluoro-4-oxo-1,4-dihydroquinoline-3-carboxylate

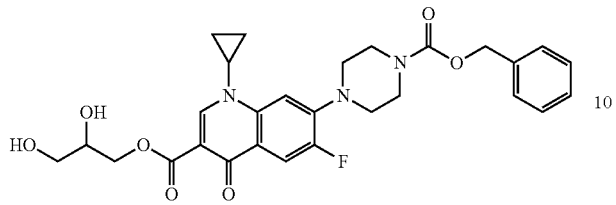

(2,2-dimethyl-1,3-dioxolan-4-yl)methyl 7-(4-(benzyloxycarbonyl)piperazin-1-yl)-1-cyclopropyl-6-fluoro-4-oxo-1,4-dihydroquinoline-3-carboxylate (2.85 g, 4.9 mmol) was dissolved in 95% aqueous ethanol (100 ml). After addition of amberlyst 15 (wet) ion exchange resin and anti bumping granulates the reaction mixture was refluxed for 5 h. The ion exchange resin and the bumping-granulates were removed through filtration and the solvent was removed under reduced pressure to give the crude product as a yellow solid. The crude product was purified through column chromatography ($Al_2O_3$ 1% MeOH in $CHCl_3$) to yield the pure product as a pale yellow solid (1.66 g, 63%).

$^1$H-NMR ($CDCl_3$, 400 MHz): δ[ppm]=8.52 (s, 1H, H-2); 7.97-7.77 (m, 1H, H-5); 7.67-7.51 (m, 1H, H-8); 7.51-7.26 (m, 5H, ArH); 5.17 (s, 2H, $ArCH_2$); 4.52-4.16 (m, 2H, 1H of $CH_2O$+1H of $CH_2O$); 3.97-3.82 (m, 1H, CHO); 3.82-3.43 (m, 6H, 4H of 2×$CH_2$ piperazine+1H of $CH_2O$+1H of CH cyclopropane); 3.19-2.98 (m, 4H, 2×$CH_2$ piperazine); 1.53-1.00 (m, 4H, 2×$CH_2$ cyclopropane)

MS (MeCN) 540 [M+1] 562 [M+23]

d) 2,3-dihydroxypropyl 1-cyclopropyl-6-fluoro-4-oxo-7-(piperazin-1-yl)-1,4-dihydroquinoline-3-carboxylate

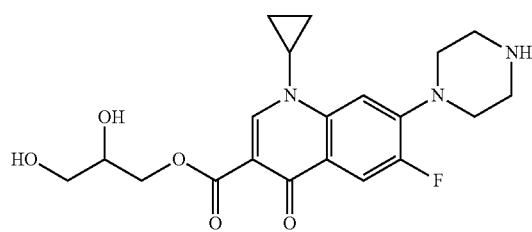 [SMILES: O=C(OCC(O)CO)c1cn(C2CC2)c2cc(N3CCNCC3)c(F)cc2c1=O]

2,3-dihydroxypropyl 7-(4-(benzyloxycarbonyl)piperazin-1-yl)-1-cyclopropyl-6-fluoro-4-oxo-1,4-dihydroquinoline-3-carboxylate (1.66 g, 3.1 mmol) was dissolved in ethanol (100 ml). Hydrogenation in a Thales Nano H-Cube Hydrogenator (10% Pd/C cartridge, 11 bar) and evaporation of the organic solvent gave the crude product as a yellow solid. Crystallisation from acetone gave the crude product as a colourless solid (0.71 g, 57%).

$^1$H-NMR ($d_6$-acetone), 500 MHz): δ[ppm]=8.72 (s, 1H, H-2); 7.91-7.80 (m, 1H, H-5); 7.55-7.43 (m, 1H, H-8); 4.42-4.20 (m, 2H, 1H of $CH_2O$+1H of $CH_2O$); 4.00-3.90 (m, 1H, CH); 3.82-3.75 (m, 1H, 1H of $CH_2O$); 3.70-3.5 (m, 6H, 4H of 2×$CH_2$ piperazine+1H of $CH_2O$+1H CH of cyclopropane); 3.15-3.02 (m, 4H, 2×$CH_2$ of piperazine); 1.48-1.30 (m, 2H, $CH_2$ of cyclopropane); 1.25-1.10 (m, 2H, $CH_2$ of cyclopropane MS (MeCN) 406 [M+1] 428 [M+23]

Example 6

2,3-dihydroxypropyl 1-cyclopropyl-6-fluoro-4-oxo-7-(4-propylpiperazin-1-yl)-1,4-dihydroquinoline-3-carboxylate a) 1-cyclopropyl-6-fluoro-4-oxo-7-(4-propylpiperazin-1-yl)-1,4-dihydroquinoline-3-carboxylic acid

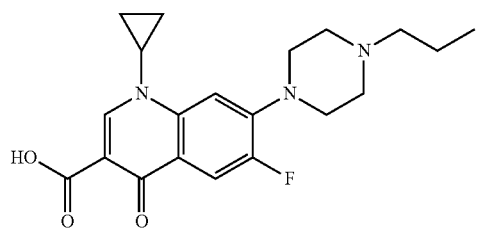 [SMILES: CCCN1CCN(c2cc3c(cc2F)c(=O)c(C(=O)O)cn3C2CC2)CC1]

1-cyclopropyl-6-fluoro-4-oxo-7-(piperazin-1-yl)-1,4-dihydroquinoline-3-carboxylic acid (5.00 g, 15.10 mmol) was taken up in dioxane/water (1:1, 100 ml). 1-iodopropane (3.08 g, 18.10 mmol), and sodiumhydrogencarbonate (3.81 g, 45.30 mmol) was added and heated at 80° C. for 16 h. The crude reaction mixture was cooled to room temperature and acidified with 1M HCl to pH 6. The reaction mixture was extracted with chloroform (3×100 ml), the combined organic layer were dried over sodium sulfate and the volatiles were removed under reduced pressure yielding 3.87 g (69%) of pure product.

$^1$H-NMR ($CDCl_3$, 400 MHz): δ[ppm]=8.77 (s, 1H, H-2); 8.07-7.97 (m, 1H, H-5); 7.41-7.30 (m, 1H, H-8); 3.57-3.46 (m, CH of cyclopropane ring); 3.41-3.24 (m, 4H, 2×$CH_2$ of piperazine); 2.74-2.58 (m, 2×$CH_2$ of piperazine); 2.44-2.33 (m, 2H, $CH_2N$); 1.65-1.45 (m, 2H, $CH_2$); 1.45-1.28 (m, 2H, $CH_2$ of cyclopropane ring); 1.28-1.12 (m, 2H, $CH_2$ of cyclopropane ring); 0.94 (t, 3H, $CH_3$)

MS ($CH_2Cl_2$) 374 [M+1] 747 [2M+1]

b) (2,2-dimethyl-1,3-dioxolan-4-yl)methyl 1-cyclopropyl-6-fluoro-4-oxo-7-(4-propylpiperazin-1-yl)-1,4-dihydroquinoline-3-carboxylate

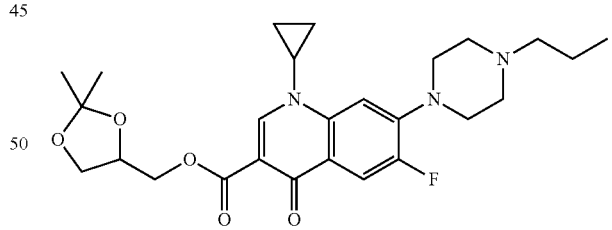

1-cyclopropyl-6-fluoro-4-oxo-7-(4-propylpiperazin-1-yl)-1,4-dihydroquinoline-3-carboxylic acid (8.86 g, 23.70 mmol) was dissolved in anhydrous dichloromethane (370 ml) under argon. 2,2-dimethyl-1,3-dioxolane-4-methanol (4.71 g, 35.60 mmol), triethylamine (9.59 g, 94.80 mmol) and HBTU (9.90 g, 26.10 mmol) were added and the reaction mixture was stirred at room temperature for three days (exclusion of light). The reaction mixture was washed with saturated $NaHCO_3$ solution (500 ml), aqueous (pH 5) hydrochloric acid (500 ml) and water (500 ml) successively. The organic layer was dried over $Na_2SO_4$ and the solvent was removed under reduced pressure, yielding 10.28 g (89%) of a yellow solid.

¹H-NMR (CDCl₃, 400 MHz): δ[ppm]=8.53 (s, 1H, H-2); 8.09-7.95 (m, 1H, H-5); 7.32-7.17 (m, H-8); 4.51-4.41 (m, 1H, CH); 4.41-4.31 (m, 2H, 1H of CH₂O+1H of CH₂O); 4.19-4.09 (m, 1H, CH₂O); 3.98-3.86 (m, 1H, CH₂O); 3.50-3.36 (m, 1H of cyclopropane ring); 3.36-3.15 (m, 4H, 2×CH₂ of piperazine); 2.76-2.61 (m, 4H, 2×CH₂ of piperazine); 2.49-2.31 (m, 2H, CH₂N); 1.72-1.48 (m, 2H, CH₂CH₂CH₃); 1.44 (s, 3H, CH₃), 1.36 (s, 3H, CH₃); 1.33-1.25 (m, 2H, CH₂ of cyclopropane); 1.16-1.03 (m, 2H, CH₂ of cyclopropane); 0.93 (t, 3H, CH₃)

c) 2,3-dihydroxypropyl 1-cyclopropyl-6-fluoro-4-oxo-7-(4-propylpiperazin-1-yl)-1,4-dihydroquinoline-3-carboxylate

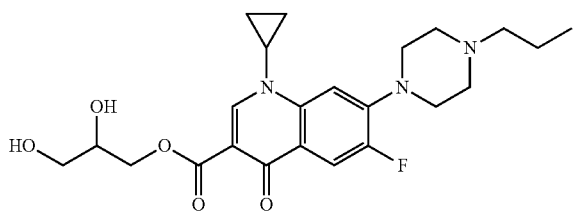 [SMILES: CCCN1CCN(c2cc3c(cc2F)c(=O)c(C(=O)OCC(O)CO)cn3C2CC2)CC1]

(2,2-dimethyl-1,3-dioxolan-4-yl)methyl 1-cyclopropyl-6-fluoro-4-oxo-7-(4-propylpiperazin-1-yl)-1,4-dihydroquinoline-3-carboxylate (2.45 g, 5.03 mmol) was dissolved in anhydrous dichloromethane (245 ml) under argon. A 1 M solution of boron trichloride in dichloromethane (6.3 ml, 6.30 mmol) was added dropwise and the reaction mixture was stirred at room temperature for 1 h. Methanol (25 ml) was added to the reaction mixture and the volatiles were removed under reduced pressure. The crude product was purified through flash column chromatography (5% MeOH in CHCl₃) giving a yellow oil (1.58 g, 3.53 mmol, 70%).

MS (MeOH): 448.3 [M+1]

Levofloxacin (S)-(9-fluoro-3-methyl-10-(4-methylpiperazin-1-yl)-7-oxo-3,7-dihydro-2H-[1,4]oxazino[2,3,4-ij]quinoline-6-carboxylic acid Example 7

(3S) 2,3-dihydroxypropyl 9-fluoro-3-methyl-10-(–4-methylpiperazin-1-yl)-7-oxo-3,7-dihydro-2H-[1,4]oxazino[2,3,4-ij]quinoline-6-carboxylate a) (3S)-(2,2-dimethyl-1,3-dioxolan-4-yl)methyl 9-fluoro-3-methyl-10-(4-methylpipirazin-1-yl)-7-oxo-3,7-dihydro-2H-[1,4]oxazino[2,3,4-ij]quinoline-6-carboxylate

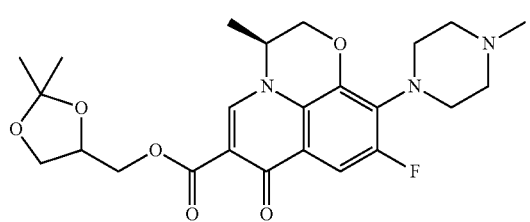 [SMILES: C[C@H]1COc2c(N3CCN(C)CC3)c(F)cc3c(=O)c(C(=O)OCC4COC(C)(C)O4)cn1c23]

(3S)-(9-fluoro-3-methyl-10-(4-methylpiperazin-1-yl)-7-oxo-3,7-dihydro-2H-[1,4]oxazino[2,3,4-ij]quinoline-6-carboxylic acid (10.00 g, 27.7 mmol), was dissolved in CH₂Cl₂ (500 ml) under argon. 2,2-dimethyl-1,3-dioxolane-4-methanol (5.49 g, 41.5 mmol) triethylamine (11.21 g, 110.8 mmol) and O-benzotriazol-1-yl-N,N,N',N'-trimethyluronium hexafluorophosphate (11.56 g, 30.5 mmol) were added successively. The reaction mixture was stirred under argon for 72 h. The reaction mixture was washed with saturated NaHCO₃ solution (1×500 ml), water (1×50 ml) and dried over Na₂SO₄. The organic solvent was removed under reduced pressure giving a white solid. The crude product was crystallized from acetonitrile giving the product in 44% yield (5.81 g).

¹H-NMR (CDCl₃, 400 MHz): δ[ppm]=8.29 (s, 1H, H-5); 7.65 (m, 1H, H-8); 4.53-4.41 (m, 1H, CH); 4.41-4.25 (m, 5H, 1H of CH₂O, 1H of CH₂O, 2H of CH₂O, 1H of CHN); 4.21-4.09 (m, 1H, 1H of CH₂O); 3.96-3.85 (m, 1H of CH₂O); 3.43-3.23 (m, 4H, 2×CH₂ piperazine); 2.65-2.45 (m, 4H 2×CH₂ piperazine); 2.36 (s, 3H, NCH₃); 1.58 (d, 3H, CH₃); 1.44 (s, 3H, CH₃), 1.37 (s, 3H, CH₃).

MS (EtOH) 475 [M+1].

b) (S)-4-(6-((2,3-dihydroxypropoxy)carbonyl)-9-fluoro-3-methyl-7-oxo-3,7-dihydro-2H-[1,4]oxazino[2,3,4-ij]quinolin-10-yl)-1-methylpiperazin-1-ium 2,2,2-trifluoroacetate

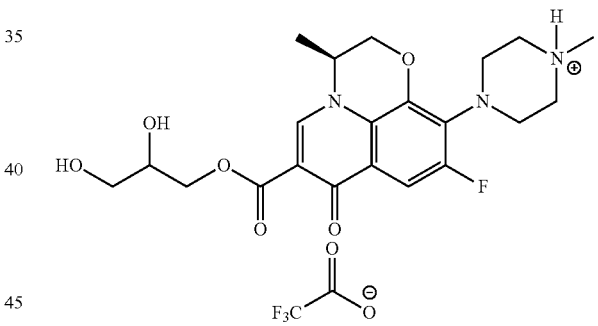

(S)-(2,2-dimethyl-1,3-dioxolan-4-yl)methyl 9-fluoro-3-methyl-10-(4-methylpipirazin-1-yl)-7-oxo-3,7-dihydro-2H-[1,4]oxazino[2,3,4-ij]quinoline-6-carboxylate (1.00 g, 2.1 mmol), was dissolved in CH₂Cl₂ (42 ml) under argon and cooled to 0° C. Trifluoroacetic acid (2.00 ml, 2.96 g, 26.0 mmol) was added and the reaction mixture was allowed to stir at 0° C. for 4 h and then over night at room temperature. The reaction mixture was flushed through a plug of Al₂O₃ (10% MeOH in CHCl₃) (2×). After that the organic solvents were collected and removed under reduced pressure giving the product as a yellow gum (0.24 g, 104%).

¹H-NMR (CDCl₃, 400 MHz): δ[ppm]=8.76 (s, H-5); 7.63-7.50 (m, H-8); 4.74-4.61 (m, 1H, H-3 of benzoxazine ring); 4.61-4.50 (m, 1H, NHCHCH₂O); 4.50-4.33 (m, 2H, 1H of NHCHCH₂O+1H of CH₂OCO); 4.33-4.24 (m, 1H, CH₂OCO); 4.03-3.93 (m, 1H, CHOH); 3.73-3.53 (m, 6H, 2×CH₂ piperazine+CH₂OH); 3.43-3.22 (m, 4H, 2×CH₂ piperazine); 3.01 (s, 3H, +NHCH₃); 1.55 (d, 3H, CH₃).

MS (MeOH) 436 [M+1]; 458 [M+23]

c) (S)-2,3-dihydroxypropyl 9-fluoro-3-methyl-10-(-4-methylpiperazin-1-yl)-7-oxo-3,7-dihydro-2H-[1,4]oxazino[2,3,4-ij]quinoline-6-carboxylate

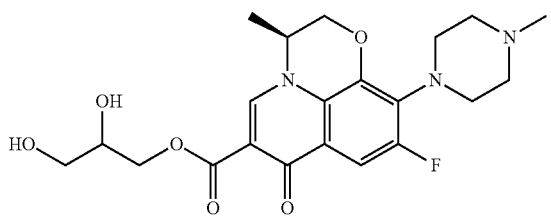 [SMILES: C[C@H]1COc2c(N3CCN(C)CC3)c(F)cc3c(=O)c(C(=O)OCC(O)CO)cn1c23]

(S)-4-(6-((2,3-dihydroxypropoxy)carbonyl)-9-fluoro-3-methyl-7-oxo-3,7-dihydro-2H-[1,4]oxazino[2,3,4-ij]quinolin-10-yl)-1-methylpiperazin-1-ium 2,2,2-trifluoroacetate (0.50 g, 0.91 mmol) was dissolved in methanol under argon and cooled to 0° C. (ice/salt bath). 1 equiv. of NaOH dissolved in methanol (25 ml) was added slowly until the solution reached pH 7-pH 8. The reaction mixture was passed through a plug of $Al_2O_3$ (10% MeOH in $CHCl_3$). The organic solvent was removed under reduced pressure giving a yellow solid (0.35 g, 88%)

Or in an alternate procedure:

(S)-(2,2-dimethyl-1,3-dioxolan-4-yl)methyl 9-fluoro-3-methyl-10-(4-methylpipirazin-1-yl)-7-oxo-3,7-dihydro-2H-[1,4]oxazino[2,3,4-ij]quinoline-6-carboxylate (5.67 g, 10.8 mmol) was dissolved in 80% aqueous acetic acid (45 mL). The reaction mixture was heated at 75° C. for 8 hrs. The solvent was removed under reduced pressure. Toluene was added to the residue and the solvent again removed under reduced pressure. The product was purified by column chromatography (10%, followed by 20%, 30%, and 75% methanol/chloroform as eluent) to give the title compound as an off-white solid in 84% yield.

$^1$H-NMR ($CDCl_3$, 400 MHz): δ[ppm]=8.67 (s, H-5); 7.56-7.40 (m, 1H, H-8); 4.71-4.56 (m, 1H, H-3 of benzoxazine ring); 4.56-4.33 (m, 3H, 2H of NHCH$CH_2$O+1H of $CH_2$OCO); 4.33-4.21 (m, 1H, CH$_7$OCO); 4.02-3.91 (m, 1H, CHOH); 3.57-3.52 (m, 2H, $CH_2$OH); 3.52-3.34 (m, 4H, 2×$CH_2$ piperazine); 2.85-2.56 (m, 4H, 2×$CH_2$ piperazine); 2.43 (s, 3H, NH$CH_3$); 1.52 (d, 3H, $CH_3$).

MS (MeOH) 436 [M+1] 458 [M+23]

Example 8

(S)-1,3-dihydroxypropan-2-yl 9-fluoro-3-methyl-10-(4-methylpiperazin-1-yl)-7-oxo-3,7-dihydro-2H-[1,4]oxazino[2,3,4-ij]quinoline-6-carboxylate a) (S)-2-phenyl-1,3-dioxan-5-yl 9-fluoro-3-methyl-10-(4-methylpiperazin-1-yl)-7-oxo-3,7-dihydro-2H-[1,4]oxazino[2,3,4-ij]quinoline-6-carboxylate

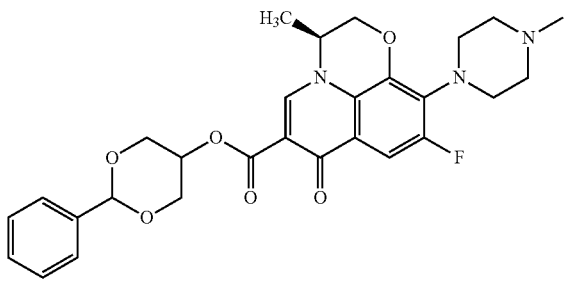 [SMILES: C[C@H]1COc2c(N3CCN(C)CC3)c(F)cc3c(=O)c(C(=O)OC4COC(c5ccccc5)OC4)cn1c23]

(S)-9-fluoro-3-methyl-10-(4-methylpiperazin-1-yl)-7-oxo-3,7-dihydro-2H-[1,4]oxazino[2,3,4-ij] quinoline-6-carboxylic acid (4.18 g, 11.56 mmol) was dissolved in anhydrous dichloromethane (210 ml) under argon. 1,3-O-benzylideneglycerol (2.50 g, 13.67 mmol), triethylamine (4.68 g, 46.24 mmol) and HBTU (4.38 g, 11.56 mmol) were added successively. The reaction mixture was stirred at room temperature (exclusion of light) for 3 days. The reaction mixture was washed with saturated $NaHCO_3$ solution (500 ml), aqueous (pH 5) hydrochloric acid (500 ml) and water (500 ml) successively. The organic layer was dried over $Na_2SO_4$ and the solvent was removed under reduced pressure. The crude product was purified through flash column chromatography ($SiO_2$/10% MeOH in $CHCl_3$) yielding 4.32 g, 71%) of a yellow, crystalline solid.

$^1$H-NMR ($CDCl_3$, 400 MHz): δ[ppm]=8.22 (s, 1H, H-5); 7.64-7.52 (m, 1H, H-8); 7.46-7.31 (m, 4H, ArH); 7.10 (d, 1H, ArH); 5.65 (s, 1H, CHOCO); 4.91 (s, 1H, ArCH); 4.64-4.01 (m, 7H, 1H of CHN+2H of $CH_2$O+4H of 2×$CH_2$O); 3.38-3.22 (m, 2×$CH_2$ of piperazine ring); 2.62-2.43 (m, 4H, 2×$CH_2$ of piperazine ring); 2.36 (s, $NCH_3$); 0.95 (d, 3H, $CHCH_3$).

MS (MeOH) 524 [M+1] 546 [M+23]

b) (S)-1,3-dihydroxypropan-2-yl 9-fluoro-3-methyl-10-(4-methylpiperazin-1-yl)-7-oxo-3,7-dihydro-2H-[1,4]oxazino[2,3,4-ij]quinoline-6-carboxylate

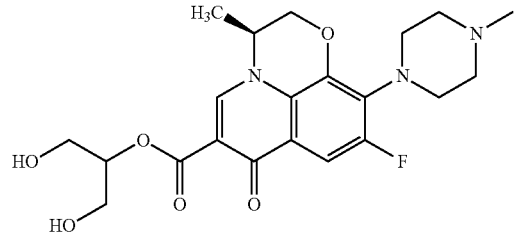 [SMILES: C[C@H]1COc2c(N3CCN(C)CC3)c(F)cc3c(=O)c(C(=O)OC(CO)CO)cn1c23]

(S)-2-phenyl-1,3-dioxan-5-yl 9-fluoro-3-methyl-10-(4-methylpiperazin-1-yl)-7-oxo-3,7-dihydro-2H-[1,4]oxazino[2,3,4-ij]quinoline-6-carboxylate (0.50 g, 9.55 mmol), was dissolved in a mixture of dichloromethane/methanol (2:1.5, 87.5 ml) under argon. Palladium catalyst (10 wt % Pd/C) (180 mg) was added, the flask was evacuated and allowed to stir 1 atm of hydrogen gas at room temperature for 16 hours. The crude reaction mixture was passed through a glass microfiber on a sintered funnel. The volatiles were removed under reduced pressure yielding 370 mg (88%) of a yellow gum.

$^1$H-NMR ($CDCl_3$, 400 MHz): δ[ppm]=8.72 (s, 1H), 7.57 (dd, 1H, $J^1$=12.6 Hz, $J^2$=1.8 Hz), 4.67-4.60 (m, 1H), 4.55-4.49 (m, 1H), 4.41-4.35 (m, 2H), 4.31-4.25 (m, 1H), 4.00-3.92 (m, 1H), 3.69-3.63 (m, 2H), 3.46-3.33 (m, 4H), 2.71-2.60 (m, 4H), 2.40 (s, 3H), 1.53 (d, 3H, J=6.8 Hz).

Benzocaine (ethyl 4-aminobenzoate)

Example 9

Ethyl 4-((1,3-dihydroxypropan-2-yloxy)carbonylamino)benzoate a) 2-phenyl-1,3-dioxan-5-yl carbonochloridate

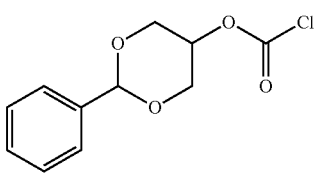 [SMILES: O=C(Cl)OC1COC(c2ccccc2)OC1]

Triphosgene (bis(trichloromethyl)carbonate (13.35 g, 45.0 mmol) was added under argon at room temperature to a solution of 1,3-O-benzylideneglycerol (18.02 g, 100.0 mmol) in dry CH$_2$Cl$_2$ (300 ml). The reaction mixture was cooled to −40° C. and a solution of pyridine (10.9 ml, 135.0 mmol) was added over 35 min under stirring. Upon completion of the addition the reaction mixture was stirred for 30 min at −40° C. Then it was allowed to warm to 0° C. over 60 min and subsequently warmed to rt over 3.5 h under stirring. The reaction product was used in the next step without any further purification $^1$H-NMR (CDCl$_3$, 400 MHz): δ[ppm]=7.42-7.33 (m, 2H), 7.31-7.21 (m, 3H), 5.50 (s, 1H), 4.72-4.70 (m, 1H), 4.34-4.28 (m, 2H), 4.18-4.09 (m, 2H)

b) Ethyl 4-((2-phenyl-1,3-dioxan-5-yloxy)carbonylamino)benzoate

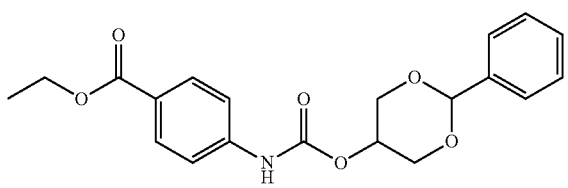 [SMILES: CCOC(=O)c1ccc(NC(=O)OC2COC(c3ccccc3)OC2)cc1]

Ethyl 4-aminobenzoate (benzocaine) (16.53 g, 0.10 mol) was dissolved in dry CH$_2$Cl$_2$ (160 ml) under argon. The reaction mixture was cooled to 0° C. and triethylamine (16.7 ml, 0.12 mol) was added. 2-phenyl-1,3-dioxan-5-yl carbonochloridate (224.27 g, 0.10 mol) (as a solution in 300 ml CH$_2$Cl$_2$—obtained in the previous reaction step) was added gradually over 40 min. The reaction mixture was stirred for 1 h at 0° C. and then gradually warmed to room temperature and allowed to stir over night. The crude reaction mixture was washed with 1M aqueous HCl (2×300 ml), saturated NaHCO$_3$ solution (2×300 ml) and water (2×300 ml) successively. The organic layer was dried over Na$_2$SO$_4$ and the solvent was removed under reduced pressure. The crude product was purified through flash column chromatography (SiO$_2$/CHCl$_3$) yielding (25.9 g, 70.0 mmol, 71%) of a colourless crystalline solid.

$^1$H-NMR (CDCl$_3$, 400 MHz): δ[ppm]=8.00 (d, 2H, J=8.8 Hz), 7.55-7.50 (m, 2H), 7.44 (d, 2H, J=8.8 Hz), 7.41-7.36 (m, 3H), 7.11 (s, 1H), 5.62 (s, 1H), 4.41-4.33 (m, 4H), 4.25-4.22 (m, 2H), 1.38 (tr, 3H, J=7.1 Hz)

c) Ethyl 4-((1,3-dihydroxypropan-2-yloxy)carbonylamino)benzoate

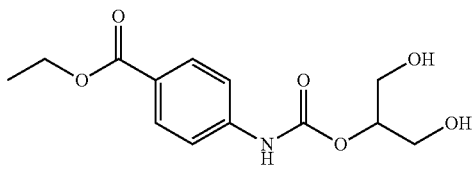 [SMILES: CCOC(=O)c1ccc(NC(=O)OC(CO)CO)cc1]

Ethyl 4-((2-phenyl-1,3-dioxan-5-yloxy)carbonylamino) benzoate (4.70 g, 12.7 mmol) was dissolved in ethanol (500 ml) under argon and Pd/C (2.48 g, 2.3 mmol) was added. The flask was flushed with hydrogen and allowed to stir under 1 atm H$_2$ at room temperature for 16 h. The crude reaction mixture was passed through a plug of celite and the solvent was removed under reduced pressure yielding (3.14 g, 11.2 mmol, 88%). The product was used without any further purification.

$^1$H-NMR (CDCl$_3$, 400 MHz): δ[ppm]=8.00 (d, 2H, J=8.8 Hz), 7.46 (d, 2H, J=8.8 Hz), 7.17 (s, 1H), 4.97-4.93 (m, 1H), 4.35 (quart, J=7.1 Hz), 3.99-3.86 (m, 4H), 2.62-2.11 (br, 2H), 1.38 (tr, 3H, J=7.1 Hz)

Menthol
(1R,2S,5R)-2-isopropyl-5-methylcyclohexanol)

Example 10

(1R,2S,5R)-2-isopropyl-5-methylcyclohexyl 2,3-dihydroxypropanoate a) Sodium (R)-(+)-2,2-dimethyl-1,3-dioxolane-4-carboxylate

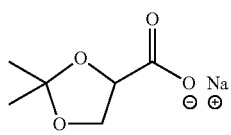

Methyl (R)-(+)-2,2-dimethyl-1,3-dioxolane-4-carboxylate (1.00 g, 6.2 mmol) was dissolved in 80% aqueous 1,4-dioxane. 1.2 M aqueous NaOH solution was added (5.2 ml) and the reaction mixture was stirred at room temperature for 3 h. After that the solvents were removed under reduced pressure and a colourless solid was obtained (1.03 g, 6.1 mmol, 98%). The product was used immediately in the next reaction step without further purification.

b) (R)-(+)-2,2-dimethyl-1,3-dioxolane-4-carboxylic acid

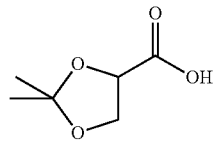

Sodium (R)-(+)-2,2-dimethyl-1,3-dioxolane-4-carboxylate (1.03 g, 6.1 mmol) was dissolved in a mixture of water (1.2 ml) and ethyl acetate (1.2 ml) and cooled to 0° C. 2 M aqueous $H_3PO_4$ solution (7 ml) was added until the reaction mixture reached pH 2. After that the reaction mixture was saturated with NaCl and the reaction mixture was extracted with ethyl acetate (3×20 ml). The organic layer was dried over $Na_2SO_4$ and the solvent was removed under reduced pressure. The product (0.73 g, 4.9 mmol, 81%) was used in the next step without any further purification.

$^1$H-NMR (CDCl$_3$, 400 MHz): δ[ppm]=8.99-8.13 (br, 1H), 4.64-4.61 (m, 1H), 4.32-4.25 (m, 1H), 4.22-4.17 (m, 1H), 1.52 (s, 3H), 1.41 (s, 3H)

c) (1R,2S,5R)-2-isopropyl-5-methylcyclohexyl 2,2-dimethyl-1,3-dioxolane-4-carboxylate

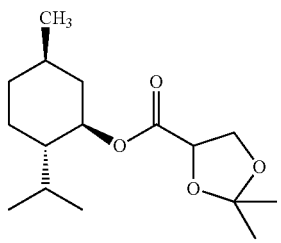 [SMILES: CC(C)[C@@H]1CC[C@@H](C)C[C@H]1OC(=O)C1COC(C)(C)O1]

(R)-(+)-2,2-dimethyl-1,3-dioxolane-4-carboxylic acid (2.86 g, 19.6 mmol) was dissolved in anhydrous CH$_2$Cl$_2$ (120 ml) under argon. Menthol (1R,2S,5R)-2-isopropyl-5-methylcyclohexanol) (3.67 g, 23.5 mmol), triethylamine (7.93 g, 78.4 mmol) and O-benzotriazol-1-yl-N,N,N',N'-trimethyluronium hexafluorophosphate (8.18 g, 21.6 mmol) were added successively. The reaction mixture was stirred under argon for 72 h. The reaction mixture was washed with saturated NaHCO$_3$ solution (3×50 ml), aqueous HCl (pH 5) (3×50 ml) and water (3×50 ml) and dried over Na$_2$SO$_4$. The organic solvent was removed under reduced pressure, giving a yellow oil. (0.54 g, 0.93 mmol, 93%). The crude product was purified through flash column chromatography (SiO$_2$/15%-25% graduent of ethyl acetate in hexane) yielding 3.16 (11.2 mmol, 57%) of a yellow oil.

$^1$H-NMR (CDCl$_3$, 400 MHz): δ[ppm]=4.82-4.69 (m, 1H), 4.59-4.50 (m, 1H), 4.25-4.18 (m, 1H), 4.10-4.01 (m, 1H), 2.03-1.94 (m, 1H), 1.89-1.77 (m, 1H), 1.70-1.62 (m, 2H), 1.55-1.35 (m, 8H), 1.09-0.95 (m, 2H), 0.92-0.79 (m, 7H), 0.74 (d, J=7.0 Hz)

d) (1R,2S,5R)-2-isopropyl-5-methylcyclohexyl 2,3-dihydroxypropanoate

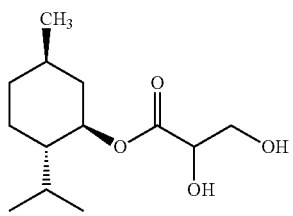 [SMILES: CC(C)[C@@H]1CC[C@@H](C)C[C@H]1OC(=O)C(O)CO]

(1R,2S,5R)-2-isopropyl-5-methylcyclohexyl 2,2-dimethyl-1,3-dioxolane-4-carboxylate (1.00 g, 35.2 mmol) was dissolved in 98% aqueous ethanol (10 ml). Amberlyst 15 (wet) ion exchange resin (0.30 g) and bumping granulate were added. The reaction mixture was refluxed for 4 h without stirring (under argon). After that, the reaction was brought to room temperature, the resin and bumping granulate were removed and the solvent was removed under reduced pressure. The product was obtained in quantitative yield (0.94 g)

$^1$H-NMR (CDCl$_3$, 400 MHz): δ[ppm]=4.86-4.74 (m, 1H), 4.26-4.19 (m, 1H), 3.92-3.87 (m, 1H), 3.85-3.79 (m, 1H), 3.25-3.14 (m, 1H), 2.22-2.08 (m, 1H), 2.06-1.96 (m, 1H), 1.93-1.79 (m, 1H), 1.74-1.65 (m, 2H), 1.56-

Example 11

1,3-dihydroxypropan-2-yl (2S,5R)-2-isopropyl-5-methylcyclohexyl phosphonate a) Dichloro((1R,2S,5R)-2-isopropyl-5-methylcyclohexyloxy)phosphine

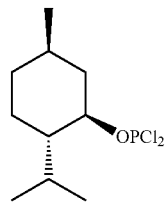

The phosphorus trichloride (56.0 ml, 87.89 g, 0.640 mol) was added to dichloromethane (anhydrous) under argon gas to obtain a solution. The solution was cooled to −30° C. and (−)-menthol (1R,2S,5R) (10.00 g, 0.0640 mol) was added portion wise over 10 mins. The solution was allowed to warm to ambient temperature and was allowed to stir at ambient temperature for 16 hours. The solvent was removed in vacuo to obtain a colourless oil (16.46 g). The crude product was used directly in the subsequent step.

b) (2S,5R)-2-isopropyl-5-methylcyclohexyl 2-phenyl-1,3-dioxan-5-yl phosphonate

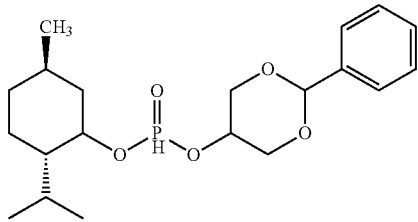

The dichloro(2S,5R)-2-isopropyl-5-methylcyclohexyloxyphosphine (8.23 g, 0.0320 mol) was dissolved in dichloromethane (anhydrous) (100 ml) under argon gas. Cooled to 0° C. Added a solution of cis-1,3-benzylideneglycerol (7.21 g, 0.0400 mol) and tert-butanol (2.97 g, 0.040 mol) (1:1) in dichloromethane (anhydrous) dropwise over 30 mins. Then added triethylamine (8.9 ml, 6.47 g, 0.0640 mol) dropwise. Allowed to stir at 0° C. for 10 mins. And then allowed to gradually warm to ambient temperature. And removed solvent in vacuo to obtain a colourless crystalline solid (26.67 g).

The crude product was chromatographed on silica gel using EtOc/pet spirit 60-80 to obtain the product fraction as a colourless oil (1.29 g)

$^1$H-NMR (CDCl$_3$, 400 MHz): δ[ppm]=7.93-7.92 (m, 0.5H, P—H), 7.58-7.29 (m, 5H), 6.17-6.16 (m, 0.5H, P—H), 5.56 (s, 1H), 4.53-3.98 (m, 6H), 2.31-1.89 (m, 3H), 1.88-0.57 (m, 15H)

c) 1,3-dihydroxypropan-2-yl (2S,5R)-2-isopropyl-5-methylcyclohexyl phosphonate

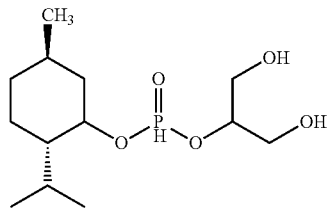

The dichloro(2S,5R)-2-isopropyl-5-methylcyclohexyl-2-phenyl-1,3-dioxan-5-yl phosphonate (0.97 g; 2.54 mmol) was dissolved in 80% (v/v) aqueous acetic acid (10 ml) and allowed to stir at 70° C. for 3 hrs. The solvent was removed in vacuo followed by pumping under high vacuum to obtain an oil (0.69 g, 2.37 mmol).

$^1$H-NMR (CDCl$_3$, 400 MHz): δ[ppm]=7.89-7.87 (m, 0.5H, P—H), 6.01-5.89 (m, 0.5H, P—H), 4.42-3.28 (m, 8H), 2.29-0.51 (m, 18H)

Phenol

Example 12

1,3-dihydroxypropan-2-yl phenyl succinate a) 4-oxo-4-phenoxybutanoic acid

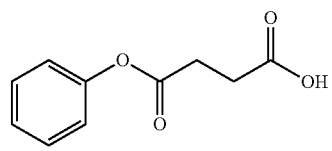 [SMILES: O=C(O)CCC(=O)Oc1ccccc1]

Phenol (1.88 g, 20.0 mmol) was dissolved in a solution of sodium carbonate (anhydrous) (1.06 g, 10.0 mmol) in water (20 ml) and cooled to 0° C. Succinic anhydride (2.00 g, 20.0 mmol) was added and the suspension was allowed to stir at 0° C. for 1 h. The reaction mixture was gradually warmed to room temperature and stirred over night. The clear solution was cooled to 0° C. and acidified to pH 0 (addition of 1M aqueous HCl). The reaction mixture was extracted with chloroform (3×25 ml), dried over Na$_2$SO$_4$, filtered and the solvent removed under reduced pressure to obtain a white solid (1.63 g, 8.4 mmol, 42%). The product was used without any further purification.

$^1$H-NMR (CDCl$_3$, 200 MHz): δ[ppm]=7.44-7.03 (m, 5H), 2.95-2.77 (m, 4H)

b) Phenyl 2-phenyl-1,3-dioxan-5-yl succinate

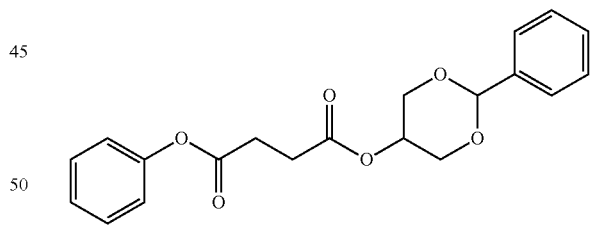

4-oxo-4-phenoxybutanoic acid (1.00 g, 5.15 mmol) was dissolved in anhydrous CH$_2$Cl$_2$ (55 ml) under argon. Menthol 1,3-O-benzylideneglycerol (1.11 g, 6.18 mmol), triethylamine (2.09 g, 20.6 mmol) and O-benzotriazol-1-yl-N,N,N',N'-tetramethyluronium hexafluorophosphate (2.15 g, 5.67 mmol) were added successively. The reaction mixture was stirred under argon for 72 h. The reaction mixture was washed with saturated NaHCO$_3$ solution (3×50 ml), aqueous HCl (pH 5) (3×50 ml) and water (3×50 ml) and dried over Na$_2$SO$_4$. The organic solvent was removed under reduced pressure, giving a yellow oil. (0.54 g, 0.93 mmol, 93%). The crude product was purified through flash column chromatography (SiO$_2$/10% MeOH in chloroform) yielding 0.98 g (2.58 mmol, 50%) of a yellow solid.

$^1$H-NMR (CDCl$_3$, 400 MHz): δ[ppm]=7.54-7.48 (m, 2H), 7.41-7.31 (m, 5H), 7.23-7.19 (m, 1H), 7.13-7.06 (m, 2H), 5.57 (s, 1H), 4.78 (m, 1H), 4.33-4.29 (m, 2H), 4.20-4.16 (m, 2H), 2.97-2.86 (m, 4H)

c) 1,3-dihydroxypropan-2-yl phenyl succinate

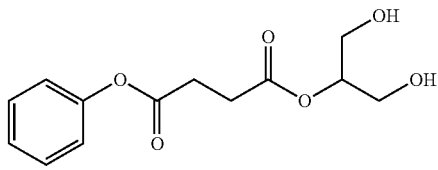 [SMILES: O=C(CCC(=O)OC(CO)CO)Oc1ccccc1]

Phenyl 2-phenyl-1,3-dioxan-5-yl succinate (0.11 g, 0.3 mmol) was dissolved in ethanol (20 ml) under argon and Pd/C (0.09 g, 0.1 mmol) was added. The flask was flushed with hydrogen and allowed to stir under 1 atm H$_2$ at room temperature for 16 h. The crude reaction mixture was passed through a plug of celite and the solvent was removed under reduced pressure yielding (0.9 g, 0.26 mmol, 89%). The product was used without any further purification.

$^1$H-NMR (CDCl$_3$, 400 MHz): δ[ppm]=7.43-7.33 (m, 2H), 7.25-7.21 (m, 1H), 7.12-7.05 (m, 2H), 4.97 (quint, 1H, J=4.4 Hz), 3.88-3.80 (m, 4H), 2.95-2.91 (m, 2H), 2.82-2.75 (m, 2H), 2.58-1.60 (br, 2H)

(6) Synthesis of the Protected Monoglyceride—Linker-Building Blocks (a) Synthesis of Protected Monoglycerides with a Diacid Linker

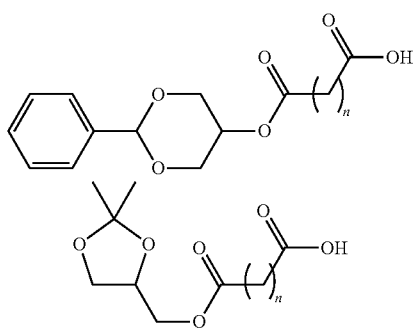

1,3-Benzylideneglycerol and solketal ((2,2-dimethyl-1,3-dioxolan-4-yl)methanol) are each separately dissolved in organic solvent and each reacted with a diacid (succinic, glutaric, adipic, pimelic, suberic, azelaic, sebacic) under appropriate conditions.

(b) Synthesis of Protected Monoglycerides with an Omega Hydroxy Acid Linker

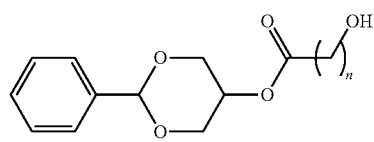

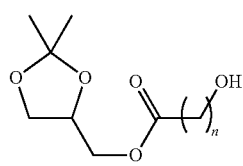

1,3-Benzylideneglycerol and solketal are each separately dissolved in organic solvent and each reacted with an omega hydroxy acid under appropriate conditions.

(c) Synthesis of Protected Monoglycerides with a Chloroformate Linker

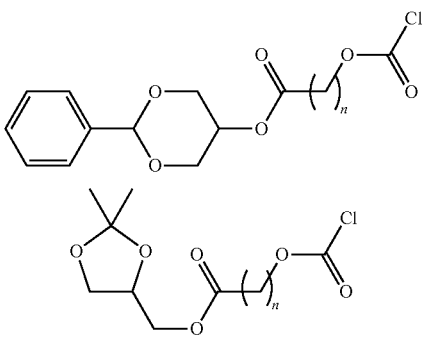

1,3-Benzylideneglycerol and solketal are each separately dissolved in organic solvent and each reacted with an omega hydroxy acid under appropriate conditions. The product of this conversion is reacted with triphosgene to give the protected monoglycerides with a chloroformate linker.

(d) Synthesis of Chloroformate Functionalised Protected Monoglycerides

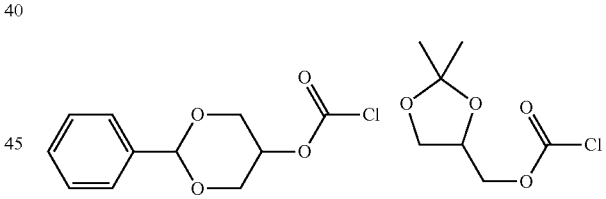

1,3-Benzylideneglycerol and solketal are each separately dissolved in organic solvent and each reacted with triphosgene under appropriate conditions.

(7) Synthesis of the Monoglyceride-Linker-Bioactive Agent-Conjugates (a) Coupling of Hydroxy Containing Bioactive Agents with Protected Monoglycerides with a Diacid Linker

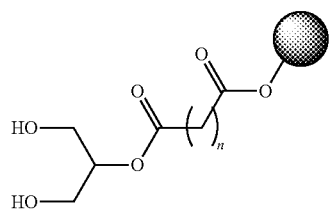

-continued

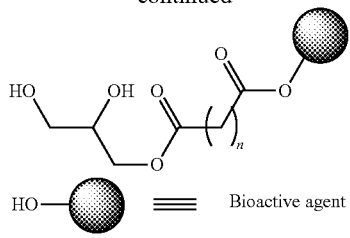

≡ Bioactive agent

A hydroxy containing bioactive agent—such as Codeine, Fluconazole, Latanoprost or Dexamethasone—(after conversion into a prodrug by protecting additional functional groups with appropriate bioerodable protection groups) is reacted with protected monoglycerides with a diacid linker. The monoglyceride protection groups are removed under appropriate conditions giving the monoglyceride functionalised (at the primary or secondary alcohol positions of the glyceride) bioactive agent monomers.

(b) Coupling of Hydroxy Containing Bioactive Agents with Protected Monoglycerides with An Omega Hydroxy Acid Linker

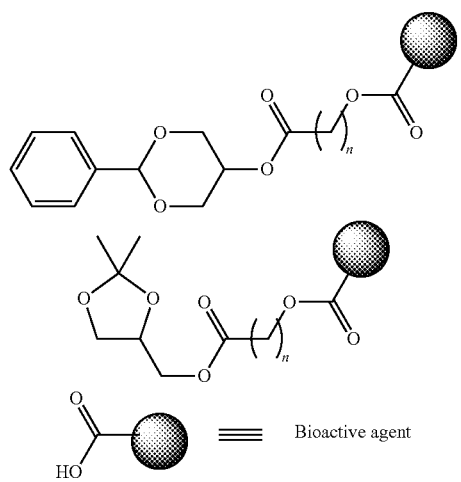

≡ Bioactive agent

A carboxy acid containing bioactive agent—such as Ciprofloxacin, Levofloxacin or Valproic acid—(after conversion into a prodrug by protecting additional functional groups with appropriate bioerodable protection groups) is reacted with protected monoglycerides with a omega hydroxy acid linker. The monoglyceride protection groups are removed under appropriate conditions giving the monoglyceride functionalised (at the primary or secondary alcohol positions of the glyceride) bioactive agent monomers.

(c) Coupling of Amine Containing Bioactive Agents with Protected Monoglycerides with a Chloroformate Linker

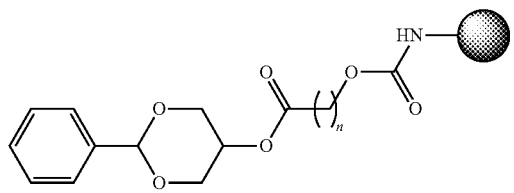

-continued

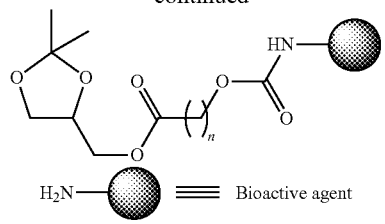

≡ Bioactive agent

An amine containing bioactive agent—such as Benzocaine—(after conversion into a prodrug by protecting additional functional groups with appropriate bioerodable protection groups) is reacted with protected monoglycerides with a chloroformate linker. The monoglyceride protection groups are removed under appropriate conditions giving the monoglyceride functionalised (at the primary or secondary alcohol positions of the glyceride) bioactive agent monomers.

(d) Coupling of Amine Containing Bioactive Agents with Chloroformate Functionalised Protected Monoglycerides

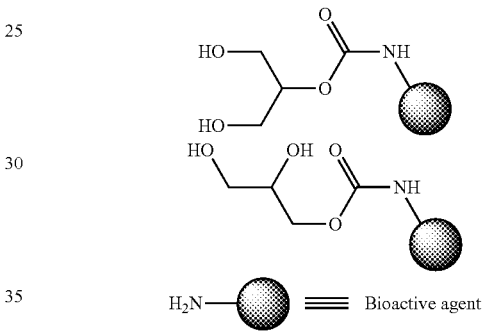

≡ Bioactive agent

An amine containing bioactive agent—such as Benzocaine—(after conversion into a prodrug by protecting additional functional groups with appropriate bioerodable protection groups) is reacted with chloroformate functionalised protected monoglycerides. The monoglyceride protection groups are removed under appropriate conditions giving the monoglyceride functionalised (at the primary or secondary alcohol positions of the glyceride) bioactive agent monomers.

(e) Coupling of Amine Containing Bioactive Agent with Carboxylic Acid Functionalised Protected Monoglyceride

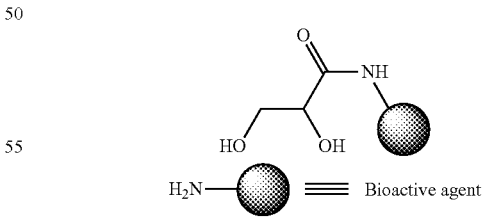

≡ Bioactive agent

An amine containing bioactive agent—such as Benzocaine—(after conversion into a prodrug by protecting additional functional groups with appropriate bioerodable protection groups) is converted into the corresponding isocyanate. Reaction of the isocyanate with a carboxylic acid functionalised protected monoglyceride produces (via release of $CO_2$) the corresponding amide derivative which is subsequently deprotected.

f) Conversion of an Amine Containing Bioactive Agent to an Aromatic Carbamate Containing Functionalised Protected Monoglyceride

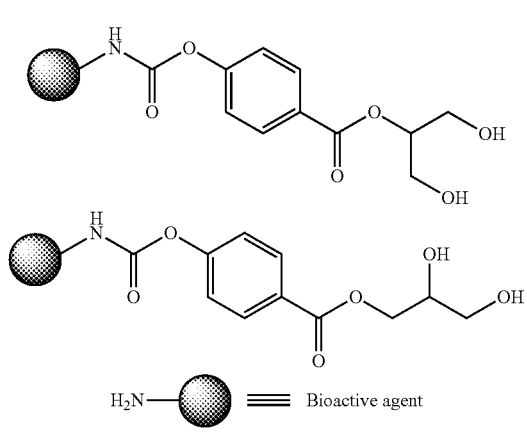

An amine containing bioactive agent—after conversion into a prodrug by protecting additional functional groups with appropriate bioerodable protection groups—is converted into the corresponding functionalised protected monoglyceride containing an aromatic carbamate.

(8) Synthesis of Bioactive Agent-Linker Conjugates
(a) Synthesis of Diacid-Bioactive Agent Conjugates

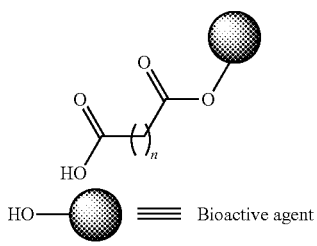

A hydroxy containing bioactive agent—such as Codeine, Fluconazole, Latanoprost or Dexamethasone—(after conversion into a prodrug by protecting additional functional groups with appropriate bioerodable protection groups) is reacted with a diacid or a diacid derivative.

(b) Synthesis of Acid/Omega Hydroxy-Bioactive Agent Conjugates

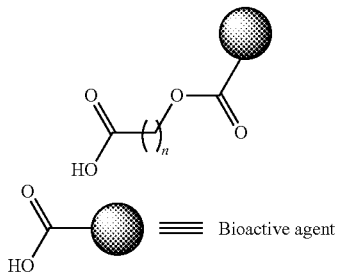

An carboxy acid containing bioactive agent—such as Ciprofloxacin, Levofloxacin or Valproic acid—(after conversion into a prodrug by protecting additional functional groups with appropriate bioerodable protection groups) is reacted with an acid/omega hydroxy linker or a derivative thereof.

(c) Synthesis of an Acid/Chloroformate-Bioactive Agent Conjugates

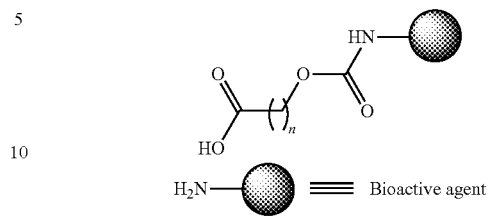

An amine containing bioactive agent—such as Benzocaine—(after conversion into a prodrug by protecting additional functional groups with appropriate bioerodable protection groups) is reacted with a an acid/chloroformate linker or a derivative thereof.

d) Conversion of an Carboxy Acid Containing Bioactive Agent to Functionalised Protected Monoglyceride Containing a Spacer Group.

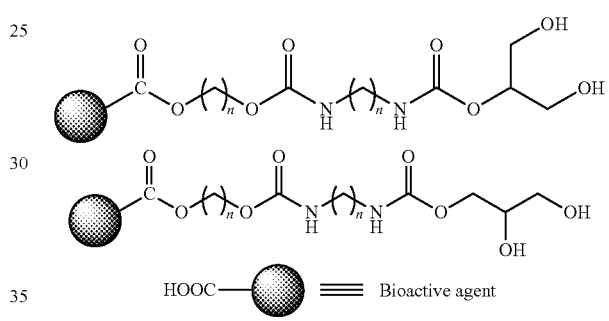

An carboxy acid containing bioactive agent—after conversion into a prodrug by protecting additional functional groups with appropriate bioerodable protection groups—is converted into the corresponding functionalised protected monoglyceride with a spacer group that can be modified to meet the required polymer properties and release kinetics.

e) Conversion of an Alcohol Containing Bioactive Agent to Functionalised Protected Monoglyceride Containing a Spacer Group.

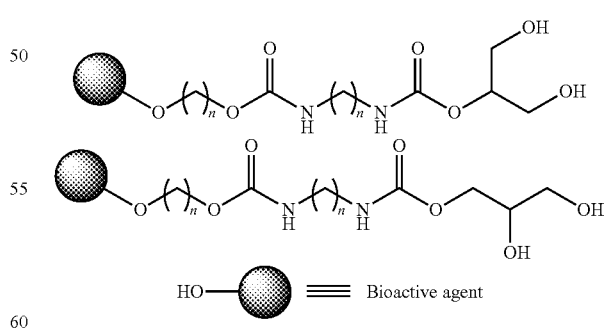

An alcohol containing bioactive agent—after conversion into a prodrug by protecting additional functional groups with appropriate bioerodable protection groups—is converted into the corresponding functionalised protected monoglyceride with a spacer group that can be modified to meet the required polymer properties and release kinetics.

(9) Synthesis of Monoglyceride-Linker-Bioactive Agent-Conjugates (a) Coupling of Diacid-Bioactive Agent Conjugates with Protected Monoglycerides

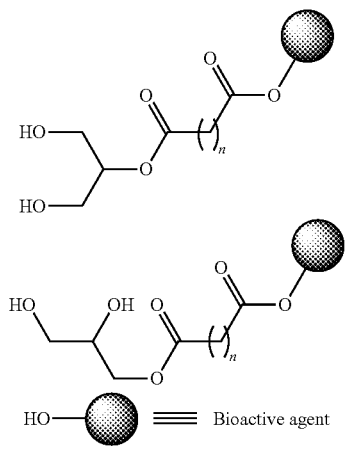

A diacid-bioactive agent conjugate, containing a bioactive agent such as Codeine, Fluconazole, Latanoprost or Dexamethasone—(after conversion into a prodrug by protecting additional functional groups with appropriate bioerodable protection groups) is reacted with protected monoglycerides. The monoglyceride protection groups are removed under appropriate conditions giving the monoglyceride functionalised (at the primary or secondary alcohol positions of the glyceride) bioactive agent monomers.

(b) Coupling of an Omega Hydroxy Acid-Bioactive Agent Conjugate with Protected Monoglycerides

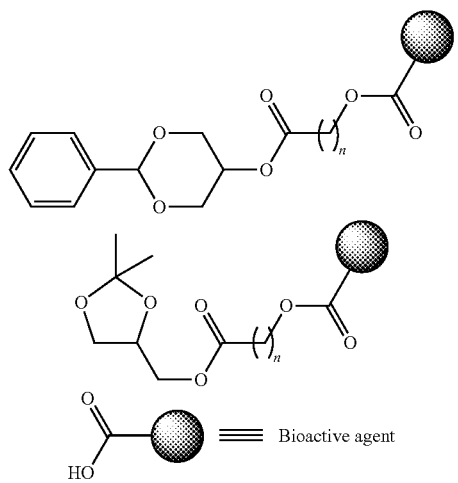

An omega hydroxy acid-bioactive agent conjugate containing a bioactive agent—such as Ciprofloxacin, Levofloxacin or Valproic acid—(after conversion into a prodrug by protecting additional functional groups with appropriate bioerodable protection groups) is reacted with protected monoglycerides. The monoglyceride protection groups are removed under appropriate conditions giving the monoglyceride functionalised (at the primary or secondary alcohol positions of the glyceride) bioactive agent monomers.

(c) Coupling of an Acid/Chloroformate-Bioactive Agent Conjugates with Protected Monoglycerides

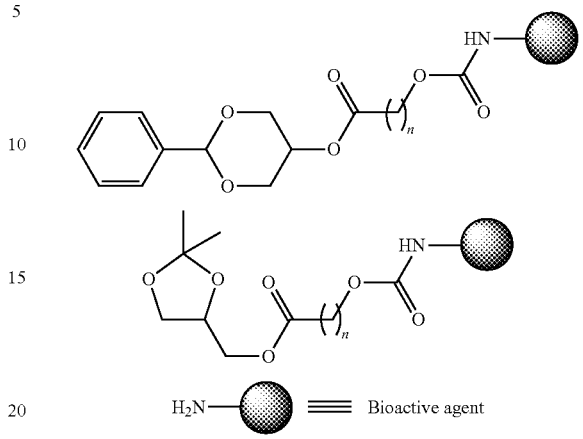

An acid/chloroformate-bioactive agent conjugate containing a bioactive agent—such as Benzocaine—(after conversion into a prodrug by protecting additional functional groups with appropriate bioerodable protection groups) is reacted with protected monoglycerides. The monoglyceride protection groups are removed under appropriate conditions giving the monoglyceride functionalised (at the primary or secondary alcohol positions of the glyceride) bioactive agent monomers.

Conversion of a phosphate containing bioactive agent to functionalised protected monoglyceride (as phosphate ester) with and/or without a spacer group.

X=spacer—as described in the previous text, R=protection group

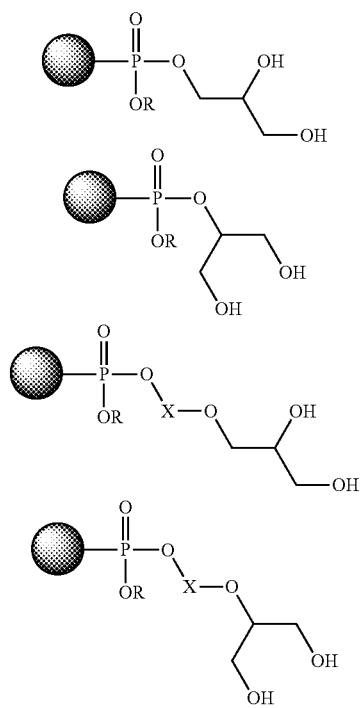

-continued

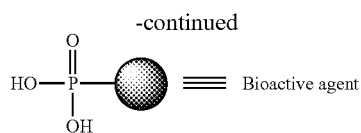 ≡ Bioactive agent

A phosphate containing bioactive agent—after conversion into a prodrug by protecting additional functional groups with appropriate bioerodable protection groups—is converted into the corresponding functionalised protected monoglyceride (as phosphate ester) with or without a spacer group that can be modified to meet the required polymer properties and release kinetics.

Polymer Production

This section describes how the functionalised bioactive-monomers conjugates have been covalently linked to the polymer backbone and formed part of the bioactive-polymer conjugates containing the selected bioactive as a pendant attachment. The pendant attached bioactive is able to be released by the breakdown of the covalent bonds through hydrolysis and the degradation of the linkages attaching the bioactive to the polymer.

Synthesis of Polyols (a) DLLA 1000

To a stirred suspension of DL-Lactic acid (20 mL, 268.3 mmol) and 1,4-butane diol (1.647 mL, 18.6 mmol), tin (II)-2-ethyl hexanoate (2 drops, 0.059 mmol) was added. The reaction was heated at 140° C. under vacuum for 3 days. The resulting pale yellow oil crude material was obtained as the title compound and used without further purification. The molecular weight was determined by GPC using the methods outlined above.

MW: 876.5.

In an alternative procedure, DL-Lactic acid (0.5002 g, 3.47 mmol) was added to a Schlenk flask and anhydrous toluene (1.0 ml) was added. The mixture was agitated to aid dissolution and 2,2'-dithioethanol (0.07 g, 0.591 mmol) tin (II)-2-ethyl hexanoate (0.022 g, 0.069 mmol) were added. The vessel was sealed and stirred at 110° C. for 17.5 hrs. The reaction was cooled and added to 15 ml of hexane and transferred to a centrifuge tube using a small quantity of THF. The mixture was centrifuged, solvent decanted, further hexane added and centrifuged for 5 minutes. The solvent was decanted and the product was dried under high vacuum. The molecular weight was determined by GPC using the methods outlined above.

MW: 1098.53

Polyurethane and Polyester-Urethane Formulations

Polylactic Acid (Mw 1000 g/mol) and polycaprolactone diol (Mw 1000 g/mol) were both dried under high vacuum overnight at 75° C. before use. Hexamethylene diisocyanate (HDI) and Ethyl-lysine diidocyanate (ELDI) were distilled before use.

Polyurethane Bulk Synthesis Method

The required amounts of DLLA, PLGA or PCLD (ERA Chemicals Pty Ltd) polyester polyols were weighed into a beaker and kept warmed in a pre-heated nitrogen purged oven. The required amount of bioactive-monomer conjugate was first dried under vacuum with mild heat then mix added to the reaction beaker containing the DLLA, PLGA or PCLD components and returned to an oven to equilibrate.

The required amount of diisocyanate HDI was weighed into a syringe for addition to the other components. Three drops of Dibutyltin Dilaurate (DBTDL) or 2 Ethyl Hexanoate ((Sn2EH) catalyst were first added to the bioactive-monomer conjugate and/polyol mixture. The monomer/s and catalyst were mixed well before either the HDI or ELDI was added via a syringe. The whole mixture was mixed and stirred vigorously with a spatula until the mixture thickened considerably before it was poured onto a baking tray. The tray was then placed in an oven overnight at 80° C. to cure the polymer.

Optimisation of the molecular weight was achieved by varying the HDI or ELDI index. The molecular weights of the polymers were characterised by Gel Permeation Chromatography (GPC) using THF or DMF as the solvent. Reaction completion and structural integrity were confirmed by means of $^1$H NMR.

Polyurethane Solution Synthesis Method

Bioactive-monomer conjugates were dried under vacuum with mild heat then added to dry DMF (typically >1 g) in a small round bottle flask. Two drops of DBTDL or Sn2EH were added and the mixture warmed in an oil bath at 85° C. before injecting in a slight excess of HDI or ELDI. The mixture was typically found to have thickened considerably after stirring overnight at 85° C. The DMF solvent was removed and the material was then analysed or further purified.

Polyurethane Precipitation Purification Method

The resulting PU was dried to remove any DMF present. The polymer was then dissolved in a minimal amount of DMSO then precipitated from solution into acetonitrile. Any unreacted bioactive-monomer conjugate remained dissolved in the DMF/Acetonitrile solution.

Aliphatic Polyurethanes containing Valproic Acid Monoglyceride (VA-MG)

Comparative Example 1

PU Polymer Bioactive-Conjugate Containing 50 Mole % VA-MG

A polymer-bioactive conjugate containing 50 mole % VA-MG was formed by the reaction of 1:1 molar ratio of VA-MG and HDI according to the Polyurethane Bulk Synthesis Method. The VA-MG synthesised in Example 1 above was dried under vacuum. The VA-MG (1.005 g, 4.6 mmol) was added to a dried 150 ml polypropylene (PP) beaker. DBTDL (dibutyl tin dilaurate) catalyst was added to the beaker (0.0041 g). The mixture was stirred and heated in the beaker at 70° C. for 5 mins. HDI was then added by syringe (1.003 g 5.9 mmol) with stirring. The mixture was then poured into a Teflon coated tray and allowed to cure for 4 hours in an oven at 70° C. Films of the polymer were pressed using a melt press set at 90° C. Teflon coated metal press plates were used. The thickness was controlled using a 200 micron shim plate. The sample was pressed for 5 mins at 90° C. and then cooled to room temperature using tap water (flowing through the press platterns).

The polymer film was found to be clear, flexible and tough. The nominal loading the valproic acid in the polymer is approximately 30 wt %.

Example 13

Flexible PU Polymer Bioactive-Conjugate Containing 33 Mole % VA-MG

A polymer-bioactive conjugate containing 33 mole % VA-MG was formed by the reaction of VA-MG, PCLD1000 and HDI according Polyurethane Bulk Synthesis Method in the proportions 34 mole %, 15 mole % and 51 mole %, respectively. PCLD 1000 (2.508 g, 2.524 mmol) and VA-MG (1.185 g, 5.428 mmol) were added to a dried glass beaker and mixed thoroughly with a spatula. Three drops of DBTDL (dibutyltin dilaurate) catalyst was then added to the polyols mixture. HDI (1.393 g, 8.281 mmol) was delivered by a syringe and vigorous mixing was applied. The hot mixture was then poured onto a Teflon coated tray and placed in an oven to cure overnight at 85° C. Through isocyanate index optimisation, polyurethanes of high molecular weights and strength were synthesised from this formulation. A 250 micron thick film prepared by the process described above was clear, tough. The loading of VA-MG achieved by this formulation is approximately 23.3 wt %.

Aliphatic Polyurethanes Containing Levofloxacin Monoglyceride (LVX-MG)

Example 20

Polyurethane Bioactive-Polymer Conjugate Containing >50 wt % LVX-MG

LVFX-MG (0.20 g, 0.457 mmol) was dissolved in 2.5 ml of dry DMF solvent. Two drops of the DBTDL catalyst was added to the solution and heated to 65° C. in a small round bottle flask with a rubber seal. HDI (0.078 g, 0.464 mmol) added via a micro syringe and allowed to react overnight. After removing the DMF, flaky but brittle solid was produced. After precipitation in acetonitrile solvent, a whitish material was collected.

Example 22

Polyurethane Bioactive-Polymer Conjugate Containing 13 Wt % Bound LVX (as LVX-MG)

DLLA (1.35 g, 1.20 mmol), PCLD (0.38 g, 0.384 mmol) and 3 drops of DBTDL was mixed in a beaker and warmed in an oil bath at 65° C. LVFX-MG (0.65 g, 1.04 mmol) was dissolved in 3 ml of dry DMF solvent. The two mixtures were then combined before injecting in the HDI (0.52 g, 3.09 mmol). Over the course of a few hours, the mixture's viscosity has increased considerably. Transferred the material into a crucible and heated in an oven at 80° C. overnight. After removing the solvent, a sticky waxy material was produced.

TABLE 2

Bioactive-Polyurethane- Conjugates and Bioactive-Polyester-Urethane Conjugates

| Example | Relevant Bioactive Monomer Conjugate Example No and weight (g) | PCLD 1000 (g) | DLLA 1000 (g) | PLGA 50:50 1000 (g) | HDI (g) | ELDI (g) | Catalyst (drops) | Method | Comments |
|---|---|---|---|---|---|---|---|---|---|
| CE-1 | Ex1 1.0053 | 0 | 0 | 0 | 1.0037 | 0 | 5 DBTDL | Bulk | Mn = 9,575 Mw = 15,332 Mp = 15,205 PD = 1.60 Clear hard polymer |
| 13 | Ex1 1.1800 | 2.5086 | 0 | 0 | 1.3900 | 0 | 3 DBTDL | Bulk | Mw 254,869; Mn 127,312. Clear flexible film |
| 14 | Ex2 1.426 | 2.7382 | 0 | 0 | 1.3108 | 0 | 5 DBTDL | Solution | Sticky Clear film |
| 15 | Ex2 0.8500 | 1.6205 | 0 | 0 | 0.7713 | 0 | 3 DBTDL | Solution | Rubbery polymer |
| 16 | Ex3 3.0358 | 0 | 0 | 0 | 1.0855 | 0 | 5 DBTDL | Bulk | Rubbery polymer |
| 17 | Ex3 1.5860 | 2.5071 | 0 | 0 | 0.9844 | 0 | 5 DBTDL | Bulk | Rubbery flexible polymer |
| 18 | Ex3 1.5342 | 2.5185 | 0 | 0 | 0.9762 | 0 | 5 DBTDL | Bulk | Flexible polymer |
| 19 | Ex7 0.4161 LVX-ME * 0.1869 | 0 | 0 | 0 | 0.1652 | 0 | 5 DBTDL | Bulk | Stiff Polymer |
| 20 | Ex7 0.2 | 0 | 0 | 0 | 0.078 | 0 | 2 DBTDL | Solution | Flaky brittle polymer |
| 21 | Ex7 0.2136 LVX-ME * 0.1223 | 0 | 0 | 0 | 0.075 | 0 | 2 DBTDL | Solution ppt Acetonitrile | Stiff polymer |
| 22 | Ex7 0.4511 LVX-ME * 0.1989 | 0.38 | 1.35 | 0 | 0.52 | 0 | 3 DBTDL | Solution | Sticky waxy polymer |
| 23 | Ex7 0.7043 LVX-ME * 0.3018 | 0 | 0 | 0 | 0.2733 | 0 | 5 DBTDL | Solution ppt Acetonitrile | Stiff polymer |
| 24 | Ex8 0.5088 | 0 | 0 | 0 | 0.2002 | 0 | 3 DBTDL | Solution | Stiff Polymer |
| 25 | Ex8 3.022 | 4.9999 | 0 | 0 | 2.0001 | 0 | 3 DBTDL | Solution | Flexible polymer |
| 26 | Ex8 0.8879 | 0 | 0 | 1.5018 | 0.6162 | 0 | 5 DBTDL | Solution | Brittle and hard polymer |

TABLE 2-continued

Bioactive-Polyurethane- Conjugates and Bioactive-Polyester-Urethane Conjugates

| Example | Relevant Bioactive Monomer Conjugate Example No and weight (g) | PCLD 1000 (g) | DLLA 1000 (g) | PLGA 50:50 1000 (g) | HDI (g) | ELDI (g) | Catalyst (drops) | Method | Comments |
|---|---|---|---|---|---|---|---|---|---|
| 27 | Ex8 0.7623 | 1.5140 | 0 | 0 | 0 | 0.7623 | 5 DBTDL | Solution | Soft and waxy polymer |
| 28 | Ex8 0.6034 | 0.5186 | 2.1986 | 0 | 0.6169 | 0 | 5 DBTDL | Solution | stiff polymer |
| 29 | Ex9 0.6529 | 1.2702 | 0 | 0 | 0.5971 | 0 | 5 DBTDL | Solution | Flexible white polymer Mn = 11,979 Mw = 22,898 Pd = 1.91 |
| 30 | Ex9 0.5379 | 1.2499 | 0 | 0 | 0 | 0.7121 | 5 DBTDL | Solution | Flexible white polymer Mn = 14,222 Mw = 28,259 Pd = 1.98 |
| 31 | Ex10 0.86 | 1.7380 | 0 | 0 | 0.8928 | 0 | 5 DBTDL | Solution | Flexible polymer |
| 32 | Ex11 0.70 g | 0 | 0 | 0 | 0.5839 |  | 4 Sn2EH | Bulk | Yellow sticky flexible polymer |
| 33 | Ex12 1.9000 | 3.6861 | 0 | 0 | 1.8119 | 0 | 5 DBTDL | Solution | Flexible polymer |
| 34 | Ex1 0.3184 Ex8 0.6328 Ex9 0.4106 | 2.4988 | 0 | 0 | 1.1624 | 0 | 10 DBTDL | Solution | Tough flexible polymer |
| 35 | Ex1 0.1343 Ex8 0.2437 | 0.6780 | 0 | 0 | 0.31 | 0 | 5 DBTDL | Solution | Tough flexible polymer |

Example 36

Blends of Precipitated PU Bioactive-Polymer Conjugate Containing >50 Wt % LVX-MG with Amorphous PU It was found that polymer produced by selective precipitation was too brittle to melt press. It was decided to melt blend these materials with the amorphous PU's produced for the earlier Levoflocaxin/amorphous PU blend work.

Film samples of the melt blend of the LVX-MG bioactive polymer conjugate (Example 15) with amorphous PU have been produced which contain 10 wt % LVX.

Example 37

Polyurethane Bioactive-Polymer Conjugate Containing Levofloxacin Monoglyceride Levofloxacin monoglyceride (1.5002 g, 3.4 mmol), DBTDL (0.021 g, 0.03 mmol), ELDI (0.7860 g, 3.5 mmol) and PCLD (0.7639 g, 0.7 mmol) in DMF (10 mL) in a Schlenk flask were heated at 80° C. for 24 hours. After cooling the polymer was precipitated by the slow addition to 20 times its volume of diethyl ether. The mixture was centrifuged and the supernatant solvent decanted to give the crude product which was dissolved in the minimum amount of DCM and added to ten times that volume of diethyl ether, centrifuged and the supernatant decanted. This process was repeated once more to isolate the product which was dried overnight under high vacuum to give 1.656 g of polymer product. The molecular weight was determined by GPC using the methods outlined above.

MW: 29,080.

Example 38

Polyurethane Bioactive-Polymer Conjugate Containing Levofloxacin Monoglyceride Levofloxacin monoglyceride (2.01 g, 4.615 mmol), DBTDL (0.0289 g, 0.0459 mmol) and ELDI (1.059 g, 4.68 mmol) in DMF (10 mL) was heated at 80° C. for 24 hours. 100 mL of diethyl ether was placed in a centrifuge tube and to it the cooled reaction mixture was added dropwise with stirring. A white solid separates which clumps together towards the end giving a buff coloured paste. The mixture was centrifuged and the solvent decanted.

The paste was stirred with diethyl ether (50 mL) until the solid separates out and then centrifuged and the solvent decanted. This process was repeated once more and the product was isolated and dried under high vacuum to give the product as 2.409 g of a buff coloured solid. The molecular weight was determined by GPC using the methods outlined above.

MW: 40,890

Polyesters

Reaction of VA-MG with Di-Acids or Anhydrides

VA-MG was dried under high vacuum with magnetic stirring at room temperature in the flasks used for conducting the reaction. The reactions was carried out at 110° C. in 50 mL round bottom flasks fitted with magnetic stirrer bar, a 10 mL capacity Dean and Stark trap and a reflux condenser in the presence of a condensation catalyst (DBTDL). The apparatus were blanketed with nitrogen to prevent moisture ingress.

Toluene distilled from sodium was used as a solvent for the reaction. The collection arm of the Dean and Stark trap was filled with dried molecular sieve (4A) to further promote the removal of water from the reaction mixture Reaction work-up involved the removal of the toluene by rotovap and high vacuum. All samples were washed with 0.1M HCl then water and dried under high vacuum. Reaction completion and structural integrity was confirmed by $^1$H NMR and molecular weights determined by GPC.

Reaction of VA-MG with Acid Chlorides

VA-MG was dried under high vacuum with magnetic stirring at room temperature in the flasks used for conducting the reaction.

The acid chlorides were distilled under vacuum and stored under nitrogen in a freezer before use. DCM was dried over molecular sieve using a solvent delivery system (SDS).

Reactions were carried out in DCM within a 50 mL round bottom flask fitted with magnetic stirrer bar and a reflux condenser. The flasks were blanketed with nitrogen to prevent moisture ingress.

Triethylamine (TEA) was added to the reaction flask in 20% excess to drive the reaction by promoting the formation of the acid chloride salt. The TEA was dried by distillation off calcium hydride under a nitrogen blanket.

Reaction work-up involved washing of the TEA-HCl salt in 0.1M HCL and water, drying the organic layer over anhydrous sodium sulphate, filtering and removal of the DCM by rotovap. All samples were washed with 0.1M HCL then water and dried under high vacuum. Reaction completion and structural integrity was confirmed by $^1$H NMR and molecular weights determined by GPC.

TABLE 3

Bioactive-Polyester- Conjugates Produced by Polycondensation of DiAcids or Anhydrides with Bioactive Monomer Conjugate's

| ID | Bioactive Monomer Conjugate Example No and weight (g) | Succinic Anhydride (g) | Succinic Acid (g) | Adipic Acid (g) | Sebacic Acid (g) | Solvent | Catalyst (drops) | Comments |
|---|---|---|---|---|---|---|---|---|
| Ex39 | Ex1 3.0089 | 1.4531 | 0 | 0 | | Toluene | 10 DBTDL | Waxy polymer |
| Ex40 | Ex1 2.000 g | 0 | 0 | 1.3494 | | Toluene | 10 DBTDL | Waxy polymer |
| Ex41 | Ex1 2.0059 | 2.7382 | 0 | 0 | 1.8522 | Toluene | 10 DBTDL | Waxy polymer |
| Ex42 | Ex8 0.5022 | 0.1154 | 0 | 0 | 0 | Toluene | 10 Sn2EH | Waxy polymer |
| Ex43 | Ex8 0.4807 | 0 | 0.1343 | 0 | 0 | Toluene | 10 Sn2EH | Dark Waxy Polymer |
| Ex44 | Ex8 0.4951 | 0 | 0 | 0.1671 | 0 | DMF | 10 DBTDL | Yellow/Brown Wax |
| Ex45 | Ex8 0.4991 | 0 | 0 | 0 | 0.0.2326 | DMF | 10 Sn2EH | Dark Waxy Polymer |

TABLE 4

Bioactive-Polyester- Conjugates Produced by Reaction of DiAcid Chlorides with Bioactive Monomer Conjugate's

| ID | Bioactive Monomer Conjugate Example No and weight (g) | Succinoyl Chloride (g) | Adipoyl Chloride (g) | Sebacoyl Chloride (g) | Solvent | TEA (Weight) | Mn Mw | Comments |
|---|---|---|---|---|---|---|---|---|
| Ex46 | Ex1 1.2549 | 0 | 0 | 1.3694 | DCM | 1.39 g | Mn = 1647 Mw = 6190 | Wax |
| Ex47 | Ex1 1.3173 | 0 | 1.7289 | 0 | DCM | 1.905 | Mn = 557 Mw = 787 | Yellow Liquid |
| Ex48 | Ex1 1.2008 | 0 | 0 | 2.2823 | | 1.921 | Mn = 2724 Mw = 7016 | Yellow Wax |
| Ex49 | Ex1 2.0688 | 0 | 1.7397 | 0 | | 3.51 | Mn = 619 Mw = 994 | Yellow Liquid |
| Ex50 | Ex1 2.0134 | 0 | 0 | 2.207 | | 2.795 | Mn = 2137 Mw = 7727 | Yellow Wax |

Example 51

Polymer Erosion

The extent of polymer erosion was determined gravimetrically. Samples were weighed prior to and at the end of each erosion experiment. Samples were incubated in isotonic phosphate buffer (IPB), adjusted to pH 7.4 using orthophosphoric acid and containing 0.01% sodium azide as a preservative, and incubated at 37° C. with continuous stirring for the desired period of incubation. At the end of the incubation period samples were washed with distilled water and dried to constant weight.

Drug Release

Following in vitro release guidelines recommended by the International Organisation of Standardisation[9], polymer-coated discs or cylindrical samples were suspended in wire baskets which were immersed in isotonic phosphate buffer (IPB), adjusted to pH 7.4 using orthophosphoric acid and containing 0.01% sodium azide as a preservative, and incubated at 37° C. with continuous stirring. Aliquots of the receptor solution were removed for analysis at predetermined time points until the release from the polymer no longer increased.

The amount of drug released from the polymer-coated discs at the various time points was quantified by reserve phase high performance liquid chromatography (HPLC) with a UV absorbance detector (levofloxacin) and refractive index (valproic acid) and drug separation was performed on a C18 column. Levofloxacin and Valproic Acid were eluted isocratically using a degassed mobile phase.

In Vitro Assessment of Antimicrobial Activity

The antimicrobial activity of polymer-coated discs was assessed using the disc diffusion test based on protocols recommended by the Clinical and Laboratory Standards Institute[10]. Colonies selected from an overnight culture of *S. aureus* ATCC strain 29213 were suspended in phosphate-buffered saline (PBS) at a density of $1.5 \times 10^8$ CFU/ml. The suspension was then used to inoculate the surface of a Mueller-Hinton agar plate. Discs coated on one side only were placed coated-side-down onto the freshly inoculated agar and the plates were incubated at 37° C. in air for 18 hr. Growth inhibition was inspected visually the following day. Discs were then transferred to freshly inoculated agar plates each day until no inhibition of growth occurred.

Example 52

Release of Levofloxacin

Figure 2:
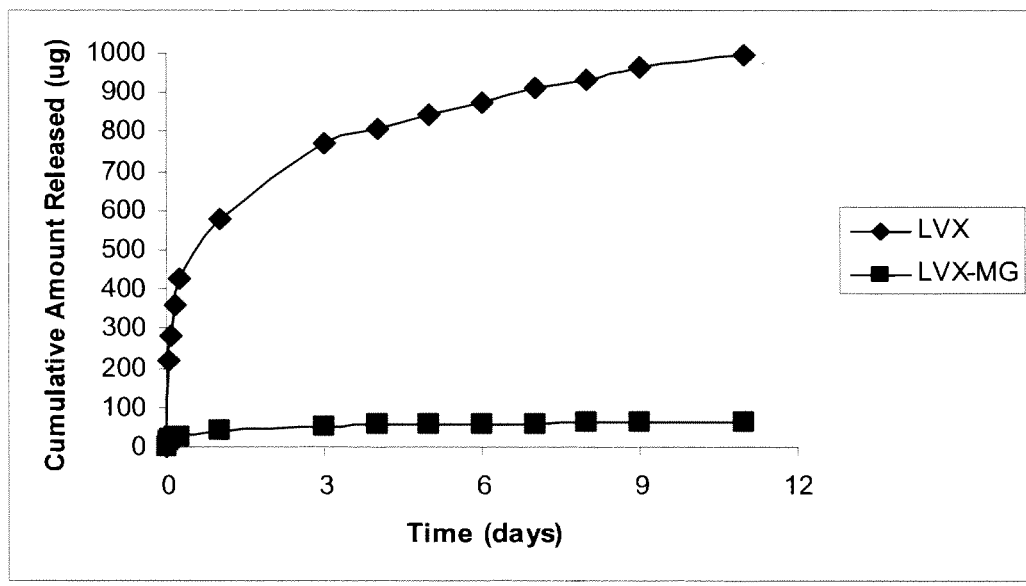
FIG. 2 illustrates in vitro release of Levofloxacin and the corresponding Levofloxacin containing monomer, Levofloxacin-monoglyceride, from a Levofloxacin-polyurethane conjugate produced from a 1:1 molar ratio of Levofloxacin monoglyceride and hexamethyl diisocyanate (Example 20)
Figure 3:
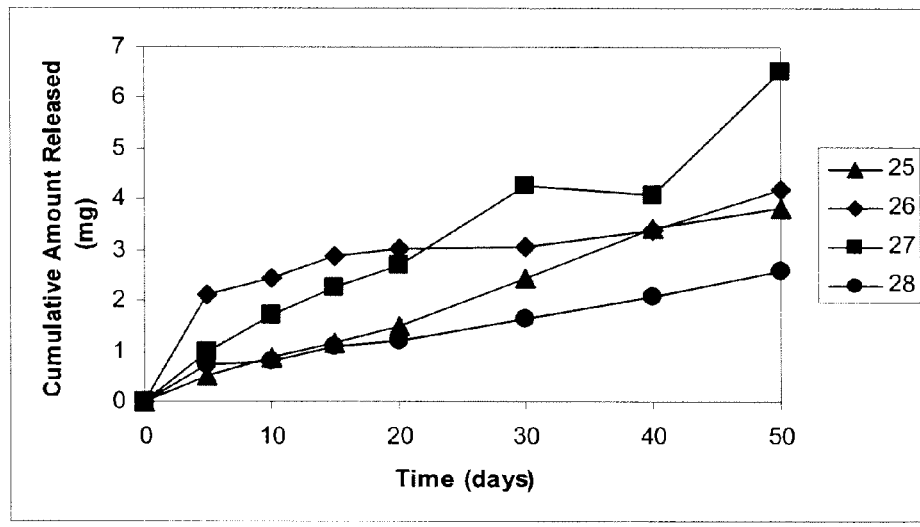
FIG. 3 illustrates in vitro release of Levofloxacin from biodegradable polymers described in examples 25, 26, 27 and 28 showing cumulative amount of levofloxacin released versus time.
Figure 4:
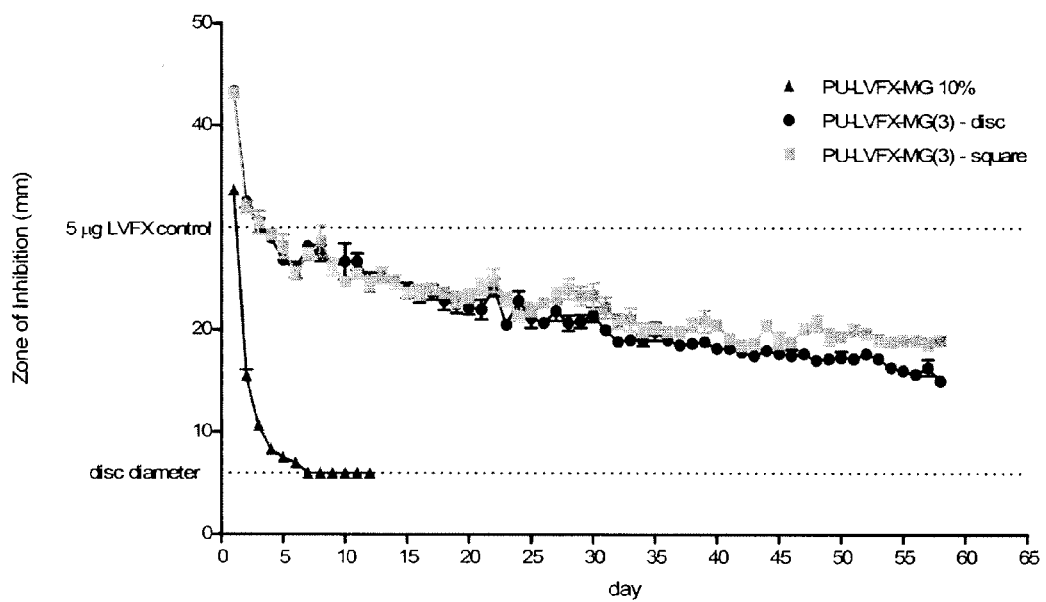
FIG. 4 illustrates antimicrobial activity of levofloxacin-conjugate polymer films against S. aureus. Six mm diameter discs coated on a single side (10% w/w levofloxacin—example 36) (▲) of different geometries (57% w/w levofloxacin—example 20) (●—disc; ■—square) were transferred daily to a freshly inoculated bacterial lawn, incubated and the zone of inhibition measured. Data are the mean zone of inhibition (mm)±standard error measured from six discs.

The following charts show the release of levofloxacin from the polymer systems described in Examples 20, 25, 26, 28, 27, and 36. The amount of levofloxacin was determined by HPLC as previously described at the time intervals given in the chart. FIG. 2 shows the release of both levofloxacin (LVX) and the levofloxacin incorporating monomer, levofloxacin monoglyceride (LVX-MG), from the polymer described in Example 20. The data shows that levofloxacin is released from the polymer as the free active drug with very little released as the inactive levofloxacin-monoglyceride. FIG. 3 shows the release of levofloxacin from a number of different polymers described in Examples 25, 26, 27 and 28. The data shows levofloxacin is released from each of the polymers 25, 26, 27 and 28. FIG. 4 shows an in vitro assessment of antimicrobial activity from polymers described in Examples 20 and 36. Antimicrobial activity is demonstrated in both polymers.

Figure 5:
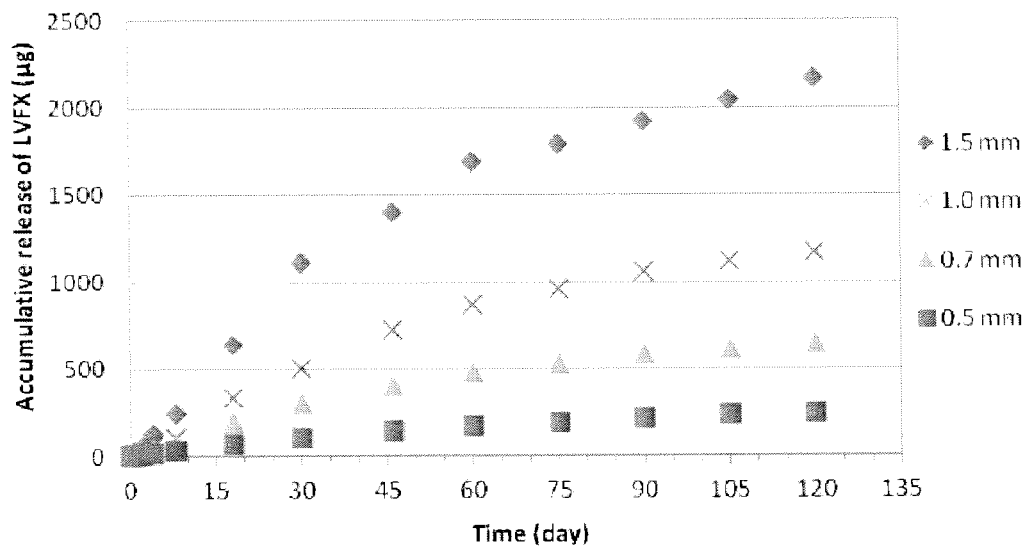
FIG. 5 illustrates in vitro release of Levofloxacin from the biodegradable polymer described in example 37 showing cumulative amount of levofloxacin released versus time.
Figure 6:
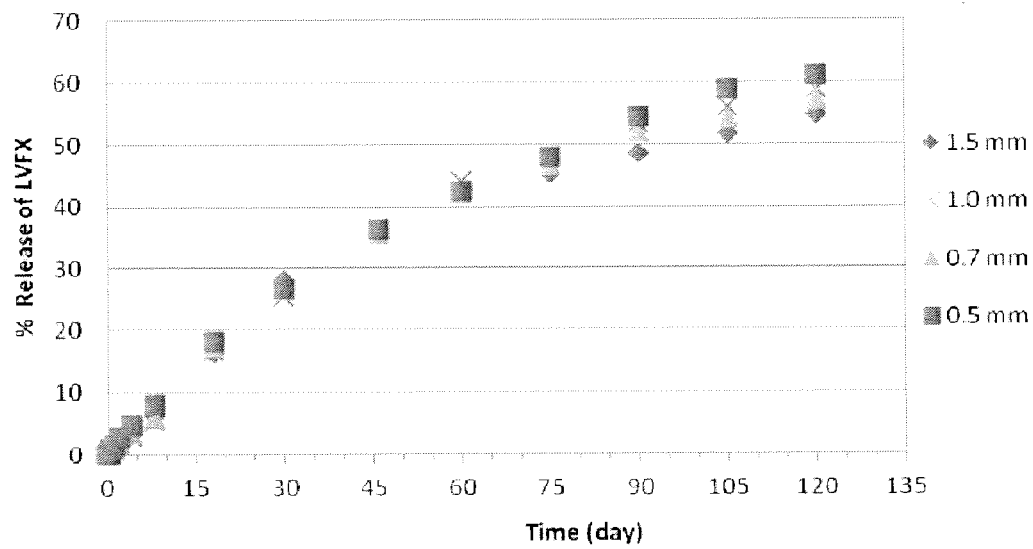
FIG. 6 illustrates in vitro release of Levofloxacin from the biodegradable polymer described in example 37 showing percentage of levofloxacin released from the polymer conjugate versus time.
Figure 7:
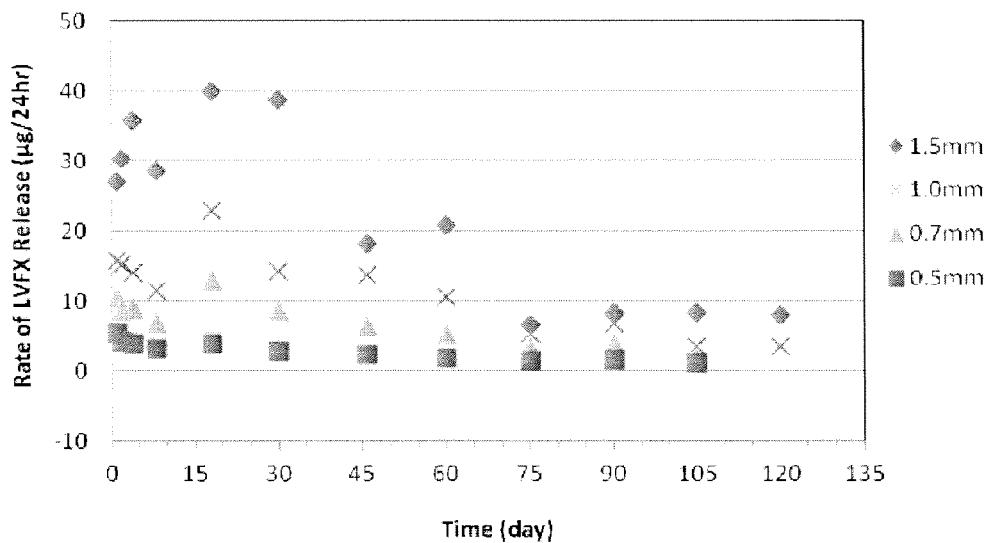
FIG. 7 illustrates in vitro release of Levofloxacin from the biodegradable polymer described in example 37 showing amount of levofloxacin released per 24 hours versus time.

The polymer system of Example 37 was used to form cylinders of constant length and different diameter (0.5 mm, 0.7 mm, 1.0 mm and 1.5 mm). The cumulative release of levofloxacin from the cylinders over a period of 120 days was determined by HPLC and is shown in FIG. 5. FIG. 6 shows the percentage of levofloxacin released from the polymer conjugate over time for each sample. The amount of levofloxacin released per 24 hour period during the study is shown in FIG. 7.

Example 53

Release of Valproic Acid

Figure 8:
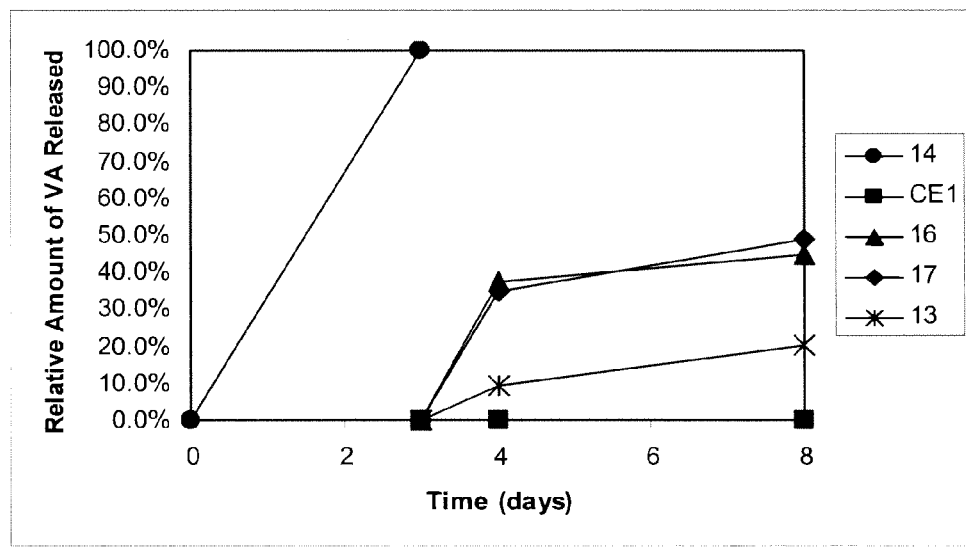
FIG. 8 illustrates in vitro release of Valproic Acid from polymers described in CE1, 13, 14, 16 and 17 showing cumulative amount of Valproic Acid released versus time.

The following charts show the release of Valproic Acid from the polymers described in examples CE1, 14, 16 and 17. The amount of Valproic Acid was determined by HPLC as previously described at the time intervals given in the chart. FIG. 8 shows the release of Valproic Acid from the polymers described in examples CE1, 14, 16, 17. The data shows that Valproic Acid is released from the polymers 14, 16 and 17 but not from polymer CE1. Polymer from example CE1 was produced with Valproic Acid attached directly to the incorporating diol, Glycerol, and from two monomers, Valproic Acid Monoglyceride and HDI, in 1:1 ratio. Polymer examples 16 and 17 used a linker to distance the Valproic Acid from the polymer backbone. Polymer example 13 was produced with an additional polyester polyol component, PCL.

Comparative Example 2

No Release of Valproic Acid

The polymer described in Example 49 was incubated in phosphate buffer (pH 7.4) at 37° C. for 120 hours. Both Valproic Acid and Valproic Acid Monoglyceride were measured by GC-MS. After 120 hours release of VA-MG could be detected but not trace of VA was found. The polymer described in Example 47 was produced from a 1:1 molar ratio of Valproic Acid Monoglyceride and Adipic Acid. As the amount of VA-MG released was greater than the amount of VA released from the polymer, such a polymer lies outside the claims of this patent but serves as a comparator to the polymer claimed within the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A biodegradable polyester polymer which is a copolymer of:
a monomer—bioactive moiety conjugate of formula (II):

where:
X' and Y' are each hydroxyl;
R represents a linear or branched optionally substituted hydrocarbon;
Z is a spacer moiety; and
D is a releasable bioactive moiety; and
at least one selected from the group consisting of:
(i) an alkyl ester of lysine diisocyanate; and
(ii) a polyisocyanate and one or more polyester polyol co-monomers.

2. The biodegradable polymer of claim 1, which is a copolymer of the monomer-bioactive moiety conjugate of formula (II) and (b) an alkyl ester of lysine diisocyanate.

3. The biodegradable polymer of claim 2, which is a copolymer of the monomer-bioactive moiety conjugate of formula (II) and an ethyl ester of lysine diisocyanate.

4. The biodegradable polymer of claim 1, which is a copolymer of the monomer-bioactive moiety conjugate of formula (II) and a polyisocyanate and one or more polyester polyol co-monomers.

5. The biodegradable polymer of claim 4, wherein the polyisocyanate is selected from m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexyl-methane diisocyanates, 1,5-napthylene diisocyanate, 4,4'-diphenylmethane diisocyanate, 2,4' diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, and alkyl esters of lysine diisocyanate.

6. The biodegradable polymer of claim 1, which is a copolymer of the monomer-bioactive moiety conjugate of formula (II) and an alkyl ester of lysine diisocyanate, a polyisocyanate, and a polyester polyol co-monomer.

7. The biodegradable polymer of claim 1, wherein the bioactive moiety (D) is selected from 5-alpha-reductase inhibitors, amebicides, aminosalicylates, anaesthetics (general and local), analgesics, angiotensin inhibitors, anorexiants, antacid agents, anti-angiogenic agents, antianginal agents, antiarrythmic agents, antiarthritic agents, antibiotics, antibacterial agents, antibodies, anticoagulants, anticonvulsants, antidepressants, antiepileptic agents, antifungals, anthelmintics, antihistamines, antihypertensives, antihyperlipidemic agents, antiinfectives, antiinflammatories, antiemetics, antimalarial, antimetabolites, antimigraine, antimitotics, antiparasitic agents, antiparkinson agents, antipsychotics, antiprotozoals, antitussives, antiulcer agents, antivirals, anxiolytics, bronchodilators, decongestants and expectorants, cancer therapy and related pharmaceuticals, cardiovascular pharmaceuticals, central nervous system pharmaceuticals, benzopidazepines, beta-adrenergic blocking agents, bisphosphonates, calcium channel blockers, carbonic anhydrase inhibitors, chemokine receptor antagonist, coumarins and indadiones, cox-2 inhibitors, contraceptives, cytotoxics, diuretics, diabetes therapies, growth hormones, fertility pharmaceuticals, hematinics, glucose modifying agents, growth promoters, H2 antagonists, heparin and heparin antagonists, hormone replacement therapies, hemostatics, immunosuppressants, immunostimulants, inotropic agents, interferons, hormones and analogs, impotence agents, kinase inhibitors, laxatives, leukotriene modifiers, macrolides, mast cell stabilizers, muscle relaxants/stimulants, mydriatics, neuromuscular blocking agents, obesity therapeutics, ophthalmic pharmaceuticals, osteoporosis drugs, pain therapeutics, peptides and polypeptides, peripheral vasodilators, platelet inhibitors/stimulating agents, prolactin inhibitors, protease inhibitors, protein therapeutics, proton pump inhibitors, radiopharmaceuticals, respiratory pharmaceuticals, sedatives, spermicides, steroids, smoking cessation agents, statins, stimulants and tranquilizers, sulphonamides, thyroid drugs, urinary acidifiers/alkalinisers, and vasodilators.

8. The biodegradable polymer of claim 1, wherein D is coupled through Z to R by an ester, amide, thiol, anhydride, imide, carbonate, peroxide, peroxyester, phosphate ester, thioester, sulphate ester, carbamate, azo or boronate ester moiety.

9. The biodegradable polymer of claim 1, wherein Z is selected from —O—; —C(O)—; and optionally substituted: —OC(O)—$C_{1-18}$alkylene-C(O); —C(O)O—$C_{1-18}$alkylene-C(O)—; —NR$^a$C(O)—$C_{1-18}$alkylene-C(O)—; —C(O)O—$C_{1-18}$alkylene-O—; —O—$C_{1-18}$alkylene-NR$^a$—; —OC(O)—$C_{1-18}$alkylene-NR$^a$—; —C(O)—$C_{1-18}$alkylene-NR$^a$—; —OC(O)—$C_{1-18}$alkylene-O—; —C(O)—$C_{1-18}$alkylene-O—; and —C(O)NR$^a$—$C_{1-18}$alkylene-NR$^a$—, where R$^a$ is selected from hydrogen, $C_{1-18}$alkyl, $C_{1-18}$alkynyl, $C_{6-18}$aryl, $C_{3-18}$carbocyclyl, $C_{3-18}$heteroaryl, $C_{3-18}$heterocyclyl, and $C_{7-18}$arylalkyl.

10. The biodegradable polymer of claim 1, wherein R is a linear or branched optionally substituted hydrocarbon having from 1 to 12 carbon atoms.

11. A method for preparing a biodegradable polyester polymer, said method comprising the step of polymerising a monomer-bioactive moiety conjugate of formula (II):

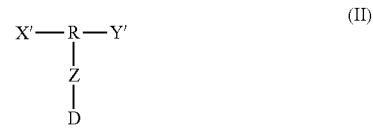

where:
X' and Y' are each hydroxyl; and
R represents a linear or branched optionally substituted hydrocarbon;
Z is a spacer moiety; and
D is a releaseable bioactive moiety;
with at least one selected from the group consisting of:
an alkyl ester of lysine diisocyanate; and
(ii) a polyisocyanate in the presence of one or more polyester polyol co-monomers.

12. The method of claim 11, wherein the monomer-bioactive moiety conjugate of formula (II) is polymerised with an alkyl ester of lysine diisocyanate.

13. The method of claim 12, wherein the monomer-bioactive moiety conjugate of formula (II) is polymerised with an ethyl ester of lysine diisocyanate.

14. The method of claim 11, wherein the monomer-bioactive moiety conjugate of formula (II) is polymerised with a polyisocyanate in the presence of one or more polyester polyol co-monomers.

15. The method of claim 14, wherein the polyisocyanate is selected from m-phenylene diisocyanate, p-phenylene diisocyanate, 2,4-toluene diisocyanate, 2,6-toluene diisocyanate, 1,6-hexamethylene diisocyanate, 1,4-hexamethylene diisocyanate, 1,3-cyclohexane diisocyanate, 1,4-cyclohexane diisocyanate, hexahydro-toluene diisocyanate and its isomers, isophorone diisocyanate, dicyclo-hexylmethane diisocyanates, 1,5-napthylene diisocyanate, 4,4'-diphenylmethane diisocyanate, 2,4' diphenylmethane diisocyanate, 4,4'-biphenylene diisocyanate, 3,3'-dimethoxy-4,4'-biphenylene diisocyanate, 3,3'-dimethyl-diphenylpropane-4,4'-diisocyanate, 2,4,6-toluene triisocyanate, 4,4'-dimethyl-diphenylmethane-2,2',5,5'-tetraisocyanate, and alkyl esters of lysine diisocyanate.

16. The method of claim 11, wherein the monomer-bioactive moiety conjugate of formula (II) is polymerised with an alkyl ester of lysine diisocyanate, a polyisocyanate and a polyester polyol co-monomer.

17. An implantable device comprising the biodegradable polymer of claim 1.

18. An ocular implant comprising the biodegradable polymer of claim 1.

* * * * *